(12) United States Patent
Shoemaker et al.

(10) Patent No.: US 7,807,447 B1
(45) Date of Patent: Oct. 5, 2010

(54) COMPOSITIONS AND METHODS FOR EXON PROFILING

(75) Inventors: Daniel D. Shoemaker, Bothell, WA (US); Stewart Scherer, Moraga, CA (US); Stephen H. Friend, Seattle, WA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 119 days.

(21) Appl. No.: 09/724,538

(22) Filed: Nov. 28, 2000

Related U.S. Application Data

(60) Provisional application No. 60/227,902, filed on Aug. 25, 2000, provisional application No. 60/227,966, filed on Aug. 25, 2000.

(51) Int. Cl.
| | |
|---|---|
| *C12M 1/34* | (2006.01) |
| *C12M 3/00* | (2006.01) |
| *C12Q 1/68* | (2006.01) |
| *C12P 1/34* | (2006.01) |
| *C07H 21/02* | (2006.01) |
| *C07H 21/04* | (2006.01) |

(52) U.S. Cl. ............... 435/287.2; 435/6; 435/91.1; 435/91.51; 435/287.1; 536/23.1; 536/24.3; 536/24.33

(58) Field of Classification Search .......... 435/6, 435/91.1, 283.1, 287.1, 287.2, 91.51; 436/94, 436/501; 536/23.1, 24.3, 24.33, 25.3
See application file for complete search history.

(56) References Cited

U.S. PATENT DOCUMENTS

| 4,946,778 A | 8/1990 | Ladner et al. |
| 5,262,311 A * | 11/1993 | Pardee et al. ............... 435/91.2 |
| 5,445,934 A | 8/1995 | Fodor et al. |
| 5,510,270 A | 4/1996 | Fodor et al. |

(Continued)

FOREIGN PATENT DOCUMENTS

EP    1 006 181 A2    6/2000

(Continued)

OTHER PUBLICATIONS

DeRisi et al., Use of cDNA microassay to analyze expression patterns in human cancer. Nature Genetics, 14, 457-460, 1996.*

(Continued)

*Primary Examiner*—Frank W Lu
(74) *Attorney, Agent, or Firm*—Christensen O'Connor Johnson Kindness PLLC

(57) ABSTRACT

The present invention provides methods for analyzing exon expression profiles of a cell or type of cell. In the invention, the expression levels of a plurality of individual exons or multiexons for each of a plurality of genes in the genome of an organism are measured and analyzed to determine the biological state, such as the exon expression state or transcriptional state, of the cell or type of cell. The methods of the invention are useful for determination of alternative RNA splicing in a plurality of genes. The invention also provides nucleic acid probe arrays for determining in parallel the expression levels of a plurality of exons or multiexons for each of a plurality of genes in the genome of an organism. The invention further provides methods for determining the effects of perturbations, such as perturbations by drugs, on exon expression and alternative RNA splicing pathways.

54 Claims, 10 Drawing Sheets

U.S. PATENT DOCUMENTS

Figure 1:
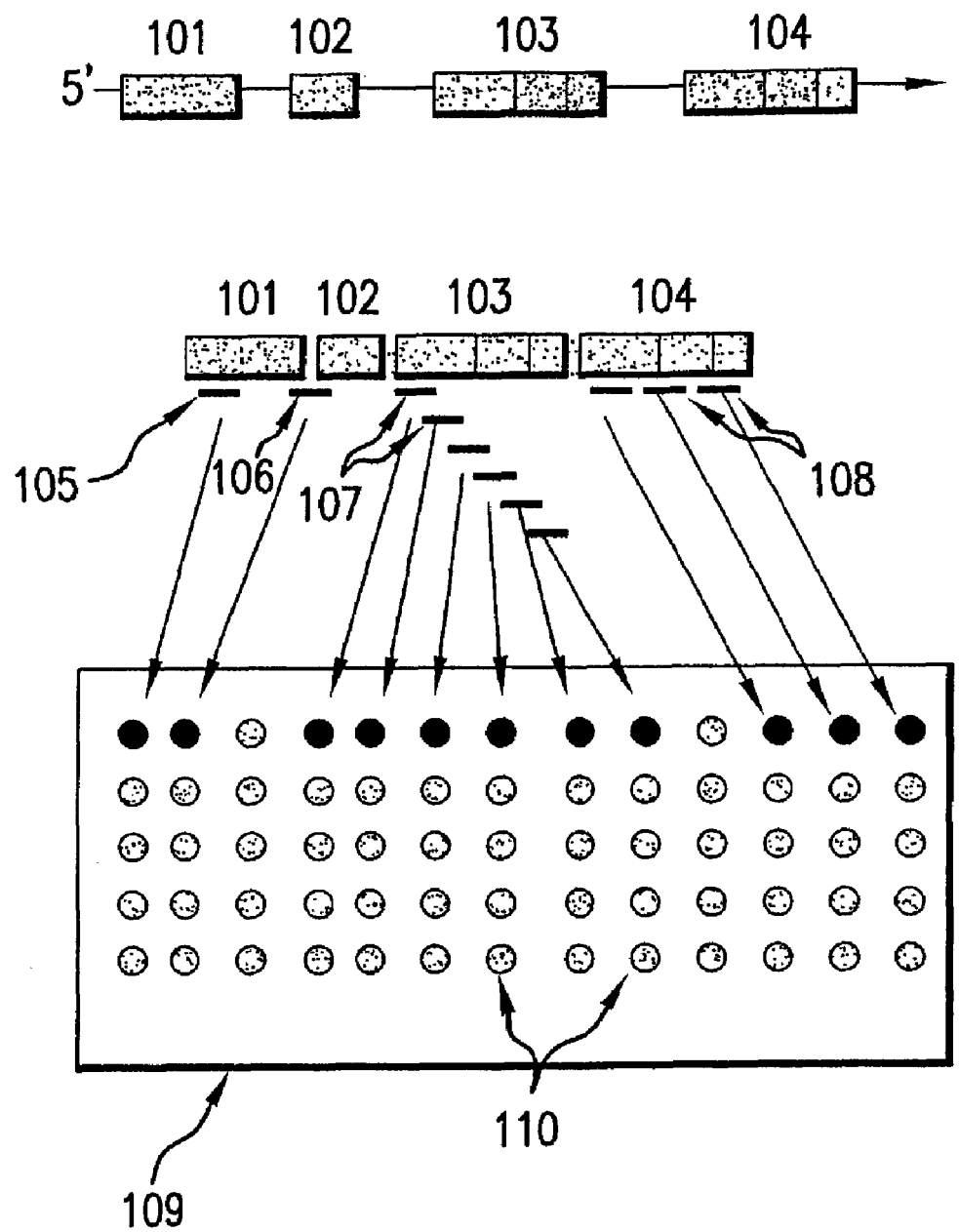

| | | | |
|---|---|---|---|
| 5,539,083 A | 7/1996 | Cook et al. | |
| 5,545,522 A | 8/1996 | Van Gelder et al. | |
| 5,552,270 A | 9/1996 | Khrapko et al. | |
| 5,556,749 A | 9/1996 | Mitsuhashi et al. | |
| 5,556,752 A | 9/1996 | Lockhart et al. | |
| 5,569,588 A | 10/1996 | Ashby et al. | |
| 5,578,832 A | 11/1996 | Trulson et al. | |
| 5,593,839 A | 1/1997 | Hubbell et al. | |
| 5,716,785 A | 2/1998 | Van Gelder et al. | |
| 5,723,320 A | 3/1998 | Dehlinger | |
| 5,744,305 A | 4/1998 | Fodor et al. | |
| 5,811,234 A * | 9/1998 | Roninson et al. | 435/6 |
| 5,817,461 A | 10/1998 | Austin et al. | |
| 5,837,832 A | 11/1998 | Chee et al. | |
| 5,856,103 A | 1/1999 | Gray et al. | |
| 5,891,636 A | 4/1999 | Van Gelder et al. | |
| 5,965,352 A | 10/1999 | Stoughton et al. | |
| 6,027,890 A | 2/2000 | Ness et al. | |
| 6,028,189 A | 2/2000 | Blanchard | |
| 6,040,138 A | 3/2000 | Lockhart et al. | |
| 6,054,270 A | 4/2000 | Southern et al. | |
| 6,110,676 A | 8/2000 | Coull et al. | |
| 6,110,711 A | 8/2000 | Serafini et al. | |
| 6,132,969 A | 10/2000 | Stoughton | |
| 6,132,997 A | 10/2000 | Shannon | |
| 6,146,593 A | 11/2000 | Pinkel et al. | |
| 6,146,830 A | 11/2000 | Friend et al. | |
| 6,156,502 A | 12/2000 | Beattie | |
| 6,165,709 A * | 12/2000 | Friend et al. | 435/4 |
| 6,171,798 B1 | 1/2001 | Levine et al. | |
| 6,203,987 B1 | 3/2001 | Friend et al. | |
| 6,218,122 B1 | 4/2001 | Friend et al. | |
| 6,222,093 B1 | 4/2001 | Marton et al. | |
| 6,251,590 B1 | 6/2001 | Schweighoffer et al. | |
| 6,271,002 B1 | 8/2001 | Linsley et al. | |
| 6,324,479 B1 | 11/2001 | Friend et al. | |
| 6,355,431 B1 * | 3/2002 | Chee et al. | 435/6 |
| 6,713,257 B2 * | 3/2004 | Shoemaker et al. | 435/6 |
| 6,881,571 B1 | 4/2005 | Schweighoffer et al. | |
| 2003/0165931 A1 | 9/2003 | Tocque et al. | |
| 2004/0191828 A1 | 9/2004 | Schweighoffer et al. | |

FOREIGN PATENT DOCUMENTS

| | | |
|---|---|---|
| WO | WO 88/09810 | 12/1988 |
| WO | WO 90/11364 | 10/1990 |
| WO | WO 98/38329 | 9/1998 |
| WO | WO 98/41531 | 9/1998 |
| WO | WO 99/09164 | 2/1999 |
| WO | WO 99/11820 | 3/1999 |
| WO | WO 99/15701 | 4/1999 |
| WO | WO 99/19357 | 4/1999 |
| WO | WO 99/23256 A1 | 5/1999 |
| WO | WO 99/28506 | 6/1999 |
| WO | WO 99/34004 | 7/1999 |
| WO | WO 99/43848 | 9/1999 |
| WO | WO 99/57315 | 11/1999 |
| WO | WO 99/57322 | 11/1999 |
| WO | WO 99/58708 | 11/1999 |
| WO | WO 99/59037 | 11/1999 |
| WO | WO 99/64630 | 12/1999 |
| WO | WO 99/66067 | 12/1999 |
| WO | WO 00/05414 | 2/2000 |
| WO | WO 00/08157 | 2/2000 |
| WO | WO 00/24936 | 6/2000 |
| WO | WO 00/34523 | 6/2000 |
| WO | WO 00/34652 | 6/2000 |
| WO | WO 00/39336 | 7/2000 |
| WO | WO 00/43942 | 7/2000 |
| WO | WO 00/47766 | 8/2000 |
| WO | WO 00/47767 | 8/2000 |
| WO | WO 00/53811 | 9/2000 |
| WO | WO 00/53811 A1 | 9/2000 |
| WO | WO 00/56929 | 9/2000 |
| WO | WO 00/62827 | 10/2000 |
| WO | WO 00/65088 | 11/2000 |
| WO | WO 00/77261 | 12/2000 |
| WO | WO 00/79006 | 12/2000 |
| WO | WO 01/02839 | 1/2001 |
| WO | WO 01/04352 | 1/2001 |
| WO | WO 01/57251 | 8/2001 |
| WO | WO 01/57252 | 8/2001 |
| WO | WO 01/81632 | 11/2001 |

OTHER PUBLICATIONS

Saegusa et al., Up-regulation of CD44 variant exon expression in endometrial carcinomas: analysis of mRNA and protein isoforms, and relation to clinicopathological factors. Jpn. J. Cancer Res., 89, 291-298, 1998.*
U.S. Appl. No. 60/227,966, filed Aug. 25, 2000, Shoemaker et al.
U.S. Appl. No. 60/227,902, filed Aug. 25, 2000, Shoemaker et al.
U.S. Appl. No. 60/154,563, filed Sep. 17, 1999, Burchard.
U.S. Appl. No. 60/090,046, filed Jun. 19, 1998, Friend and Stoughton.
U.S. Appl. No. 60/084,742, filed May 8, 1998, Friend and Stoughton.
U.S. Appl. No. 09/364,751, filed Jul. 30, 1999, Friend et al.
U.S. Appl. No. 09/220,275, filed Dec. 23, 1998, Friend et al.
U.S. Appl. No. 09/616,849, filed Jul. 14, 2000, Burchard.
U.S. Appl. No. 09/220,142, filed Dec. 23, 1998, Friend et al.
U.S. Appl. No. 09/222,596, filed Dec. 28, 1998, Stoughton and Dai.
Ahrendt et al., 1999, Proc. Natl. Academy of Science USA 96:7382-87.
Altschul et al., 1997, Nucl. Acids Res. 25:3389-3402.
Altschul et al., 1990, J. Mol. Biol. 215:403-410.
Anderson et al., 1994, Adv. Immunol. 56:171-178.
ATCC T1B-152 (printed from http://phage.atcc.org on Jul. 3, 2000).
ATCC CCL-243(printed from http://phage.atcc.org on Jul. 3, 2000).
Bass, 2000, Cell 101:235-238.
Bell et al., 1998, Molecular and Cellular Biology 18:5930-5941.
Belshaw et al., 1996, Proc. Natl. Acad. Aci. USA 93:4604-4607.
Bernoist and Chambon, 1981, Nature 290:304-310.
Biocca and Cattanco, 1995, Trends Cell Biol. 5:248-252.
Blanchard et al., 1996, Natural Biotechnology 14:1649.
Blanchard et al., 1996, Biosensors and Bioelectronics 11:687-690.
Blanchard, 1998, *Synthetic DNA Arrays in Genetic Engineering* (Plenum Press, New York) vol. 20 pp. 111-123.
Blanchard, 1999, Nat. Biotechnology 17:953.
Boguski and Schuler, 1995, Nat. Gen. 10:369-371.
Bradbury et al., 1995, *Antibody Engineering* (IRL Press) vol. 2 pp. 295-361.
Brett et al., 2000, FEBS Letter 474:83-86.
Brinster et al., 1982, Nature 296:39-42.
Brunel, 1998, Neural Computation 10(7):1731-1757.
Bugawan et al., 1990, Immunogenetics 32:231-241.
Bugawan et al., 1994, Tissue Antigens (Denmark) 44:137-147.
Burke et al., 1984, Cell 36:847-856.
Burns et al., 1989, Proc. National Academy of Science U.S.A. 85:3798-3802.
Burset et al., 1996, Genomics 34:353-367.
Bussey et al., 1995, Proc. Natl. Acad. Sci. USA 92:3809-3813.
Caceres et al., 1994 Science 265: 1706-1709.
Caudevilla et al., 1998, Proc. National Academy of Science, U.S.A. 95: 12185-12190.
Cech et al., 1987, Science 236:1532-1539.
Chee et al., 1996, Science 274: 610-614.
Chetverin and Kramer, 1994, Bio/Technology 12:1093-1099.
Chirgwin et al., 1979, Biochem. 18:5294-5299.
Claverie, 1996, Meth. Enzymol. 266:212-227.
Cole et al., 1985, Monoclonal Antibodies and Cancer Therapy (Alan R. Liss, Inc.) pp. 77-96.
Cotten and Birnstiel, 1989, EMBO J. 8:3861-3866.
Crollius et al., 2000 Nature Genetics 25:235-238.
Cronin et al., 1996, Human Mutation 7:244-255.

Crook et al., 1998, Nat. Med. 4: 452-455.
DeRisi et al., 1996, Nat. Gen. 14:457-460.
Dohmen et al., 1994, Science 263:1273-1276.
Duggan et al., Nature Genetics, Supplement 21: 10-14.
Dujon et al., 1994, Nature 369:371-378.
Egholm et al., 1993, Nature 363:566-568.
Ewing et al., 2000, Nature Genetics 25:232-234.
Feldman et al., 1994, EMBO J. 13:5795-5809.
Ferguson et al., 1996, Nat. Biotech. 14:1681-1684.
Florea et al., 1998, Genome Res. 8:967-974.
Fodor et al., 1991, Science 251:767-773.
Froehler et al., 1986, Nucl. Acids Res. 14:5399-5407.
Galibert et al., 1996, EMBO J. 15:2031-2049.
Gari et al., 1997, Yeast 13:837-848.
Gautier et al., 1987, Nucl. Acids Res. 15:6625-6641.
Gelfand, 1990, Nucleic Acids Res. 18: 5865-5869.
Gelfand, 1993, Biosystems 30:173-182.
Dralyuk et al., 2000, "ASDB: database of alternatively spliced genes", Nucleic Acids Research, 28(1): 296-2997.
Gibson, 1996, Cancer and Metastasis Rev. 15:287-299.
Goffeau et al., 1996, Science 274:546-567.
Good et al., 1997, Gene Ther. 4:45-54.
Gossen et al., 1995, Proc. Natl. Acad. Sci. USA 89:5547-5551.
Grant, 1999, Cell 96:303-306.
Grassi and Marini, 1996, Ann. Med. 28:499-510.
Griffiths et al., 1994, EMBO J. 13:3245-3260.
Guigo et al., 1992, J. Mol. Biol. 226:141-157.
Guo et al., 1994, Nucleic Acids Research 22:5456-5465.
Guo et al., 1995, Cell 81:611-620.
Guo, 1996, Dissertation, University of Wisconsin.
Hacia et al., 1996, Nat. Genet. 14: 441-447.
Hacia et al., 1998, Nucleic Acids Research 26:49975-4982.
Hacia et al., 1998, Genome Research 8:1245-1258.
Croft et al., 2000, "ISIS, the intron information system, reveals the high frequency of alternative splicing in the human genome", Nature Genetics, 24: 340-341.
Hanke, 1996, J. Bil. Chem. 271: 695-701.
Haseloff and Gerlach, 1988, Nature 334:585-591.
Hayden et al., 1997, Curr. Opin. Immunol. 9:210-212.
Hershkowitz, 1987, Nature 329:219-222.
Hoffman et al., 1996, Proc. Natl. Acad. Sci. USA 83:5185-5190.
Hoffman et al., 1997, Nucl. Acids. Res. 25:1078-1079.
Hong et al., 2000, American Journal of Respiratory Cell and Molecular Biology, 23:355-63.
http://ftp.genome.washington.edu/cgi-bin/RepeatMasker.
Hu et al., 2001, "Predicting Splice Variant from DNA Chip Expression Data", Genome Research 11:1237-1245.
Hughes et al., 2000, Cell 102:109-26.
Huse et al., 1989, Science 246:1275-1281.
Hutchinson et al., 1992, Nucleic Acids Res. 20:3453-3462.
Hyndman et al., 1996, Biotechniques 20:1090-1097.
Inoue et al., 1987, FEBS Lett. 215:327-330.
Inoue et al., 1987, Nucl. Acids Res. 15:6131-6148.
Jiang et al., 1999, Proc. Aoc. Exp. Bio. Med. 220:64-72.
Johnston et al., 1994, Science 265:2077-2082.
Johnston et al., 1984, Mol. Cell. Biol. 4(8):1440-1448.
Kerjan et al., 1986, Nucl. Acids Res. 14:7861-7871.
Khrapko et al., 1991, J. DNA Sequencing and Mapping 1:375-388.
Khrapko et al. 1991, Molecular Biology 25:581-591.
Khrapko, 1999, "Harvard Nathan Shock Center: High Throughput Technology Core" http://www.hms.harvard.edu/aging/nathan/high.html.
Khrapko et al., 1999, Poster Abstract, Chips to Hits '99 Conference, Nov. 2-5, 1999.
Ko et al., 1993, Mol. Cell. Biol. 13:638-648.
Kohler and Milstein, 1975, Nature 256:495-497.
Koizumi et al., 1988, FEBS Lett. 228:228-230.
Koizumi et al., 1988, FEBS Lett. 239:285-288.
Kozbor and Roder, 1983, Immunol. Today 4:72-79.
Kraus et al., 1997, Human Genetics 99_374-380.
Kricka, 1992 Nonisotopic DNA Probe Techniques, Academic Press, San Diego, CA.
Lehman et al., 2000, Cancer Research 60: 10162-1069.
Lemaitre et al., 1989, Proc. Natl. Acad. Sci. USA 84:648-652.
Lestinger et at., 1989, Proc. National Academy of Science, U.A.S. 86:6553-6556.
Lipshutz et al., 1999, Natue Genetics, Supplement 21:20-24.
Lockhart et al., 1996, Nat. Biotech. 14(13):1675-1680.
Lodish et al., 1995, *Molecular Biology of the Cell* (W.H. Freeman and Co., New York) Chapter 8.
Maldonado-Rodriguez et al., 1999, Molecular Biotechnology 11:1-12.
Marton et al., 1983, Tetrahedron Lett. 24: 246-248.
Marks et al., 1992, J. Biol. Chem. 267:16007-16010.
Mascorro-Gallardo et al., 1996, Gene 172:169-170.
Maskos and Southern, 1992, Nucl. Acids Res. 20:1679-1684.
McBride and Caruthers, 1983, Tertahedron Lett. 24:245-248.
McGall et al., 1996, Proc. Natl. Acad. Sci., USA 93:13555-13560.
Milner et al., 1997, Nature Biotechnology 15: 538-541.
Mironov et al., 1999, Genome Research 9: 1288-1293.
Miyoshi et al., 1995, Nucl. Acids Res. 23:2762-2769.
Morgan et al., 1988, Immunol. Today 9:84-86.
Morrison et al., 1984, Proc. Natl. Acad. Sci. USA 81:6851-6855.
Mottes et al., 1995, Neuron 14: 613-623.
Mumberg et al., 1994, Nucl. Acids Res. 22:5767-5768.
Dunham et al., Nature, Dec. 2, 1999 402:(6761):489-95.
Neuberger et al., 1984, Nature 312:604-608.
Nguyen et al., 1995, Genomics 29:207-209.
No et al., 1996, Proc. Natl. Acad. Sci. USA 93(8):3346-3351.
Nocka et al., 1990, EMBO J. 9:1805-1813.
Okada et al., 1994, Cancer Research 54: 3979-3982.
Paulus et al., 1996, J. Virol. 70:62-67.
Pease et al., 1994, Proc. Natl. Acad. Sci. USA 91:5022-5026.
Perlmutter and Alberola, 1996, Curr. Opin. Immunol. 8:285-290.
Petcherski et al., 2000, Nature 405:364-368.
Pettitt et al., 1996, Dev. 122:4149-4157.
Potter et al. 1986, Gene (Netherlands) 48: 229-239.
Press et al., 1992, "Solution of Linear Algebraic Equations" *Numerical Recipes in C* (Cambridge University Press) Chapter 2.
Ramirez-Solis et al., 1993, Meth. Enzymol. 225:855-878.
Ray et al., 1997, Proc. Natl. Acad. Sci. USA 94:3229-3234.
Reese e tal., 2000, Genome Res. 10:483-501.
Reyes et al., 1991, Molecular and Cellular Biology, 11: 1654-1661.
Rogozin et al., 1999, Gene 226: 129-137.
Santa Lucia, 1998, Proc. Natl. Acad. Sci. USA 95:1460-1465.
Sarin et al., 1988, Proc. Natl. Acad. Sci. USA 85:7448-7451.
Sarver et al., 1990, Science 247:1222-1225.
Schena et al., 1996, Proc. Natl. Acad. Sci. USA 93:10614-10619.
Schena et al., 1995, Science 270:467-470.
Schuler, 1997, J. Mol. Med. 75:694-698.
Schuler et al., 1996, Science 274:540-546.
Shalon et al., 1996, Genome Res. 6(7):639-645.
Shimizu et al., 1992, J. Biochem. 111:272-277.
Shirvan et al., 1994, Biochemistry, 33: 6888-6901.
Shoemaker et al., 2001, Nature 409: 922-927.
Snyder et al., 1994, Nucleic Acids Res. 21: 607-613.
Solovyev et al., 1994, Nucleic Acids Res. 22: 5156-5163.
Southern et al., 1992, Genomics 13:1008-1017.
Southern et al., 1994, Nucl. Acids. Res. 22:1368-1373.
Spencer, 1996, Trends Gen. 12:181-187.
Spradling et al., 1995, Proc. Natl. Acad. Sci. USA 92:10824-10830.
Stein et al., 1988, Nucl. Acids Res. 16:3209-3221.
Stephan et al., 2000, Molecular Genetics and Metabolism 70: 10-18.
Stickeler et al., 1999, Oncogen 18: 3574-3582.
Straus and Weiss, 1992, Cell 70:585-593.
Tabara et al., 1999, Cell 99: 123-132.
Takahashi et al, 2000, Cancer Genetics and Cytogenetics 121:38-43.
Takeda et al., 1985, Nature 314:452-454.
Thomas and Capecchi, 1987, Cell 51:503-512.
Tijessen, 1993, Hybridization with Nucleic Acid Probes, 1992, Elseveir Science Publishers.
Uberbacher et al., 1991, Proc. Natl. Acad. Sci. USA 88: 11261-11265.
van der Krol et al., 1988, BioTechniques 6:958-976.
Wagner et al., 1981, Proc. Natl. Acad. Sci. USA 78:1441-1445.

Wang et al., 2000, Journal of Neurology Nuerosurgery and Psychiatry 69:652-654.
Weissensteiner, 1998, Nucleic Acids Res. 26: 687.
Werner, 2001, Biomolecular Engineering 17:87-94.
Wilson, et al., 1997, Oncogene 14: 1-16.
Wolfsberg, et al., 1997, Acids Res. 25: 1626-1632.
www.ncbi.nlm.nih.qov Genbank Accession U83115. Human non-lens beta gamma-crystallin like protein (AIM1) mRNA, partial cds. (Printed Sep. 1, 2000).
www.ncbi.nlm.nih.gov Genbank Accession M62829. Human transcription factor ETR103 mRNA, complete cds (Printed on Sep. 1, 2000).
www.ncbi.nlm.nih.gov Genbank Accession D43968. Human AML1 mRNA for AML1b protein (alternatively spliced product), complete cds (Printed on Sep. 1, 2000).
www.ncbi.nlm.nih.gov Genbank Accession U18778. *Saccharomyces cerevisiae* chromosome V cosmids 9537, 9581, 9495, 9867, and lambda clone 5898 (Printed on Sep. 1, 2000).
www.ncbi.n.m.nih.gov/UniGene (Printed on Jan. 5, 2000).
Xueshan et al., 2000, Chinese Ophthalmic Research 18: 490-492.
Yamamoto et al., 1980, Cell 22:787-797.
Zamore et al., 2000, Cell 101: 25-33.
Zhang and Madden, 1997, Genome Res. 7:649-656.
Zhang et al., 2000, Japanese Journal of Ophthalmology 44: 596-600.
Zon, 1988, Pharm. Res. 5:539-549.
Wilfinger et al., 1997 BioTechniques vol. 22, No. 3, "PCR-Based Method for Isolation of Full-Length Clones and Splice Variants from cDNA Libraries" pp. 481-486.
Modrek et al., 2002, Nature Genetics, vol. 30, "A gnomic view of alternative splicing" pp. 13-19.
Miki et al., 2001, Proc. Natl. Acad. Sci. USA vol. 98, No. 5, "Delineating developmental and metabolic pathways in vivo by expression profiling using the RIKEN set of 18,816 full-length enriched mouse cDNA arrays" pp. 2199-2204.
Megonigal et al., 2000, Proc. Natl. Acad. Sci. USA vol. 97, No. 17, "Panhandle PCR for cDNA: A rapid method for isolation of MLL fusion transcripts involving unknown partner genes" pp. 9597-9602.
Jain, 2000, Tibtech, vol. 18, "Biotechnological applications of lab-chips and microarrays" pp. 278-280.

U.S. Appl. No. 09/632,366, filed Aug. 3, 2000, Penn et al.
U.S. Appl. No. 09/608,408, filed Jun. 30, 2000, Penn et al.
U.S. Appl. No. 60/180,312, filed Feb. 4, 2000, Penn et al.
U.S. Appl. No. 60/199,484, filed Apr. 25, 2000, Balaban
U.S. Appl. No. 60/208,794, filed Jun. 1, 2000, Balaban.
Busting, 2000, "Absolute quantification of mRNA using real-time reverse transcription polymerase chain reaction assays" J. Mol. Endocrinology 25:169-193, published Oct. 2000.
Martell et al., 1999, "High-throughput real-time reverse transcription-PCR quantitation of hepatitis C virus RNA" J. Clin. Micro. 37:327-332.
Kafert et al., 1999, "Differential quantitation of alternatively spliced messenger RNAs using isoform-specific real-time RT-PCR" Anal. Biochem. 269:210-213.
Robinson et al., 1997, "Quantification of alternatively spliced RUSH mRNA isoforms by QRT-PCR and IP-RP-HPLC analysis: a new approach to measuring regulated splicing efficiency" Gene 198:1-4.
Lollmann et al., 1997, "Detection and quantification of the leptin receptor splice variants Ob-Ra, b, and e in different mouse tissues" Biochem. Biophys. Res. Comm. 238:648-652.
Fei et al., 1997, "Anatomic localization of alternatively spliced leptin receptors (Ob-R) in mouse brain and other tissues" Proc. Natl. Acad. Sci. USA 94:7001-7005.
Claverie, 1997, "Computational methods for the identification of genes in vertebrate genomic sequences," *Human Molecular Genetics* 6: 1735-1744.
Dennis, 2001, "Tiled arrays for gene hunting," *Nature Reviews* 2: 161.
Lashkari, et al., 1997, "Yeast microarrays for genome wide parallel genetic and gene expression analysis," Proc Natl Acad Sci U S A 94:13057-13062.
Lipshutz, et al., 1995, Using Oligonucleotide Probe Arrays to Access Genetic Diversity, *BioTechniques* 19:442-447.
International Search Report of International Application PCT/US01/26274, dated Jan. 13, 2003.
Written Opinion of International Application PCT/US01/26274, dated May 20, 2003.

* cited by examiner

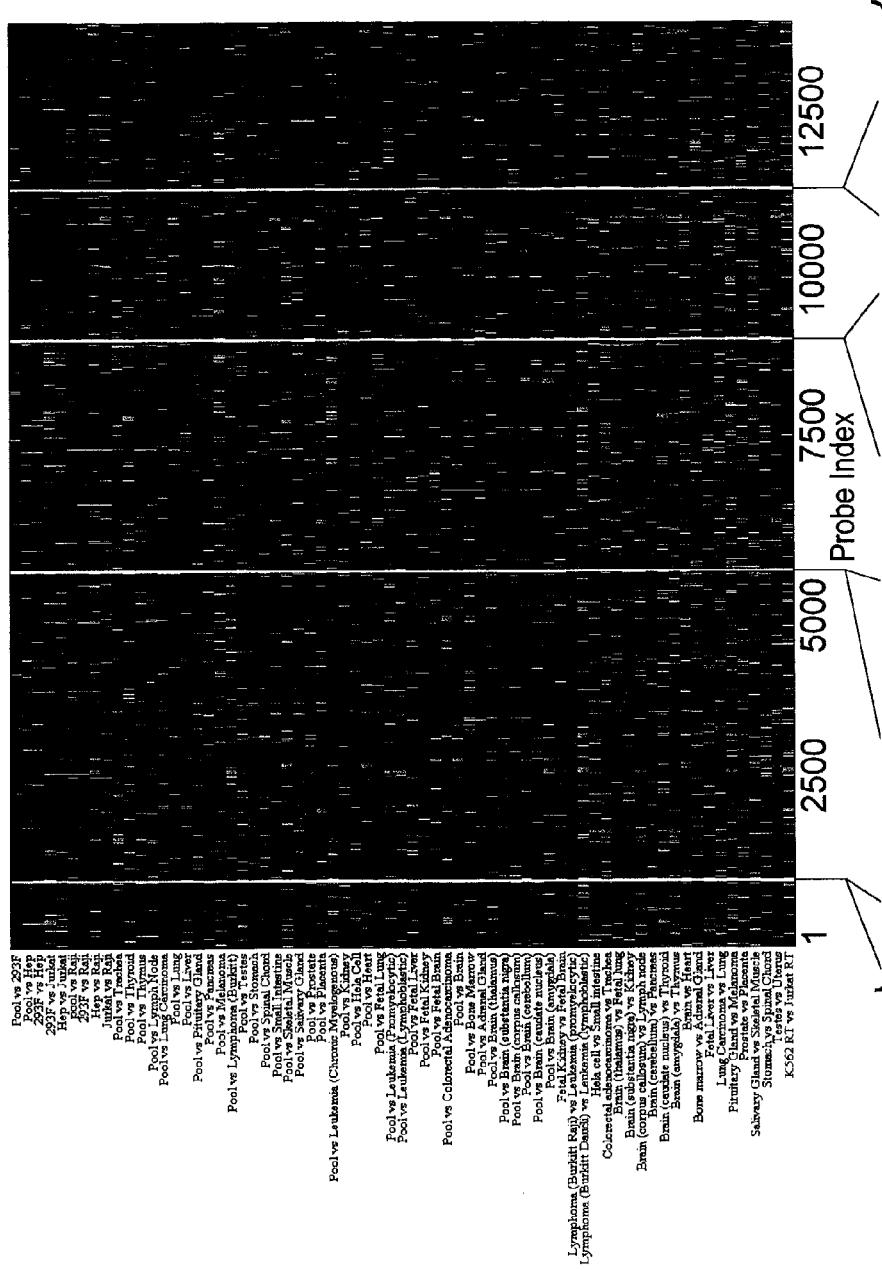

SEQUENCE LISTING

```
<160> NUMBER OF SEQ ID NOS: 3

<210> SEQ ID NO 1
<211> LENGTH: 25
<212> TYPE: DNA
<213> ORGANISM: Artificial
<220> FEATURE:
<223> OTHER INFORMATION: Description of Artificial Sequence: Primer used
      in example

<400> SEQUENCE: 1
cctatgtgac tggtcgatgc tacta                                              25

<210> SEQ ID NO 2
<211> LENGTH: 45
<212> TYPE: DNA
<213> ORGANISM: Artificial
<220> FEATURE:
<223> OTHER INFORMATION: Description of Artificial Sequence: Primer used
      in example

<400> SEQUENCE: 2
aacagtatga agagtaccaa cctatgtgac tggtcgatgc tacta                        45

<210> SEQ ID NO 3
<211> LENGTH: 60
<212> TYPE: DNA
<213> ORGANISM: Artificial
<220> FEATURE:
<223> OTHER INFORMATION: Description of Artificial Sequence: Primer used
      in example

<400> SEQUENCE: 3
tttttttttt aacagtatga agagtaccaa gtgtgcctat gtgactggtc gatgctacta        60
```

COMPOSITIONS AND METHODS FOR EXON PROFILING

This application claims benefit, under 35 U.S.C. §119(e), of U.S. Provisional Patent Application No. 60/227,902 filed on Aug. 25, 2000, and of U.S. Provisional Patent Application No. 60/227,966 filed on Aug. 25, 2000, both of which are incorporated herein by reference in their entireties.

1. FIELD OF THE INVENTION

The present invention relates to methods for analyzing exon expression profiles of a cell or type of cell. The invention also relates to nucleic acid probe arrays for determining in parallel the expression levels of a plurality of exons or multiexons for each of a plurality of genes in the genome of an organism and methods for designing and making such nucleic acid probe arrays. The invention further relates to methods for determining the effects of perturbations, such as perturbations by drugs, on exon expression and alternative RNA splicing pathways.

2. BACKGROUND OF THE INVENTION

Most prokaryotic genes are encoded by continuous DNA sequences that are not interrupted by introns. In contrast, most genes in higher eukaryotes are interrupted, i.e., protein coding sequences, the exons, are separated by noncoding, often much longer, sequences, the introns. For example, a typical mammalian gene has a size of about 16 kb with about 7-8 exons, whereas a typical mRNA has a size of only about 2.2 kb (Lewin, *Genes V*, Oxford University Press, Oxford, 1994). Protein production from such an interrupted gene involves the transcription of the entire length of such gene, including all exons and introns, into a primary transcript or pre-mRNA and the subsequent removal of the intron sequences by RNA splicing to produce a mature mRNA that encodes the protein.

In addition to alternatively spliced mRNAs derived from different combinations of exons, a number of other mechanisms may also lead to varied mRNA structures. For example, different 5' termini may be present because of multiple promoter elements. Similarly, alternative 3' processing may result in variable sites of polyA addition. Methods that can be used for detecting alternative exon splicing can also be applied for detecting these alternative mRNAs except that sequence rules for these mechanisms rather than sequence rules for splice junction sequences are used. Certain RNA editing processes could depress the hybridization signal from a genomic region. In addition, RNA trans-splicing events may join sequences encoded from unlinked genomic regions into an RNA or duplicate genomic sequences to produce enhanced signals (see e.g., Caudevilla et al., 1998, *Proc. Natl. Acad. Sci. U.S.A.* 95:12185-12190). Therefore, in eukaryotes the sequences of mRNAs do not correspond directly to genomic sequences of the genes.

The interrupted gene structure in eukaryotes offers an important mechanism for generating multiple proteins from a single gene. For example, a pre-mRNA can be spliced in different ways in a process called alternative splicing thereby allowing production of different protein isoforms with different functions from a single gene. Alternative splicing thus permits fine modulation of gene expression so that proteins can be expressed in the proper spatiotemporal context (Reyes, et al., 1991, Molecular and Cellular Biology 11:1654-1661). It is estimated that more than 35% of human mRNAs contain possible alternative splice forms (Mironov et al., 1999, Genome Research 9:1288-1293; Brett et al., 2000, FEBS Lett. 474:83-86). Alternative splicing has also been implicated in various diseases, including various cancers. For example, alternative splicing of the pre-mRNA encoding CD44 has been suggested as being important in a number of human cancers (Stickeler, et al., 1999, Oncogen 18:3574-3582).

Nuclear RNA splicing reaction, i.e., the excision of introns and ligation of exons, requires a complex nuclear machinery, the spliceosome, which is formed by a large number of splicing factors, including various proteins and ribonucleoproteins. Any variation in the relative levels of such splicing factors may affect gene expression through alternative splicing pathways. For example, it is found that overexpression of antagonistic splicing factors SF2/ASF affects alternative splicing in vivo (Caceres, et al., 1994, Science 265:1706-1709).

It is therefore of both fundamental and practical importance to monitor the expression profiles of exons, i.e., the expression levels of a plurality of exons in a plurality of genes in the genome of an organism, in cell samples, preferably on a genomic scale. On the fundamental side, this would offer an important means to link genomic sequence to protein production, and therefore phenotype. On the practical side, such exon expression profiles may be used to determined the transcriptional state of a cell or cell type. An exon expression profile and its correlation with the expression pattern of different mRNA transcripts may also be used to determine the response of a cell or cell type to external perturbations on the exon level. Therefore, there exists a need for methods for simultaneously monitoring the expression of exons of genes in a cell or a cell type. There also exists a need for methods for monitoring on the exon level the response of a cell or cell type to external perturbations.

Current methods for analysis of the expression of exons in a gene are tedious and labor-intensive. These methods, such as methods using Northern blotting and DNA sequencing, can only be applied to one single gene at a time. They are therefore not suitable for analysis of the expression of exons in a plurality of genes in a cell sample.

DNA array technologies have made it possible to monitor the expression level of a large number of genetic transcripts at any one time (see, e.g., Schena et al., 1995, *Science* 270:467-470; Lockhart et al., 1996, *Nature Biotechnology* 14:1675-1680; Blanchard et al., 1996, *Nature Biotechnology* 14:1649; Ashby et al., U.S. Pat. No. 5,569,588, issued Oct. 29, 1996). Of the two main formats of DNA arrays, spotted cDNA arrays are prepared by depositing PCR products of cDNA fragments with sizes ranging from about 0.6 to 2.4 kb, from full length cDNAs, ESTs, etc., onto a suitable surface (see, e.g., DeRisi et al., 1996, *Nature Genetics* 14:457-460; Shalon et al., 1996, *Genome Res.* 6:689-645; Schena et al., 1995, *Proc. Natl. Acad. Sci. U.S.A.* 93:10539-11286; and Duggan et al., *Nature Genetics* Supplement 21:10-14). Alternatively, high-density oligonucleotide arrays containing thousands of oligonucleotides complementary to defined sequences, at defined locations on a surface are synthesized in situ on the surface by, for example, photolithographic techniques (see, e.g., Fodor et al., 1991, *Science* 251:767-773; Pease et al., 1994, *Proc. Natl. Acad. Sci. U.S.A.* 91:5022-5026; Lockhart et al., 1996, *Nature Biotechnology* 14:1675; McGall et al., 1996, *Proc. Natl. Acad. Sci. U.S.A.* 93:13555-13560; U.S. Pat. Nos. 5,578,832; 5,556,752; 5,510,270; and 6,040,138). Methods for generating arrays using inkjet technology for in situ oligonucleotide synthesis are also known in the art (see, e.g., Blanchard, International Patent Publication WO 98/41531, published Sep. 24, 1998; Blanchard et al., 1996, *Biosensors and Bio-* electronics 11:687-690; Blanchard, 1998, in *Synthetic DNA Arrays in Genetic Engineering*, Vol. 20, J. K. Setlow, Ed., Plenum Press, New York at pages 111-123). Efforts to further increase the information capacity of DNA arrays range from further reducing feature size on DNA arrays so as to further increase the number of probes in a given surface area to sensitivity- and specificity-based probe design and selection aimed at reducing the number of redundant probes needed for the detection of each target nucleic acid thereby increasing the number of target nucleic acids monitored without increasing probe density (see, e.g., Friend et al., U.S. patent application Ser. No. 09/364,751, filed on Jul. 30, 1999, now abandoned; and Friend et al., U.S. patent application Ser. No. 09/561,487, filed on Apr. 28, 2000, now U.S. Pat. No. 7,013,221 B1).

By simultaneously monitoring tens of thousands of genes, DNA array technologies have allowed, inter alia, genome-wide analysis of mRNA expression in a cell or a cell type or any biological sample. Aided by sophisticated data management and analysis methodologies, the transcriptional state of a cell or cell type as well as changes of the transcriptional state in response to external perturbations, including but not limited to drug perturbations, can be characterized on the mRNA level (see, e.g., Stoughton et al., International Publication No. WO 00/39336, published Jul. 6, 2000; Friend et al., International Publication No. WO 00/24936, published May 4, 2000). Applications of such technologies include, for example, identification of genes which are up regulated or down regulated in various physiological states, particularly diseased states. Additional exemplary uses for DNA arrays include the analyses of members of signaling pathways, and the identification of targets for various drugs. See, e.g., Friend and Hartwell, International Publication No. WO 98/38329 (published Sep. 3, 1998); Stoughton, International Publication No. WO 99/66067 (published Dec. 23, 1999); Stoughton and Friend, International Publication No. WO 99/58708 (published Nov. 18, 1999); Friend and Stoughton, International Publication No. WO 99/59037 (published Nov. 18, 1999); Friend et al., U.S. patent application Ser. No. 09/334,328 (filed on Jun. 16, 1999, now U.S. Pat. No. 6,218,122 B1).

However, current DNA array technologies typically monitor the 3' ends of mRNA molecules in a cell, rather than the expression levels of individual exons that make up the mRNAs. For example, probes used in cDNA arrays typically range in sizes from about 0.6 to 2.4 kb (Duggan et al., *Nature Genetics* Supplement 21:10-14), and are generally complementary to the 3' ends of the mRNA molecules. Probes used in cDNA arrays are biased to the 3' end because labeling methods typically rely on d(T) primed reverse transcription. Expression analysis using high density oligonucleotide arrays has been described that requires scoring and averaging of as many as 20 oligonucleotide probes on an array, chosen from various locations of the coding sequence of a gene, to determine the transcript level of the corresponding mRNA (see, e.g., Lockhart et al., 1996, *Nature Biotechnology* 14:1675; U.S. Pat. Nos. 5,578,832; 5,556,752; 5,510,270; and 6,040,138; Lipshutz et al., 1999, *Nature Genetics* Supplement 21:20-24). Again, these probes are placed near the 3' ends of mRNA molecules and the probe intensities are averaged to a single value, and thus does not provide information of the expression of individual exons across the genes. In addition, it has been found that the majority of splicing events occurs in 5' untranslated regions, which leads to the generation of additional protein domains rather than alternating domains (Mironov et al., 1999, Genome Research 9:1288-1293). It has also been found that alternative exon-intron structures, i.e., with different end points, exist in many exons, which leads to expressed exons of different lengths (Mironov et al., 1999, Genome Research 9:1288-1293). Thus, there exists a need to design DNA arrays that measure the expression levels and the lengths of a plurality of exons for each of a plurality of genes in the genome of an organism. There exists a need for methods for quantitatively monitoring alternative splicing on a genome-wide scale.

Discussion or citation of a reference herein shall not be construed as an admission that such reference is prior art to the present invention.

3. SUMMARY OF THE INVENTION

The invention relates to compositions and methods for measurement and analysis of the exon expression profile of a cell or type of cell. The invention provides exon profiling arrays for measurement of the expression levels of a plurality of exons in each of a plurality of genes in the genome of an organism. The invention also provides methods, including data analysis algorithms, for representing and analyzing the state of a cell or cell sample and/or the response of a cell or cell sample to perturbations using exon expression profiles comprising measured expression levels of a plurality of exons for each of a plurality of genes. The compositions and methods of the invention can be used for the determination of alternative RNA splicing for a plurality of genes in the genome of an organism.

The invention relates to methods for analyzing the exon expression profile, or the exon expression state, of a cell or type of cell. In the present invention, an exon expression profile comprising a collection of measurements of the expression levels of a plurality of different exons or multiexons of each of a plurality of genes in the genome of a cell or type of cell is determined by measuring the expression levels of different individual exons or multiexons. As used herein, a multiexon refers to a nucleotide sequence spanning 2 or more neighboring exons that are a portion of the total exons present in an mRNA transcript for the corresponding gene. To determine an exon expression state, the measured expression level of each exon or multiexon within a gene is not averaged but is maintained as an individual measured value. This permits analysis of the expression of a cell sample on the exon level and is particularly useful in determining the expression of genes in which alternative RNA splicing forms containing shared exons or multiexons are analyzed. However, if desired, the measured expression levels of exons or multiexons can be averaged to determined the expression level of the corresponding mRNA. In one embodiment of the invention, the expression levels of at least 3 different exons or multiexons are measured for each gene. In another embodiment, the expression levels of at least 5 different exons or multiexons are measured for each gene. In still another embodiment, the expression levels of at least 2 different individual exons are measured for each gene. In preferred embodiments of the invention, the expression levels of all individual exons or multiexons in each of a plurality of genes are measured. In preferred embodiments of the invention, exon expression levels for at least 100, 1,000, or 10,000 different genes in the genome of the organism from which the cell sample is derived are measured to determine the exon expression profile of the cell sample.

The measured exon expression profile of a cell sample can be used as a representation of the biological state of the cell sample. Thus, the invention provides methods to represent the biological state of a cell sample by its exon expression state. Such exon expression state comprises measurements of the expression levels of a plurality of exons of a plurality of genes in the genome of an organism from which the cell sample is derived. In some embodiments, a cell sample is characterized by the collection of measurements of the identity (e.g., sequence, location in the genome, and/or length of the exon) and abundance (expression level) of individual exons or multiexons for each of a plurality of genes in a subset of genes in the cell sample, such as genes in one or more chromosomes. Thus, in some embodiments, the collection of measurements of the expression levels of individual exons or multiexons for each of a plurality of genes in a chromosome is used to identify the exon expression state of the chromosome.

In some embodiments, the measured exon expression profile is measured when a cell sample is under one or more perturbations, and, thus, represents the exon expression state of the cell sample under such one or more perturbations. In other embodiments, the exon expression state of a cell sample under one or more perturbation is determined and compared with the exon expression state of another cell sample of the same type such that the effects of the perturbations on the exon expression state of the type of cell sample can be determined.

The invention also relates to methods for determining the presence or absence of alternative spliced mRNA forms for each of a plurality of genes in a cell sample. In one embodiment, the expression levels of a set of exons or multiexons that are sufficient to determine alternative splicing pathways for each of a plurality of genes in the genome of an organism are detected or measured. The expression levels and lengths of different exons or multiexons in each such set are then used to determine the presence and relative abundance of an alternative splice mRNA form. In some embodiments, alternative splicing pathways are determined for 5 to 10 genes, preferably 10 to 100 genes, more preferably 100 to 1,000 genes, even more preferably 1,000 to 10,000 genes, most preferably more than 10,000 genes in the genome of the organism. The organism can be an animal, such as a human, a plant, such as rice, wheat, beans, and tobacco, or a fungus.

The invention also provides methods for detecting alternative splicing between two cell samples of a species of an organism. In one embodiment, the expression levels of a plurality of individual exons or multiexons in each of a plurality of different genes are detected or measured separately in a first and a second cell sample. The detected or measured expression level of each exon or multiexon in the first and second cell samples is then compared to determine alternative splicing in the first and second cell sample. Preferably the expression levels of at least 3 exons or multiexons, more preferably at least 5 exons or multiexons, most preferably all exons, in each of the plurality of genes are measured.

The invention also relates to methods for determining the relative levels of expression of individual exons in each of a plurality of genes in the genome of an organism. In one embodiment, the expression levels of at least a first exon and a second exon in each of the genes are measured. The expression levels of the first and second exon are then compared to determine the relative level of expression of the exons. In some embodiments, the relative expression levels of exons in at least 100 genes, at least 1,000 genes, or at least 10,000 genes are determined. Methods for determining the relative expression levels of more than two exons in each of a plurality of genes are also provided.

The invention also provides methods for analyzing the transcriptional state of a cell sample on an exon level. In one embodiment, the expression level of each of a plurality of exons expressed by the cell sample is detected or measured to determine the structure and abundance of different mRNAs. Preferably, the expression levels of at least 10, 100, 1,000, 10,000, or 50,000 different mRNA transcripts are measured.

The invention also provides methods for determining the effect of one or more perturbations on RNA splicing pathways in each of a plurality of genes in the genome of an organism. In one embodiment, the expression levels of a plurality of individual exons or multiexons in a first cell sample subjected to one or more perturbations are measured. The measured expression levels are then compared with the expression levels of the plurality of individual exons or multiexons in a second cell sample not subjected to the perturbations to determine the effects of the perturbations on alternative splicing pathways. Preferably, the expression levels of at least 2, 3, 5, or all of the exons in each of at least 10, 100, 1,000, 10,000, 50,000, or 100,000 different genes, or of all or the majority of genes in the genome of an organism, are measured.

The exon expression levels are preferably determined in the present invention by measuring the hybridization between RNAs or nucleic acids derived therefrom from a cell sample using a positionally-addressable exon profiling array comprising polynucleotide probes. The exon profiling array comprises a plurality of polynucleotide probes of different nucleotide sequences bound to different regions of a support, each of such different nucleotide sequences comprising a sequence complementary and hybridizable to a sequence in a different exon or multiexon of the cell sample. The expression levels of exons or multiexons are measured by contacting such exon profiling array with the RNAs or nucleic acids derived therefrom from the cell sample. In a preferred embodiment of the invention, the probes used to measure expression levels of exons or multiexons are selected such that the measured expression levels reveal one or more distinguishing structural characteristics of one or more expressed exon variants.

The invention relates to arrays of polynucleotide probes for measuring the expression levels and lengths of exons or multiexons. The arrays can comprise both exon specific probes and junction specific probes. The arrays can also comprise sets of probes for determining expressed exon variants. Such sets of probes can be sets of successive overlapping probes tiled along the longest exon variant. These types of probes are useful for determining the lengths of exons, especially on the 5' and 3' ends of transcripts. Such sets of probes can also comprise exon specific probes specifically hybridizable to common sequences among a plurality of variants of an exon and junction specific probes specifically hybridizable to different junction regions in different variants of the exon. In preferred embodiments of the invention, the exon profiling array comprises probes for measuring at least 2 different exons or multiexons for each of the genes of interests. In a preferred embodiment, the exon profiling array comprises probes for measuring at least 1000 different genes. The exon profiling array can preferably consist of at least 100, 1,000, 10,000, 50,000, 100,000, 1,000,000, or 10,000,000 different probes. The exon profiling array can have 100 to 1,000, 1,000 to 10,000, 10,000 to 50,000, or more than 50,000 different probes per 1 $cm^2$. The probes of the exon profiling array preferably consist of nucleotide sequences of no more than 1,000 nucleotides. In some embodiments, the probes of the exon profiling array consists of nucleotide sequence of 10 to 1,000 nucleotides. Preferably, the probes of the exon profiling array consists of nucleotide sequence of 15 to 600, 15 to 200, or 20 to 100 nucleotides. More preferably, the probes of the exon profiling array consists of nucleotide sequence of 40 to 80 nucleotides. Most preferably, the probes of the exon profiling array consist of nucleotide sequences of about 60 nucleotides. The array can comprise probes complementary and hybridizable to full length individual exons or multiexons. The array can comprise probes complementary and hybridizable to sequences that span the splice junction between different exons. The lengths of exons can be determined by placing probes along the entire sequence of the longest possible mRNA isoform. Such probes can be placed in large steps, e.g., at steps of 50 or 100 nucleotides arranged in either end to end or successively overlapping fashion. In some embodiments, a set of positionally-addressable arrays of polynucleotide probes, said set in total comprising for each of all known or predicted exons or multiexons in the genome of an organism at least one polynucleotide probe comprising a sequence complementary and hybridizable to a sequence in only one of said exons or multiexons is provided.

The invention also relates to methods for preparing exon profiling arrays of the present invention. In one embodiment, the arrays of the present invention are prepared by synthesizing polynucleotide probes on a support. In such an embodiment, polynucleotide probes are attached to the support covalently at either the 3' or the 5' end of the polynucleotide. In another embodiment, the arrays of the present invention are prepared by depositing polynucleotide probes on a support. The invention also provides methods for selecting polynucleotide probes for preparation of an exon profiling array, comprising (a) selecting a plurality of different polynucleotide probes for each exon or multiexon of a plurality of exons or multiexons; (b) identifying polynucleotide probes in said plurality of different polynucleotide probes for each exon or multiexon of said plurality of exons or multiexons that hybridize to their respective target nucleic acid with a specificity above a threshold specificity level; (c) ranking the identified polynucleotide probes for each exon or multiexon of said plurality of exons or multiexons according to the sensitivity and specificity with which each identified polynucleotide probe hybridizes to its respective target nucleic acid; and (d) selecting one or more different polynucleotide probes from the ranked polynucleotide probes for each exon or multiexon of said plurality of exons or multiexons.

The invention also provides computer systems and computational methods for the implementation of the methods of the present invention.

4. BRIEF DESCRIPTION OF FIGURES

FIG. 1 schematically depicts the structure of some preferred probes used in exon profiling arrays for determining the identity and measuring the expression level of exons. 101 exon 1; 102 exon 2; 103 exon 3 with 3 alternative splice junctions; 104 exon 4 with 3 alternative splice junction; 105 exon specific probe; 106 junction specific probe; 107 probe set containing tiled probes for determining splice variants; 108 probe set containing both exon specific probe and junction specific probes for determining splice variants; 109 exon array; 110 binding sites (each solid circle indicates the position at which probes of particular sequence are situated).

Figure 2:
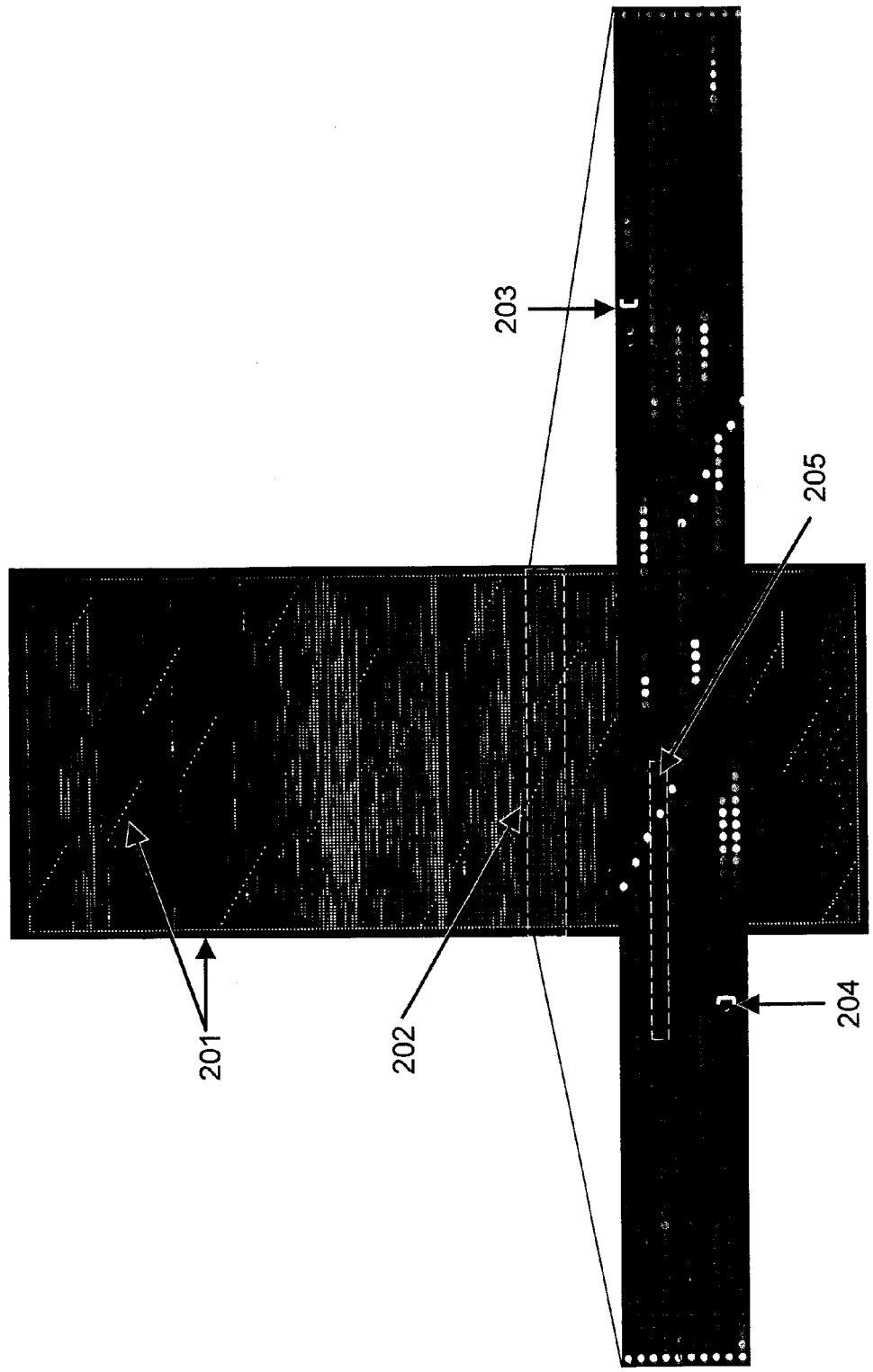

FIG. 2 depicts a scanned image of a genomic tiling array according to the present invention. The array contains 25,000 different 60-mer probes. The position of the Annexin VII gene is shown on the array in the dashed white box along with an enlargement 202. Probes comprising control sequences (201) were synthesized along the perimeter of the array, and in diagonal stripes across the array. The first 60-mer from the 5' end of the Annexin VII gene is located in the upper-right hand corner (203) of the enlargement 202, and the chosen probe sequences are tiled in overlapping 3 bp steps across the array, ending at the bottom-left hand corner (204) of the enlargement 202. 205 alternatively spiced 66 bp exon.

Figure 3:
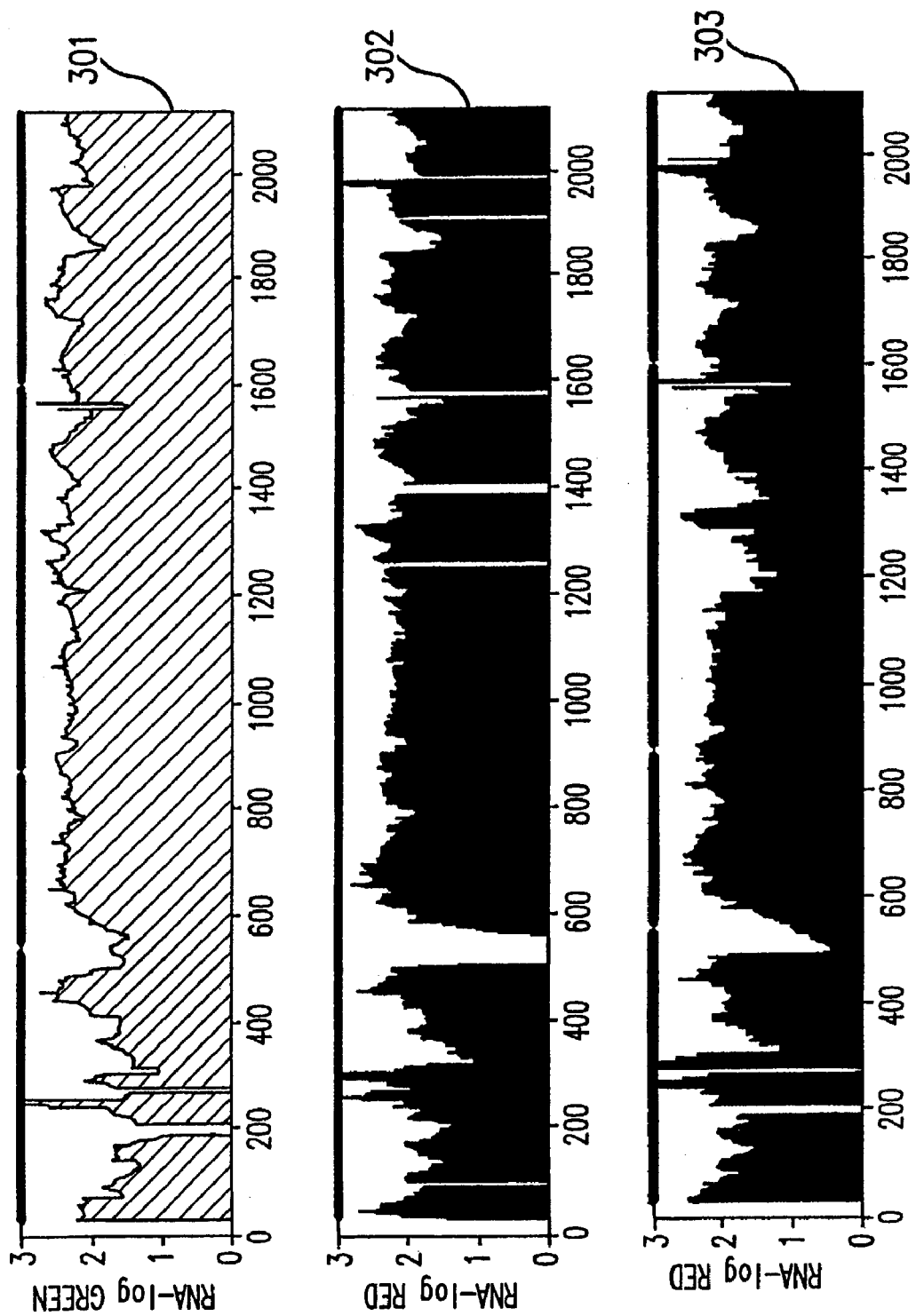

FIG. 3 depicts the exon expression level of Annexin VII gene from three cell samples: skeletal muscle (301), smooth muscle (302), and brain (303). The x-axis shows the position for each of the different 60 mers and the y-axis shows the log intensity for hybridization to each of the probes. Signal from the $6^{th}$ exon (position 495-561) is seen in skeletal muscle but is clearly missing from the smooth muscle. The data also show that the brain sample contains a mixture of the two isoforms, i.e. the long form containing the $6^{th}$ exon and the short form missing the $6^{th}$ exon.

Figure 4A:
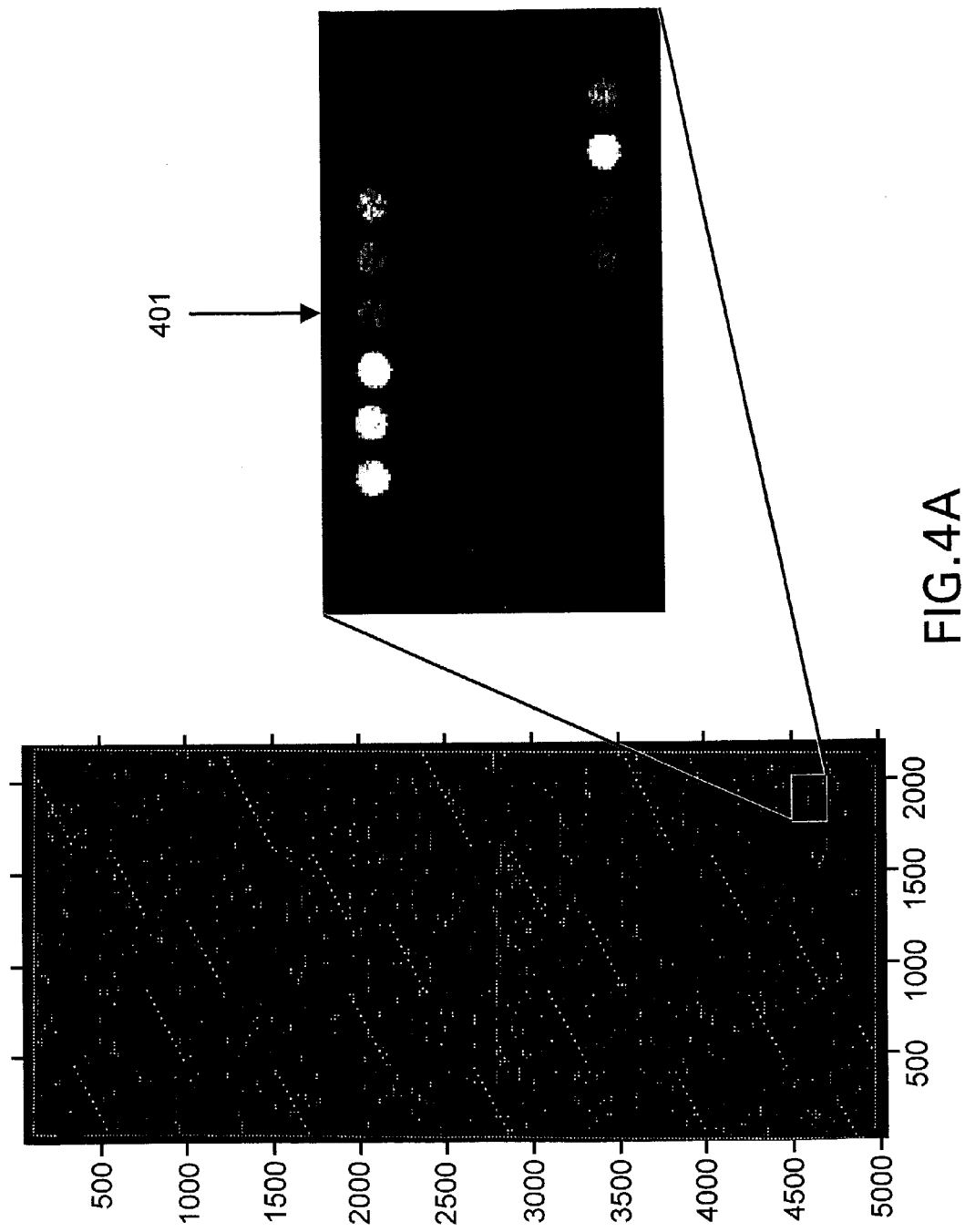
Figure 4C:
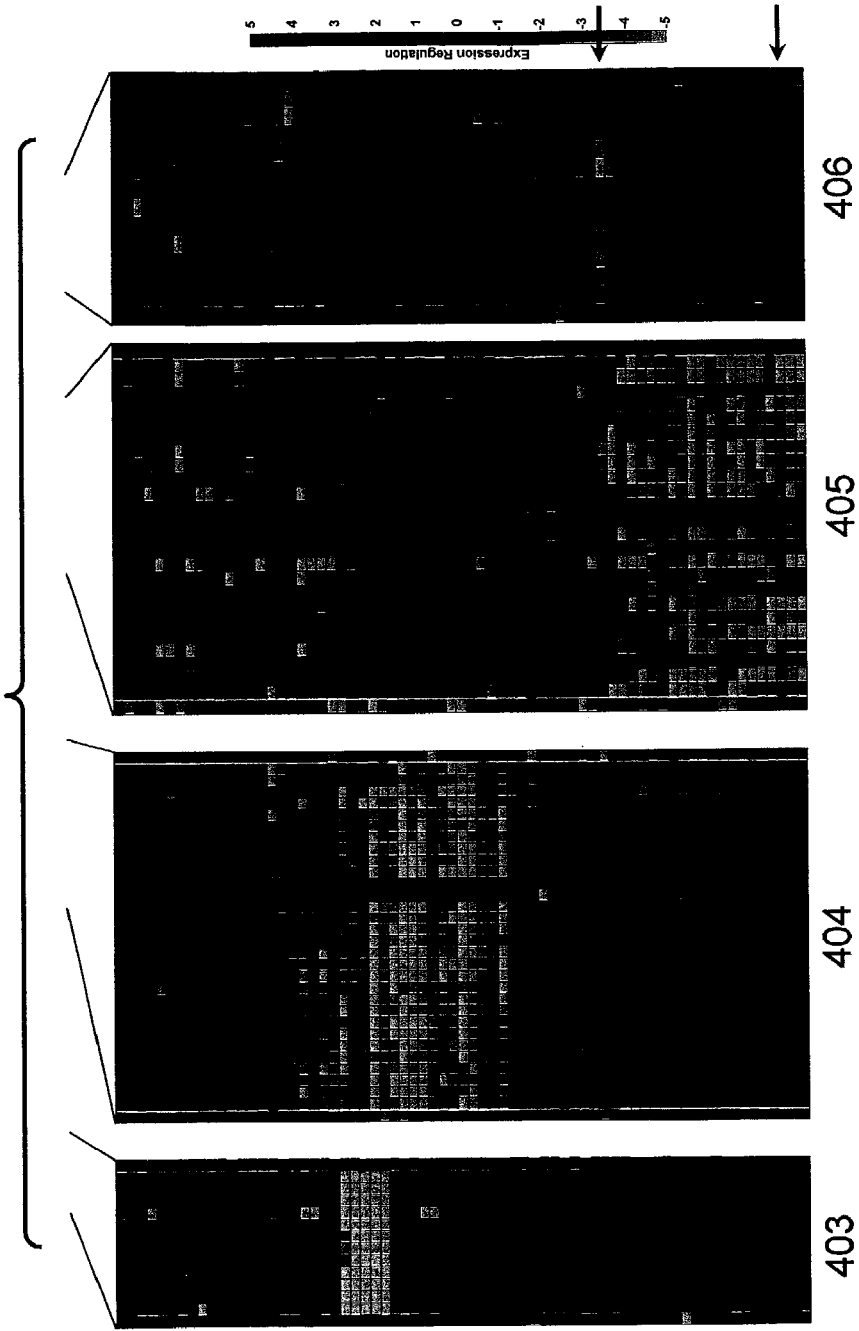

FIGS. 4a-4c depict exon profiling of human chromosome 22. FIG. 4a depicts a scanned image of the chromosome 22 exon array hybridized with labeled cDNA derived from RNA from a Jurkat cell line. The array contains 25,000 different 60-mer probes which represent 8183 exons on chromosome 22. Probes comprising control sequences as described were synthesized along the perimeter of the array, and in diagonal stripes across the array. 401 is an enlarged view showing binding sites. FIGS. 4b-4c depict using expression data from multiple conditions to validate exons and define gene boundaries on chromosome 22. 402 A grayscale version of a pseudo color image showing $\log_{10}$ expression ratios (Red/Green) for each of the exons (x-axis) across the 69 fluor reversed experiments (y-axis). The 15,511 probes representing the 8,183 predicted exons are arranged in a linear fashion across the 33 Mb of chromosome 22. The white lines indicate regions that were enlarged to show examples of specific genes. 403 Expanded region showing a known gene (SERPIND1, NM_000185). This example demonstrates how co-regulation across diverse experiments can be used to group exons into genes (the vertical white lines show the boundaries predicted by our gene finding algorithm). 404 Expanded region showing a set 13 co-regulated exons from a known gene (G22P1, NM_001469). This example demonstrates the ability to detect false positives made by the Genscan prediction program. 405 Expanded region representing an EVG (Expression Verified Gene) that collapses two Unigene EST clusters (HS.269963 and HS.14587) into a single transcript. 406 Expanded region showing an EVG containing six exons that are part of a novel transcript that is expressed in the testis (Arrows indicate the position of the two experiments involving testis RNA samples).

Figure 5:
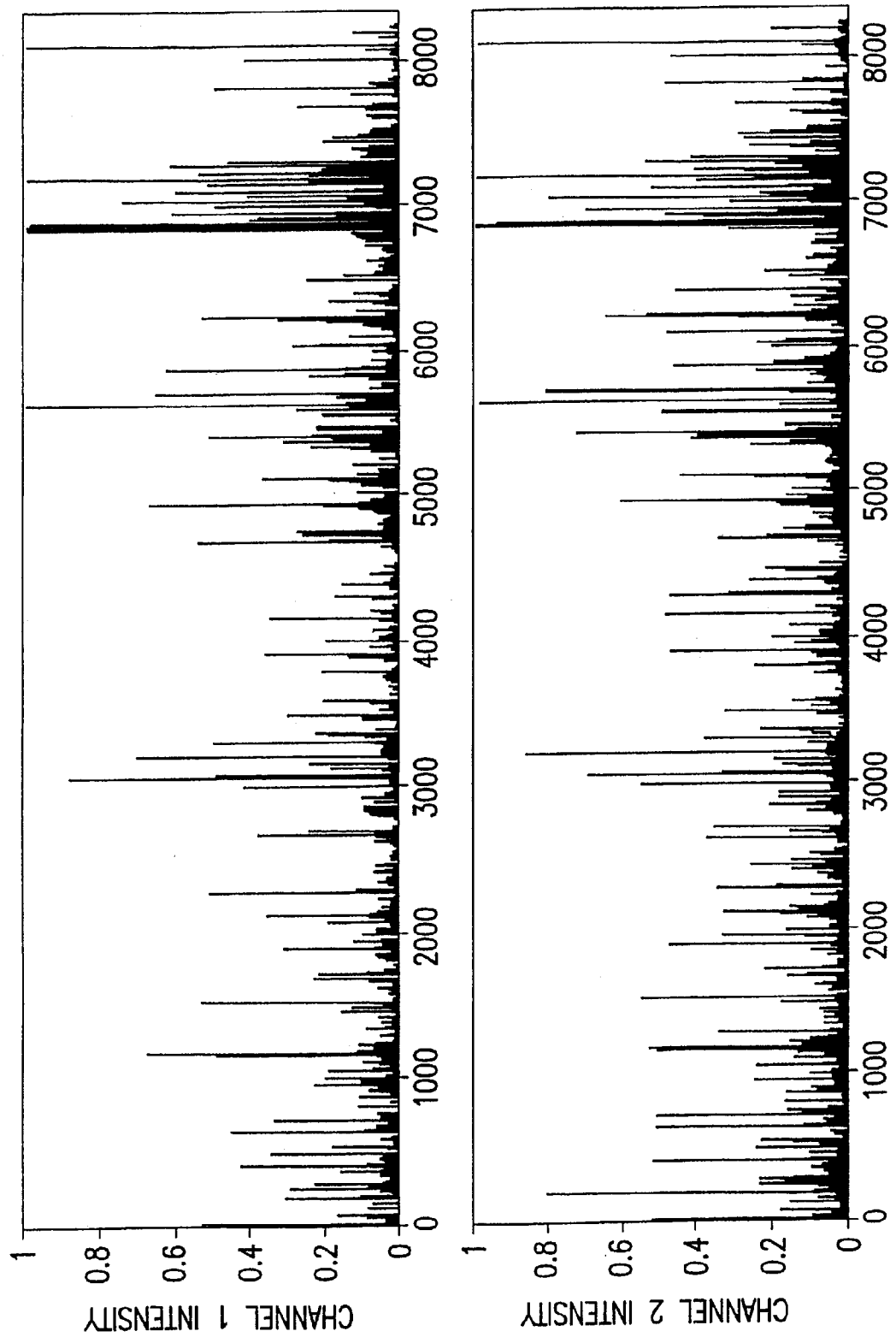

FIG. 5 depicts graphical representations of the exon expression state of human chromosome 22 measured using the chromosome 22 exon array. Channel 1 illustrates the exon expression of chromosome 22 in the Jurkat cell line; channel 2 illustrates the exon expression of chromosome 22 in the K562 cell line.

Figure 6:
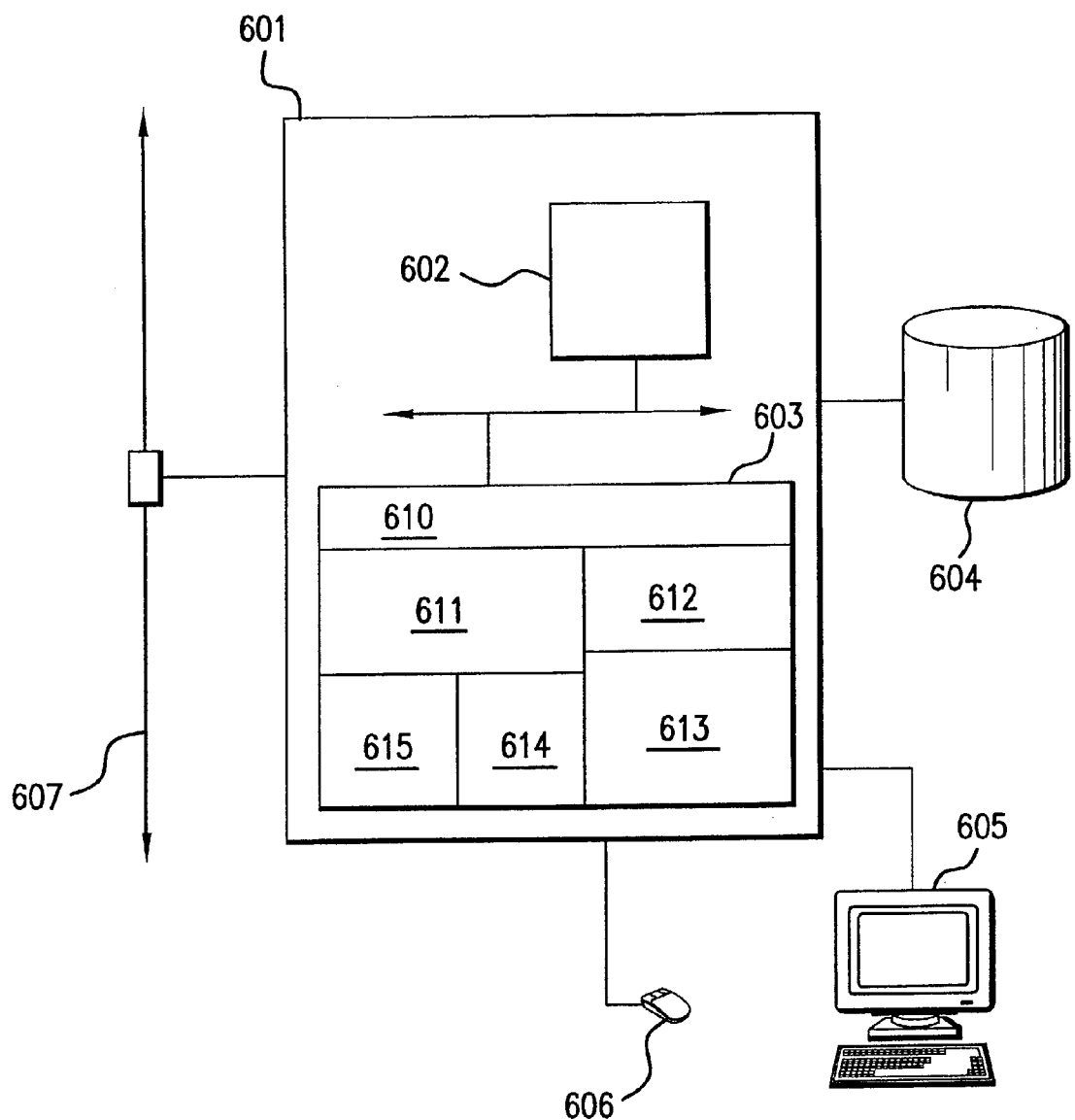

FIG. 6 illustrates an exemplary embodiment of a computer system useful for implementing the methods of this invention.

Figure 7A:
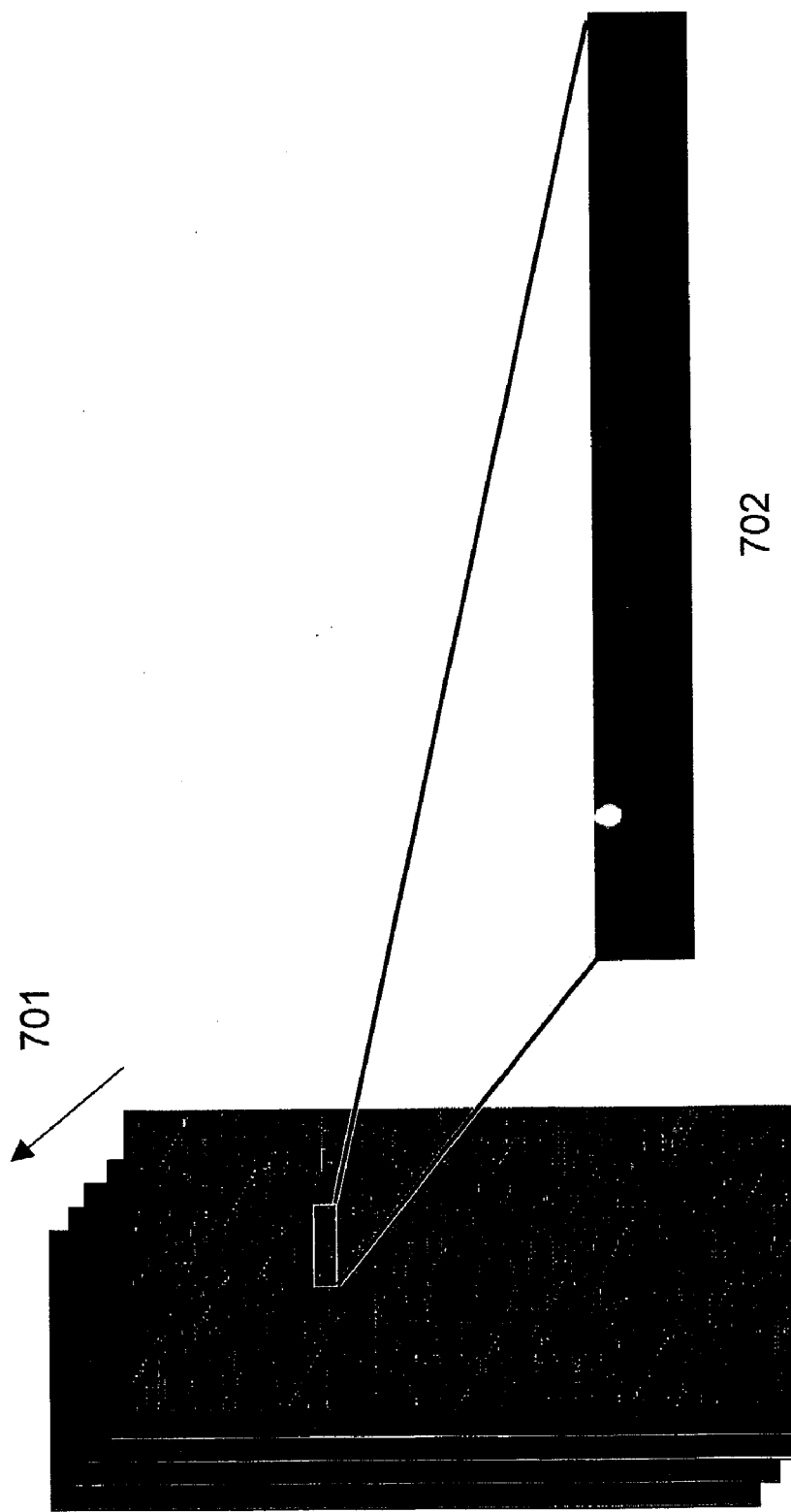
Figure 7B:
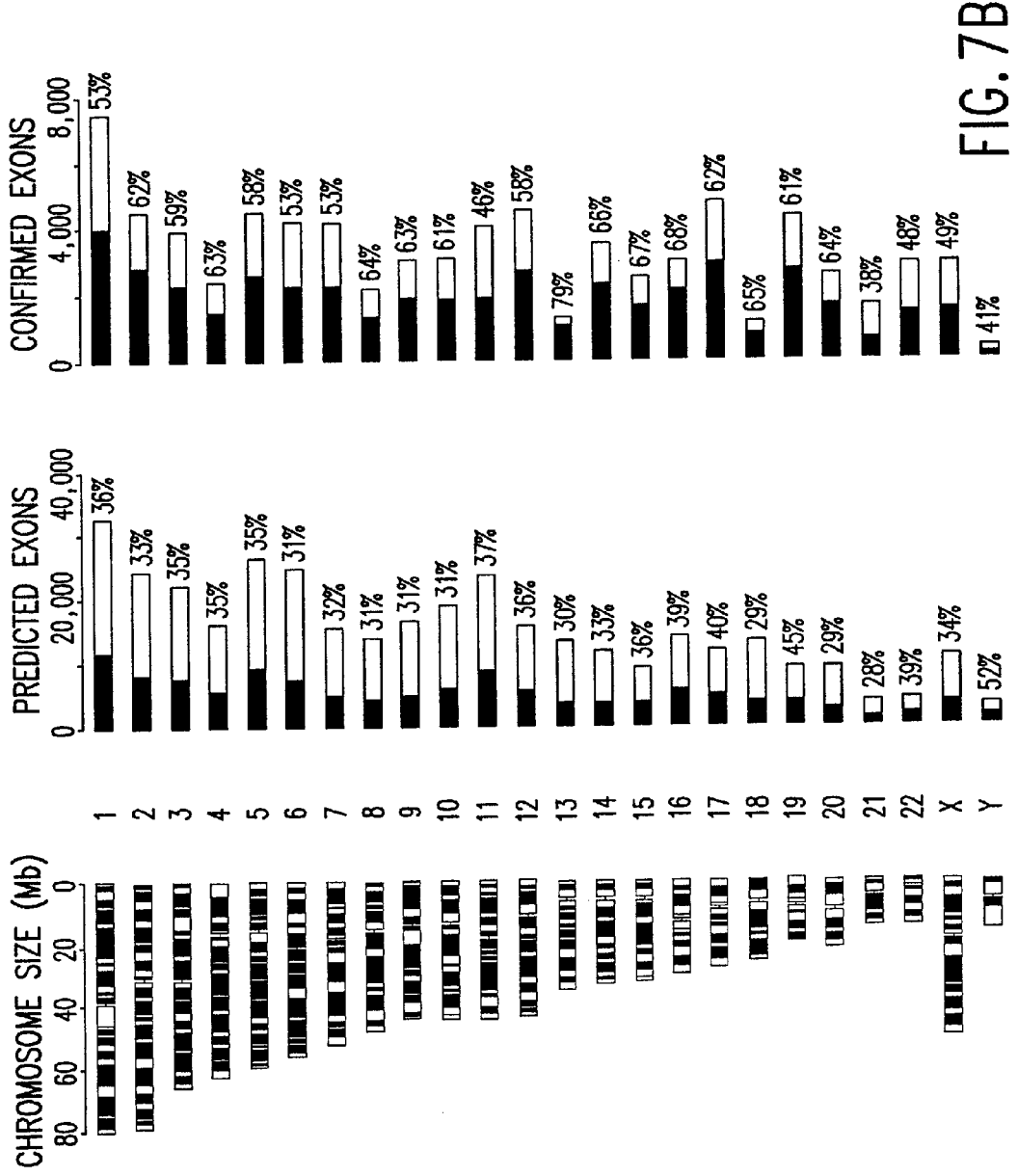

FIG. 7a-7b Whole human genome exon scan for validating predicted exons. 7a A set of 50 1×3 inch oligonucleotide arrays (701) was used to experimentally test 442,785 Genscan predicted exons as described in Methods. For each predicted exon, the best two 60 mer probes were selected resulting in the set of 1,090,408 probes which were distributed over 50 different arrays (approximately 25,000 60 mer probes per array). The arrays were hybridized with Cy-3 or Cy-5 labelled mRNA from two human cell lines (Raji and Colo). All experiments were performed in duplicate with a fluor reversal (100 arrays total). 7b The light bars show the total number of the predicted and confirmed exons across the human genome (listed by chromosome). The dark bars show the number of exons that were experimentally verified under the two conditions that were tested. 702 shows array detection of exons from a known human gene (LCP1).

5. DETAILED DESCRIPTION OF THE INVENTION

The present invention provides methods for analyzing the exon expression profile, which represents the exon expression state, of a cell or type of cell. The exon expression profile is determining by measuring the expression levels of a plurality of exons or multiexons of each of a plurality of genes in the cell or type of cell. Preferably, in determining the exon expression profile, a distinguishing structural characteristic of one or more expressed exon variants is determined. The invention also provides methods for determining the transcriptional state (measurements of the identities and abundances of individual mRNAs) of a cell or cell type using such exon expression profiles. In the present invention, the expression levels of exons or multiexons, i.e., the abundance (concentration or amount) of mRNA transcripts containing particular exons or multiexons of interest, for each of a plurality of genes are measured and are used to determine the set or sets of exons or multiexons expressed by each gene. The invention also provides DNA arrays comprising polynucleotide probes for simultaneously measuring the expression levels of a plurality of exons or multiexons in a plurality of genes and methods for determining gene expression pattern from such exon expression profiles. The invention further provides methods for measuring on the exon level the response of a cell or cell type to external perturbations or differences in expression levels of exons or multiexons between different types of cells (e.g., cells from the same species or genus but of different tissue type or developmental stage).

5.1. Biological State and Biological Response

According to the invention, a particularly useful representation of the state of a biological sample is its exon expression state. The exon expression state is represented by a collection of measurements of the abundances of individual exons expressed in mRNAs in the cell or biological sample. The state of a biological sample can also optionally be represented according to the invention by its transcriptional state. The transcriptional state is represented by a collection of measurements of the abundances of individual mRNAs in the cell or biological sample. In many organisms, especially in higher eukaryotes, the identities and abundances of mRNAs are further determined by post-transcriptional processing of pre-mRNAs via RNA splicing. Due to alternative splicing pathways, different mRNAs encoding functionally different protein isoforms can be produced at same or different tissue location and/or developmental stage from a single gene. A "gene" is referred to this application as a portion of DNA that is transcribed by RNA polymerase. Thus, a gene may include a 5' untranslated region ("UTR"), introns, exons and a 3' UTR. A gene can be a nuclear gene or an organelle gene, such as a mitochondrial or chloroplast gene. Exons are characterized by their sequences and positions in genes. Thus, two exons that differ by a single base-pair are considered different exons in this application. Two exons of identical sequence but at different locations in the genome are also considered different exons. A more complete representation of the state of a cell or cell type thus involves identifying for a plurality of genes the compositions and abundances of different mRNAs encoded in each gene by determining the exon contents and the expression levels of individual exons.

In preferred embodiments of this invention, the exon structures of a plurality of genes are obtained or determined. DNA arrays comprising probes for the detection of these exons are designed and constructed. The expression levels of the exons for each of a plurality of genes in a cell sample are then monitored using such DNA arrays. The expression profiles of exons can then be used to characterize the state, such as the exon expression state, of the sample.

Described in this section is a description of representations of biological states and biological responses in terms of genes and exons. Methods for determining the identities and abundances of mRNA transcripts from measured exon expression profiles are then provided. In subsequent sections, methods for designing and making DNA arrays for exon expression profiling and methods for determining exon expression profiles using DNA arrays are presented.

5.1.1. Exon Expression State

As used herein, the term "cell sample" is broadly defined to include any cell, tissue, organ or multicellular organism. A cell sample can be derived, for example, from cell or tissue cultures in vitro. Alternatively, a cell sample can be derived from a living organism or from a population of single cell organisms.

The state of a cell sample can be measured by the content, activities or structures of a collection of cellular constituents, which are sufficient to characterize the cell or organism for an intended purpose including, but not limited to characterizing the effects of a drug or other perturbation.

In the present invention, the state of a cell sample can be its exon expression state which is characterized by the collection of measurements of the abundance (expression level) of individual exons or multiexons for each of a plurality of genes in the genome of an organism from which the cell sample is derived. Expression level, as used herein, refers to abundance, i.e., amount or concentration. In a preferred embodiment, the determination of exon expression state comprises the determination of a distinguishing structural characteristic of one or more (or at least 2, 5, 10, 50, 100, 500, 1,000, 10,000, 50,000, or 100,000) different expressed variants of exons. As used herein, a variant of an exon refers to a particular splice form of the exon, e.g., a form of the exon generated using one of several possible 5' or 3' splice junctions. In some embodiments, the distinguishing structural characteristic (sufficient to distinguish from other variants of the same exon) of variants of exons that is determined by exon profiling may be but is not limited to the nucleotide sequence, the length or the distance between its 3' and 5' end splice junctions, or the identities of alternative splice junctions. In a preferred embodiment, the length is used to determine the identity of the expressed variant of the exon. As used herein, a multiexon refers to a nucleotide sequence spanning 2 or more neighboring exons that are a portion of the total exons present in an mRNA transcript for the corresponding gene. In a specific embodiment, a multiexon contains at least one exon of less than 50 nucleotides. Preferably, a substantial fraction of all constituent RNA species in the cell sample are measured, but at least a sufficient fraction is measured to characterize the biological state or the action of a drug or other perturbation of interest. Thus, an exon expression state of a cell sample is represented by a profile of some number of measured expression levels for a plurality of exons or multiexons in a plurality of genes. Such a profile of exon expression levels can be represented by a vector P, $$P = [P_1^1(a_1), \ldots P_1^{r_1}(a_{r_1}), \ldots P_i^{r_i}(a_{r_i}), \ldots P_k^{r_k}(a_{r_k})] \qquad (1)$$

where $P_i^{r_i}(a_{r_i})$ ($a_{r_i}=1,2,\ldots$) is the expression level of the $a_{r_i}$'th variant of the $r_1$'th exon or multiexon of the i'th gene. For example, it is believed that human genome contains about 500,000 to 1,000,000 exons for about 35,000 to 100,000 different genes. Thus, in one embodiment of the invention, P contains measured expression levels of such 500,000 to 1,000,000 exons.

In some embodiments, a cell sample is characterized by the collection of measurements of the identity and abundance (expression level) of individual exons or multiexons for each of a plurality of genes in a subset of genes in the genome of an organism from which the cell sample is derived. As non-limiting examples, the exon expression of all individual exons or multiexons for each of a plurality of genes in one or more chromosomes can be measured. Thus, in some embodiments, the collection of measurements of the expression levels of individual exons or multiexons for each of a plurality of genes in a chromosome is used to represent the exon expression state of the chromosome.

In preferred embodiments, the expression levels are measured as continuous variables. For example, the expression levels are typically measured as number of, or the concentration of, one or more mRNA molecules that contain the exon measured. The expression levels may also be measured as percentage of a control level, i.e., the expression level of one or more control probes. However, in some other embodiments, the expression levels may be measured as categorical variables. For example, the expression levels may be measured as either "on" or "off", where the value "on" indicates an expression level above a predetermined threshold and value "off" indicates an expression level below that threshold.

5.1.2. Transcriptional State

The exon expression profile can be relied upon to characterize the biological state of a cell. Optionally, the measurements of exon expression can be used to determine the forms of mRNA transcripts that are expressed and their expression levels, to provide an indication of the "transcriptional state" of the cell. The transcriptional state of a cell sample includes the identities and abundances of the constituent RNA species, especially mRNAs, in the cell under a given set of conditions. The transcriptional state of the cell sample is determined on the exon level according to the present invention, i.e., including the identities and arrangements of exons expressed in each of a plurality of genes, so that the different expression of these genes, including expressions that result in different protein isoforms via alternative RNA splicing pathways from the same gene, can be distinguished. This offers a more complete representation of the transcriptional state as compared to the traditional measurements on the 3' end mRNA level. Preferably, a plurality of exons of a substantial fraction of all constituent RNA species in the cell sample are measured, but at least a sufficient fraction is measured to characterize the biological state or the action of a drug or other perturbation of interest.

One particularly preferred embodiment of the invention employs DNA arrays for measuring exon expression levels of a large number of genes. In one embodiment of the invention, when all or a subset of all exons in a gene have substantially the same measured expression levels, the expression level of the gene is the measured expression level of any one of the expressed exons, whereas the exon content of the mRNA is the identities of the set of expressed exons. In particular, expression levels of any exons in a gene that are substantially at the background level indicate that such exons are spliced out and therefore not expressed in the mRNA. In another embodiment of the invention, when alternative splicing takes place in a gene, the measured expression levels of different exons in the gene are compared and the expression levels and exon contents of different alternatively spliced mRNAs are determined. For example, when alternative splicing takes place in a gene, one or more exons in the gene that are shared in different alternatively spliced mRNAs may have measured expression levels that are substantially higher than other exons. Such differences in measured expression levels permits identification of shared exons as well as the determination of the expression levels of different mRNAs using the expression levels of uniquely expressed exons. Other analytical and statistical methods known in the art can also be used to determine the expression levels and exon contents of different alternatively spliced mRNAs using measured expression levels of exons.

The transcriptional state of a cell sample (e.g., a cell or cell culture) can be represented by a profile of some number of gene transcript levels. Such a profile of gene transcript levels can be represented by the vector S, $$S = [S_1^1, \ldots S_1^{r_i}, \ldots S_i^{r_i}, \ldots S_k^{r_k}] \quad (2)$$

where $S_i^{r_i}$ is the transcript level of $r_i$'th mRNA, i.e., the mRNA resulted from the $r_i$'th alternative RNA splicing pathway, of the i'th gene. $S_i^{r_i}$ is obtained from a vector containing the expression levels of exons expressed in the mRNA.

Each gene can be characterized by its assembling modules, i.e., the exons. In such cases, the transcriptional state of a cell sample can be represented by exon expression profiles. For example, the transcription of gene i can be represented by an expression profile of its assembling modules, i.e., the exons, $$S_i^{r_i}(a_i^{r_i}) = [y_{i1}^{r_i}(a_{i1}^{r_i}), \ldots y_{ij}^{r_i}(a_{ij}^{r_i}), \ldots y_{im}^{r}(a_{im}^{r_i})] \quad (3)$$

where $y_{ij}^{r_i}(a_{ij}^{r_i})$ is the level of the $a_{ij}^{r_i}$'th variant of the j'th exon of gene i in the $r_i$'th RNA splicing pathway. $S_i^{r_i}$ can be determined from measured exon expression state, supra. $S_i^{r_i}$ can then be obtained from $S_i^{r_i}$ containing exon expression levels.

Although mRNA expression for a plurality of different genes in a genome is determined according to the invention from measured exon expression profiles, additionally, and optionally, expression of some mRNAs from a cell sample can be measured on the whole mRNA level using, such as mRNA based DNA array technologies. As in exon expression measurements the whole mRNA transcript levels can be measured as continuous variables. For example, the expression level are typically measured as number of, or the concentration of, the mRNA molecule. The expression level may also be measured as percentage of a control level, i.e., the expression level of one or more control probes. However, in some other embodiments, the expression levels may be measured as categorical variables. For example, the expression level may be measured as either "on" or "off", where the value "on" indicates a expression level above a predetermined threshold and value "off" indicates a expression level below that threshold.

5.1.3. Representation of Biological Responses

The responses of a cell sample to a perturbation, such as the application of a drug, can be measured by observing the changes in the biological state, e.g., the exon expression state or the transcriptional state, of the cell sample. A response profile is a collection of changes of cellular constituents, such as measured exon expression levels or measured mRNA transcript levels. In the present invention, the response profile of a cell sample (e.g., a cell or cell culture) to the perturbation m is defined as the vector $v^{(m)}$:

$$v^m = [v_1^{m,1}, \ldots v_1^{m,q_i}, \ldots v_i^{m,q_i}, \ldots v_k^{m,q_k}] \quad (4)$$

where $v_i^{m,q_i}$ is the amplitude of response of gene i in alternative splicing pathway q under the perturbation m. $v_i^{m,q_i}$ is obtained from a vector containing the response of exons expressed by the gene in the splicing pathway. In some particularly preferred embodiments of this invention, the biological response to the application of a drug, a drug candidate or any other perturbation, is measured by measuring the induced change in the expression level at least 2 genes, preferably more than 10 genes, more preferably more than 100 genes and most preferably more than 1,000 genes.

Biological responses of each gene can also be characterized by its exon components. For example, the biological response of gene i can be represented by vector, $$v_i^{m,q_i} = [b_{i1}^{m,q_i}(a_{i1}^{q_i}), \ldots b_{ij}^{m,q_i}(a_{ij}^{q_i}), \ldots b_{ip}^{m,q_i}(a_{ip}^{q_i})] \quad (5)$$

where $b_{ij}^{m,q_i}(a_{ij}^{q_i})$ ($a_{ij}^{q_i}=1,2,\ldots$) is the level of the response of the $a_{ij}^{q_i}$'th variant of the j'th exon of gene i to perturbation m in the $q_i$'th RNA splicing pathway. $v_i^{m,q_i}$ can be obtained from $v_i^{m,q_i}$ containing response measurements of exons.

In some embodiments of the invention, the response is simply the difference between the expression level of a gene or its exon components, before and after perturbation. In some preferred embodiments, the response is defined as the ratio of expression levels of a gene or its exon components before and after a perturbation is applied. In other embodiments, the response may be a function of time after the perturbation, i.e., $b_{ij}^{m,q_i}=b_{ij}^{m,q_i}(t)$. For example $b_{ij}^{m,q_i}(t)$ may be the difference or ratio of the level of the response of the j'th exon of gene i to perturbation m in the $q_i$'th RNA splicing pathway before the perturbation and at time t after the perturbation.

In preferred embodiments, $b_{ij}^{m,q_i}$ is set equal to zero for all exon j of all gene i whose responses are below a threshold amplitude or confidence level which can be determined, e.g., from knowledge of the measurement error behavior. For example, in some embodiments, only exons that have a response greater than or equal to two standard errors in more than N profiles may be selected for subsequent analysis, where the number of profiles N is selected by a user of the invention.

For those exons whose responses are above the threshold amplitude, $b_{ij}^{m,q_i}$ may be equal to the measured value. For example, in embodiments wherein the perturbation m comprises graded levels of exposure to a perturbation such as graded levels of exposure to a drug, n, $b_{ij}^{m,q_i}$ may be made equal to the expression and/or activity of the j'th exon of the i'th gene in the $q_i$'th RNA splicing pathway at the highest concentration of the drug m. Alternatively, the response at different levels of perturbations (e.g., different drug concentrations) $u_l$ may be interpolated to a smooth, piece-wise continuous function, e.g., by spline- or model-fitting, and $b_{ij}^{m,q_i}$ made equal to some parameter of the interpolation. For example, in spline-fitting the response data to various levels of the perturbation m are interpolated by summing products of an appropriate spline interpolation function S multiplied by the measured data values, as illustrated by Eq. 6:

$$b_{ij}^{m,q_i}(u) = \sum_l S(u - u_l) \times b_{ij}^{m,q_i}(u_l) \quad (6)$$

The variable "u" in Eq. 6, above, refers to an arbitrary value of the perturbation (e.g., the drug exposure level or concentration) where the perturbation response of the j'th exon of the i'th gene in the $q_i$'th RNA splicing pathway is to be evaluated.

In general, S can be any smooth, or at least piece-wise continuous, function of limited support having a width characteristic of the structure expected in the response functions. An exemplary width can be chosen to be the distance over which the response function being interpolated rises from 10% to 90% of its asymptotic value. Exemplary S function include linear and Gaussian interpolation.

In model-fitting, the response data to various levels $u_l$ of the perturbation n are interpolated by approximating the response by a single parameterized function. An exemplary model-fitting function appropriate for approximating transcriptional state data is the Hill function:

$$H(u) = \frac{a(u/u_0)^n}{1 + (u/u_0)^n} \quad (7)$$

The Hill function shown in Eq. 7, above, comprises adjustable parameters of: (1) an amplitude parameter a; (2) an exponent n; and (3) an inflection point parameter $u_0$. The adjustable parameters are selected independently for each exon. Preferably, the adjustable parameters are selected so that for each exon of the perturbation response the sum of the squared of the distances of $H(u_l)$ from $b_{ij}^{m,q_i}(u_l)$ is minimized. This preferable parameters adjustment method is well known in the art as a least squares fit of H( ) to $b_{ij}^{m,q_i}$( ). Such a fit can be done using any of the many available numerical methods known in the art (see, e.g., Press et al., 1996, *Numerical Recipes in C*, 2nd Ed., Cambridge University Press, Chpts. 10 and 14; Branch et al., 1996, *Matlab Optimization Toolbox User's Guide*, Mathworks, Natick, Mass.). The response amplitude $b_{ij}^{m,q_i}$ then be selected to be equal to, e.g., the amplitude parameter a in Eq. 7.

In an alternative embodiment, the response profile data may be categorical. For example, in a binary approximation the response amplitude $b_{ij}^{m,q_i}$ is set equal to zero if there is no significant response, and is set equal to 1 if there is a significant response. Alternatively, in a trinary approximation the response amplitude: (1) is set equal to +1 if exon q of gene i in the $q_i$'th RNA splicing pathway has a significant increase in expression or activity to perturbation n; (2) is set equal to zero if there is no significant response; and (3) is set equal to −1 if there is a significant decrease in expression or activity. Such embodiments are particularly preferred if it is known or suspected that the responses to which the response provided $b_{ij}^{m,q_i}$ is to be compared do not have the same relative amplitudes as $b_{ij}^{m,q_i}$ but do involve the same exons. In yet other embodiments, it is desirable to use "Mutual Information" as described, e.g., by Brunel (1998, *Neural Computation* 10(7): 1731-1757).

In all of the above-described embodiments, it is often preferred to normalize the response profile by scaling all elements of the vector $v^m$ (i.e., $v_i^{m,q_i}$ for all $q_i$ and i) by the same constant so that the vector length $|v^m|$ is unity. Generally, the vector length can be defined by Equation 8:

$$|v^m| = \sqrt{\sum_{i,q_i} (v_i^{m,q_i})^2} \quad (8)$$

5.1.4. Determination of Gene Expression from Exon Expression Profile

Any analytical and statistical methods known in the art can also be used to determine the expression levels and exon contents of different alternatively spliced mRNAs using measured expression levels of exons. In one embodiment of the invention, when all or a subset of all exons in a gene have substantially the same measured expression level, the expression level of the gene is the measured expression level of any one of the expressed exons, whereas the exon content of the mRNA is the identities of the set of expressed exons. In particular, expression levels of any exons in a gene that are substantially the background level indicate that such exons are spliced out and therefore not expressed in the mRNA. In another embodiment of the invention, when alternative splicing takes place in a gene, the measured expression levels of different exons in the gene are compared and the expression levels and exon contents of different alternatively spliced mRNAs are determined. For example, when alternative splicing takes place in a gene, one or more exons in the gene that are shared in different alternatively spliced mRNAs may have measured expression levels that are substantially higher than other exons. Furthermore, when the relative abundances of different alternatively spliced mRNAs are different, the measured expression levels of exons expressed in different mRNAs may be different. Such differences in measured expression levels permits identification of shared exons as well as the determination of the expression levels of different mRNAs using the expression levels of uniquely expressed exons.

When an exon has alternative splice variants, the determination of the expression of the gene containing the exon can be aided by determining some distinguishing structural characteristics (a characteristic that distinguishes a particular exon variant from other variants of the same exon), such as the length, of the expressed variant or variants of the exon. For example, a set of polynucleotide probes of successive overlapping sequences, i.e., tiled sequences, across the genomic region containing the longest known or predicted variant of an exon can be used to determine the variant or variants that are expressed. The set of polynucleotide probes can comprise successive overlapping sequences at steps of a predetermined base intervals, e.g. at steps of 1, 5, or 10 base intervals, span, or are tiled across, the genomic region containing the longest variant. Alternatively, a set of polynucleotide probes comprising exon specific probes and variant junction probes can be used to determine the variant or variants that are expressed. In a preferred embodiment, the exon specific probes are specifically hybridizable to the common sequences in all different variants of the exon, whereas the variant junction probes are specifically hybridizable to the different splice junction sequences of the exon.

In one embodiment, Expression-Verfied Genes (EVGs) are identified via co-regulation. Grouping exons into EVGs is performed using a two-step gene identification algorithm. First, each exon iss assigned a similarity measure based on taking the moving average of pair-wise correlation coefficients between neighboring exons. Exons with similarity measures above a specified threshold are selected as seeds for EVGs. Second, exons neighboring a seed region are merged into the region if the pair-wise correlation coefficients between the neighboring exon and each exon in the region exceeded the specified threshold. This process continued, allowing for gaps between exon pairs to account for failed probes and/or false exon predictions, until no exons in the immediate neighborhood of the candidate region met the significance threshold of correlation with the exon cluster. The final exon clusters resulting from the gene detection algorithm are identified as an EVG. Not all condition pairs (rows) were considered in forming EVGs. Only those that had a minimum amplitude of response of threefold at a 99% confidence level are entered into the analysis. Once an EVG was formed, the color display was updated by reordering the condition pairs according to a standard hierarchical clustering algorithm, such as the algorithm used by Hughes et al., 2000, Cell 102:109-26.

5.2. Implementation Systems and Methods

The analytical methods of the present invention can preferably be implemented using a computer system, such as the computer system described in this section, according to the following programs and methods. Such a computer system can also preferably store and manipulate a compendium of the present invention which comprises a plurality of perturbation response profiles and which can be used by a computer system in implementing the analytical methods of this invention. Accordingly, such computer systems are also considered part of the present invention.

An exemplary computer system suitable from implementing the analytic methods of this invention is illustrated in FIG. 6. Computer system 601 is illustrated here as comprising internal components and as being linked to external components. The internal components of this computer system include a processor element 602 interconnected with a main memory 603. For example, computer system 601 can be an Intel Pentium®-based processor of 200 MHZ or greater clock rate and with 32 MB or more main memory. In a preferred embodiment, computer system 601 is a cluster of a plurality of computers comprising a head "node" and eight sibling "nodes," with each node having a central processing unit ("CPU"). In addition, the cluster also comprises at least 128 MB of random access memory ("RAM") on the head node and at least 256 MB of RAM on each of the eight sibling nodes. Therefore, the computer systems of the present invention are not limited to those consisting of a single memory unit or a single processor unit.

The external components can include a mass storage 604. This mass storage can be one or more hard disks that are typically packaged together with the processor and memory. Such hard disk are typically of 1 GB or greater storage capacity and more preferably have at least 6 GB of storage capacity. For example, in a preferred embodiment, described above, wherein a computer system of the invention comprises several nodes, each node can have its own hard drive. The head node preferably has a hard drive with at least 6 GB of storage capacity whereas each sibling node preferably has a hard drive with at least 9 GB of storage capacity. A computer system of the invention can further comprise other mass storage units including, for example, one or more floppy drives, one more CD-ROM drives, one or more DVD drives or one or more DAT drives.

Other external components typically include a user interface device 605, which is most typically a monitor and a keyboard together with a graphical input device 606 such as a "mouse." The computer system is also typically linked to a network link 607 which can be, e.g., part of a local area network ("LAN") to other, local computer systems and/or part of a wide area network ("WAN"), such as the Internet, that is connected to other, remote computer systems. For example, in the preferred embodiment, discussed above, wherein the computer system comprises a plurality of nodes, each node is preferably connected to a network, preferably an NFS network, so that the nodes of the computer system communicate with each other and, optionally, with other computer systems by means of the network and can thereby share data and processing tasks with one another.

Loaded into memory during operation of such a computer system are several software components that are also shown schematically in FIG. 6. The software components comprise both software components that are standard in the art and components that are special to the present invention. These software components are typically stored on mass storage such as the hard drive 604, but can be stored on other computer readable media as well including, for example, one or more floppy disks, one or more CD-ROMs, one or more DVDs or one or more DATs. Software component 610 represents an operating system which is responsible for managing the computer system and its network interconnections. The operating system can be, for example, of the Microsoft Windows™ family such as Windows 95, Window 98, Windows NT or Windows 2000. Alternatively, the operating software can be a Macintosh operating system, a UNIX operating system or the LINUX operating system. Software components 611 comprises common languages and functions that are preferably present in the system to assist programs implementing methods specific to the present invention. Languages that can be used to program the analytic methods of the invention include, for example, C and C++, FORTRAN, PERL, HTML, JAVA, and any of the UNIX or LINUX shell command languages such as C shell script language. The methods of the invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.).

Software component 612 comprises analytic methods of the present invention, preferably programmed in a procedural language or symbolic package. For example, software component 612 preferably includes programs that cause the processor to implement steps of accepting a plurality exon expression profiles and storing the profiles in the memory. For example, the computer system can accept exon expression profiles that are manually entered by a user (e.g., by means of the user interface). More preferably, however, the programs cause the computer system to retrieve exon expression profiles from a database. Such a database can be stored on a mass storage (e.g., a hard drive) or other computer readable medium and loaded into the memory of the computer, or the compendium can be accessed by the computer system by means of the network 607.

In one embodiment, each exon expression profile (613) contained in a database and/or loaded into the memory of the computer system is represented by a data structure comprising a plurality of data fields. In particular, the data structure for a particular exon expression profile will comprise a separate data field for each exon whose measured value, e.g., expression level, is an element of the exon expression profile. The analytic software component 612 comprises programs and/or subroutines which can cause the processor to perform steps of comparing said measured expression level of said first exon to the expression level of said second exon or the measured expression levels of more than one exon in said same gene, for each of said plurality of genes. The computer then output and display the calculated differences in the measured expression levels for each first and second exon as a measure of the relative level of expression between said first and second exon.

In another embodiment, the present invention relates to a computer system for identifying alternative splicing between different cell samples, e.g., different tissues or developmental stages, with which a set of exons or multiexons is associated, comprising one or more processor units and one or more memory units connected to the one or more processor units, said one or more memory units containing one or more programs that carry out the steps of: (a) receiving a first data structure of measured expression levels of a plurality of exons or multiexons in a plurality of genes of a first cell sample and a second data structure of measured expression levels of said plurality of exons or multiexons in said plurality of genes of a second cell sample; and (b) comparing said measured expression levels of said plurality of exons or multiexons in said plurality of genes of said first cell sample to said measured expression levels of said plurality of exons or multiexons in said plurality of genes of said second cell sample. The differences in the measured expression levels of said plurality of exons or multiexons, including but are not limited to arithmetic difference, ratio, etc., in said plurality of genes between said first and second cell samples can be used to determine alternative splicing in said first and second cell samples.

In other embodiments, the data field for each exon can also contain a value representing the measured value, e.g., the expression level, of the exon in a biological sample subjecting to a particular perturbation or, more preferably, a value representing the change in the measured value of exon's expression level from an unperturbed or "wild-type" cell or sample. The exon expression profile will also comprise additional data fields that contain values describing the particular perturbation. For example, in embodiments wherein the perturbation is a genetic mutation, these fields can contain values that identify the particular gene that is mutated and/or identifier that indicates the particular cell line or strain of the cell or organism containing the genetic mutation. In embodiments wherein the perturbation comprises exposing the biological sample to one or more drugs, the fields will comprise values that identify the drug or drugs and, preferably, the dosages administered. Each exon expression profile data structure preferably further comprises one or more data fields that contain values indicating, if known, the biological activity that is associated with the perturbation and/or its profile. The data structure representing an exon expression profile can, optionally, contain other data fields as well. For example, the data structure can further comprise one or more fields whose values indicate the growth rate of a cell or organism subject to the particular modification or perturbation.

Among the exon expression profiles that can be accepted by a computer system of the present invention are exon expression profiles for modifications or perturbations to uncharacterized exons (e.g., uncharacterized genes or gene products). The analytic software component 612 preferably also comprises programs and/or subroutines which can cause the processor to perform steps of comparing exon expression profiles accepted by the computer system (e.g., the exon expression profiles) and the wild-type exon expression profiles, thereby determining the biological response of the cell sample to the perturbation. The programs further report the biological response of the cell sample to a user.

In addition to the exemplary program structures and computer systems described herein, other, alternative program structures and computer systems will be readily apparent to the skilled artisan. Such alternative systems, which do not depart from the above described computer system and pro-

5.3. Probes for Exon Expression Profiling

In the present invention, the expression levels of a plurality of exons in each of a plurality of genes in a cell sample are detected or measured using DNA probe arrays. The measured exon expression profile can optionally be used to determine the transcriptional state of the cell sample. The DNA probe arrays for exon profiling comprise probes that report the expression of a plurality of exons or the complete set of exons for a plurality of, preferably all, genes in the genome of an organism. In some embodiments of the invention, the DNA array comprises probes for at least 2, preferably at least 3, more preferably at least 5, exons or multiexons in each of the plurality of different genes. In some embodiments, to minimize the number of probes needed, the DNA array or arrays comprises probes that are complementary to a selected subset of the complete set of exons for each of a plurality of genes. Preferably, the subsets contain exons that are included in alternative splicing events. More preferably, the subsets contain exons that are included in alternative splicing events that result in phenotypes of interest. Where only a subset of exons for a gene is reported in the DNA arrays, it may be desirable to include a plurality of or all exons that are not constitutively spliced in all alternative splicing pathways, while including only one exon per group of such constitutively spliced exons. However, it may also be useful to include more than one exon per group of such constitutively spliced exons for redundancy purposes.

The DNA array or set of arrays can comprise at least 1, 5, 20, 50, 100, 1,000, 10,000, 100,000, 1,000,000, 5,000,000, or 10,000,000 probes complementary to sequences contained entirely within individual exons. Such probes are termed "exon specific probes." In another specific embodiment, the DNA array or set of arrays can comprise at least 1, 5, 20, 50, 100, 1,000, 10,000, 100,000, or 1,000,000 probes that are complementary to sequences spanning the junction regions of multiexons. Such probes are termed "junction specific probes." A DNA array or set of arrays comprising both exon specific probes and junction specific probes is also envisioned. Alternatively or additionally, the DNA array or set of arrays can comprise probes that tile across full length multiexons. Such probes are useful in distinguishing alternative splicing pathways and/or expression of duplicated exons in separate genes if the ligated multiexon occurs in one or more alternative spliced mRNAs and/or one or more separated genes that contain the duplicated exons but not in other alternatively spliced mRNAs and/or other genes that contain the duplicated exons. Preferably, the DNA array comprises probes for a sufficient set of exons or multiexons in each gene so that a plurality of alternative splicing pathways can be determined. DNA array or set of arrays comprising probes tiled along the full length coding sequence, i.e., all exons, can also be used for distinguishing alternative splicing.

It may also be useful to include probes that are complementary to introns in the probe set for at least some genes. In some embodiments, such intron specific probes are used to detect intron retention through genomic contamination or incomplete/incorrect slicing. In other embodiments, introns can be included in the probe set as reference probes, such as control probes for a null signal. In such cases, an intron that is not adjacent to an exon that may also have a null expression level is normally chosen. Because introns may contain repetitive sequences, intron probes are preferably selected such that repetitive sequences are avoided. When desired, the DNA array or arrays can also comprise probes for only exons. For example, the DNA array or arrays can comprise probes that target all individual exons of a gene. Or the DNA array or arrays can comprise probes that target a selected subset of exons of a gene. In a preferred embodiment, the DNA arrays permit measurement of the expression levels of all of the exons in a gene for all of the genes in the genome of an organism.

5.3.1. Determination of Exon/Intron Structures for Genes

The polynucleotide probes on the arrays of the invention comprise a plurality of different probes, each comprising a nucleotide sequence complementary and hybridizable to the sequence of a different exon or multiexon in the genome of an organism. Any method known in the art can be used to determine exon sequences of a genome so as to design the complementary sequences of the probes.

The complete or partial exon structures and thus exon sequences for many genes in a variety of organisms are known in the art. For example, exon structures and sequences for at least 2,000 human genes are known. Furthermore, predicted exon structures for about 600,000 exons are also available from the rough draft of the human genome reference ensembl database. For unknown genes or known genes whose exon structures are unknown or only partially known, such structures can be determined by various methods known in the art. The methods for identifying genes and gene structures make use of the genomic sequence data, the protein sequence data or the corresponding mRNA sequence data, and computational sequence analysis tools to identify the coding regions in the genome of an organism. With the completion or near completion of sequencing and annotation of the genomes of a wide range of organisms, including human, and the large collection of cDNA libraries, the exon structures and sequences of many genes in the genomes of many organism can be obtained. Thus, in a preferred embodiment, probes can be designed for genome-wide exon profiling according to the present invention.

For example, the sequences of exons and introns encoded in a gene can be obtained by comparing the expressed mRNA sequences or cDNA derived therefrom to the genomic sequence of the organism using the SIM4 computer program (see Florea et al., 1998, Genome Res. 8:967-974; available at http://pbil.univ-lyon1.fr/sim4.html). Sequence alignment of the coding sequences of the mRNA and the genomic sequence of the organism using any of the known methods can be used to identify the exons and introns in the gene. For example, the sequence of cDNAs, either full length cDNAs or ESTs, known in the art can be compared to genomic sequence of the same species to identify splice junctions and thus exon/intron in such manner. The exon structures of genes can also be determined by scanning the genome of an organism or region of the genome using DNA arrays comprising polynucleotide probes tiled across the genome or genomic regions. Further descriptions of such methods that can be used to determine the sequences of exons are described herein below.

For the identification of exons in nuclear genes, sequence alignment of coding regions can also be aided by the conserved intron/exon junction sequences. Although there is no extensive homology or complementarity between the two ends of an intron, an intron/exon junction normally have well-conserved sequences. In particular, as one simple rule, for most eukaryotic nuclear genes, i.e., excluding introns in the nucleic acids in mitochondria and chloroplasts and the yeast tRNA, the splice junction sequences comply to the so called GT-AG rule, i.e., an intron starts with the dinucleotide GT and ends with the dinucleotide AG. The exon structure of a nuclear gene can therefore be determined by aligning the sequence of the gene according to both the coding sequences from mRNA(s) and such conserved junction sequences. It is also worth noting that the splice junction sequences are asymmetric in regard to the 5' and 3' splice junctions thereby allowing distinguishing the direction of an intron sequence. Longer, species-specific, consensus splice junction sequences can also be used (Ohshima, et al., 1987, J. Mol. Biol. 195:247-259). Other sequences known in the art that may be advantageously employed for accurate identification of exons and introns in a gene can also be used in conjunction with the present invention.

In some embodiments of the present invention, at least a sufficient subsequence for each of at least a subset of the exons for each gene is identified. Preferably the subset of exons for each gene whose subsequences are identified is sufficient for the characterization of all alternative splicing pathways. More preferably, at least a sufficient subsequence for each of some introns is also identified. Still more preferably, at least a sufficient subsequence of the complete set of exons and introns for each gene is identified.

Preferably, the accurate and complete sequence of an exon is known. However, exon prediction means can also be used to provide sequence information for unknown exons. Such predicted sequence may or may not be definitive or complete. For example, in certain cases the determination of the precise boundary between an exon and an intron is still a difficult task. Under certain conditions, such precise determination of exon boundary may not be necessary in that the probe sequence for an exon can be selected from the more reliably determined portion of the coding sequence. The predicted exon structure may also incorrectly misidentify one or more exons for a gene, incorrectly split a gene, i.e., exons of one gene are split into multiple genes, or incorrectly join certain genes, i.e., exons from different genes are assembled into a single gene. Avoidance of such inaccuracies in exon structure is preferred in designing the probes of the invention, but is not necessary since signal noise and/or artefacts due to such inaccuracies should not significantly impair the ability to obtain useful exon profiling information.

5.3.1.1. From Genomic Sequence and cDNA Sequence

When sequence information of the mRNAs encoded by a gene with unknown structure is available, e.g., via cDNAs or ESTs, the exon structure can be identified by sequence alignment of such cDNA or EST sequences to the available genomic sequence of the organism. There are large database collections of cDNAs and ESTs for a variety of organisms, which can be used for gene structure identification. For example, one such database is the UniGene database system which automatically partitions GenBank sequences (currently containing sequence collections of human, mouse, rat, and zebrafish), including both well-characterized genes and EST sequences into a non-redundant set of gene-oriented clusters. Each UniGene cluster contains sequences that represent a unique gene, as well as related information such as the tissue types in which the gene has been expressed and location (http://ncbi.nlm.nih.gov/UniGene). Currently, the UniGene database contains a total of 1,942,605 mRNA and EST sequences catalogued into a total of 83,945 clusters for human alone (statistics uploaded on Sep. 29, 2000). Other public accessible and commercial databases of cDNAs and ESTs for a wide range of organisms are also available. On the other hand, genome sequencing for a wide range of organisms, including human, are completed or nearly completed. Therefore, the exon structures of genes in addition to those known can be identified. By comparing mRNA and EST sequences with genomic sequence, intron sequences can also be identified.

Any sequence alignment tools can be used in the present invention. In preferred embodiments, sequence alignment is performed by means of a BLAST or PowerBLAST algorithm (Altschul et al., 1990, J. Mol. Biol. 215:403-410).

5.3.1.2. Software Prediction from Genomic Sequence

Exons and exon/intron boundaries can also be identified in the genomic sequence of an organism using various computational gene prediction programs known in the art, such as GeneParser (Snyder, et al., Nucl. Acids Res. 21:607-613), GRAIL (Uberbacher, et al., 1991, Proc. Natl. Acad. Sci. USA 88:11261-11265), SYBCOD (Rogozin, et al., 1999, Gene 226:129-137), GeneID (Guigo, et al., 1992, J. Mol. Biol. 226:141-157), GREAT (Gelfand, 1990, Nucleic Acids Res. 18:5865-5869; Gelfand, et al., 1993, Biosystems 30:173-182.), GenLang (Dong, et al., 1994, Genomics 23:540-551), FGENEH (Solovyev, et al., 1994, Nucleic Acids Res. 22:5156-5163), and SORFIND (Hutchinson, et al., 1992, Nucleic Acids Res. 20:3453-3462).

Such computational gene structure prediction tools rely on various computational methodologies and algorithms and make use of the large ensemble of knowledge and databases on sequence characteristics of nucleic acid and protein sequences to determine the sequences and locations of genes as well as the structures of genes in available genomic sequences. For example, in GeneParser, the genomic sequence can be scored for codon usage, local compositional complexity, 6-tuple frequency, length distribution, periodic asymmetry, as well as splice junction sequences. The identification and prediction of gene structure can also be carried out using coding sequence homology to known genes in existing DNA and protein databases (Altschul et al., 1990, J. Mol. Biol. 215:403-410). Other methods, such as SYNCOD, allow identification and prediction of new genes that do not have good homology with known protein sequences.

Any one of the gene prediction methods can be used either alone or in combination with any other method or methods for the identification of exon structures of genes from genomic sequences. Each of the methods has its strength and weakness in exon prediction accuracy (see, e.g., Burset, et al., 1996, Genomics 34:353-367; Reese, et al., 2000, Genome Res. 10:483-501). It is therefore preferred to use a combination of at least a number of methods so that prediction inaccuracies, such as missed exons and/or wrong exons, of one method can be detected and remedied. In embodiments of the present invention, preferably at least 2, more preferably at least 3, most preferably all different methods are used so that a consensus exon structure can be obtained. In most preferred embodiments, the results obtained by using such computational tools are further aided with biological knowledge about the organism so that more accurate exon structure for a gene or genes can be obtained.

5.3.1.3. Exon Identification Using DNA Arrays

In another embodiment, exons can be identified by using DNA arrays that contain polynucleotide probes of successive overlapping sequences, i.e., tiled sequences, across genomic regions. See, e.g., U.S. provisional patent application Ser. No. 60/227,966, filed on Aug. 25, 2000, which is incorporated herein by reference in its entirety. Such DNA arrays therefore scan the genomic regions to identify expressed exons in these regions. According to the method, DNA arrays are generated comprising polynucleotide probes with successive overlapping sequences which span or are tiled across genomic regions of interests, e.g., successive overlapping probe sequences can be tiled at steps of a predetermined base intervals, e.g. at steps of 1, 5, 10, or 15 base intervals. The overlapping sequences of the DNA arrays therefore comprise probes for both exons and introns. For example, DNA arrays comprising 25,000 different polynucleotide probes of up to 60 bases in length can be synthesized on a single 1×3 inch glass slide by ink-jet technology. RNA samples from diverse tissues or growth conditions are then labeled using full length labeling protocols, such as the random primed reverse transcription protocols and hybridized to the DNA arrays. Exons and exon/intron boundaries can be identified by positive hybridization signals (i.e., signals above background noise and/or cross-hybridization signal levels) which can be obtained by e.g. absolute signal, change in signal with change in growth condition, and/or comparison of the signals from the complementary strands. In particular, the exon/intron boundaries can be identified by the transition of positive signals to negative signals across sets of overlapping probes representing the covered genomic regions.

5.3.1.4. Combined Approaches

According to the present invention, any methods as described in Sections 5.3.1.1-5.3.1.3 can be used either alone or in combination with any other methods in order to determine exon structures and sequences. One skill in the art will be able to determine which method or combination of methods are to be used for the identification of the structure of a particular gene or genes based on such factors as the availability of mRNA and/or EST sequence(s), its homology to protein(s) encoded in known genes, and so on. In some embodiments of the invention, several methods may be used in combination with each identifying a different subsets of exons for the same gene. In other embodiments of the invention, several methods can be used with each method identifying the entire structure of the gene and the results are compared so that a more accurate structure can be obtained.

5.3.2. Selection of Probe Sequences

In preferred embodiments of the invention, a DNA array or set of arrays comprises polynucleotide probes comprising predetermined sequences that are selected or designed for detection of exons or multiexons. Probe sequences for an exon or multiexon can preferably be selected from the sequence of the exon or multiexon according to other parameters including, but not limited to any combination of one or more of: (a) probe size or length; (b) binding energies, including both the perfect match duplex (i.e., of a probe and its target, complementary nucleotide sequence) and cross-hybridization binding energies; (c) base composition, including, for example, the relative amount or percentage of one or more particular nucleotide bases (e.g., adenine, guanine, thymine or cytosine) in a probe sequence, as well as the relative amount or percentage of any combination of such nucleotide bases; (d) the position of a probe's complementary sequence in the sequence of its "target" polynucleotide or gene sequence; and (e) probe sequence complexity, including the presence or lack of common repetitive elements such as polynucleotide repeats (i.e., simple, contiguous repeats of one or more nucleotide bases) as well as more complicated repetitive elements that are well known in the art. Still other exemplary parameters which can be used in the methods and compositions of the invention for ranking and/or selecting polynucleotide probes include: (f) self dimer binding energy (i.e., the tendency for a particular probe to hybridize to its own sequence); (g) the structure content of the complementary, target polynucleotide sequence for a particular probe (e.g., the presence or absence of certain structural features or motifs); and (h) the information content of a probe's nucleotide sequence. See, e.g., Friend et al., U.S. patent application Ser. No. 09/561,487 (filed on Apr. 28, 2000, now U.S. Pat. No. 7,013,221 B1); Friend et al., U.S. patent application Ser. No. 09/364,751 (filed on Jul. 30, 1999, now abandoned); Burchard, U.S. patent application Ser. No. 09/616,849 (filed on Jul. 14, 2000, now U.S. Pat. No. 7,371,516 B1).

Methods for probe selection are based, at least in part, on the discovery that the number of probe sequences required to reliably and accurately report a particular polynucleotide sequence, such as the sequence of a particular gene, may be reduced to as few as one probe by carefully selecting probes according to the methods and/or having the particular lengths disclosed herein. Accordingly, the invention also provides methods by which probes (i.e., probe sequences) may be ranked and/or selected according to their reporting properties, including, for example, their specificity and sensitivity for a particular sequence (e.g., for the sequence of a particular gene or gene transcript).

The invention thus provides methods for selecting one or more different polynucleotide probes from a plurality of possible polynucleotide probes for a given exon sequence according to the predicted sensitivity and specificity with which each different polynucleotide probe hybridizes to a target polynucleotide. As used herein, the "sensitivity" of a probe refers to the fraction of molecules of the probe that hybridize to polynucleotide molecules (or that have polynucleotide molecules hybridized thereto) under a particular set of hybridization conditions (e.g., the selected or provided hybridization conditions). The "specificity" of a probe, as used herein, is understood to refer to the ratio of target (e.g., perfect match) polynucleotide molecules to non-target polynucleotide molecules hybridized to the probe under a particular set of hybridization conditions (e.g., the selected or provided hybridization conditions). In one embodiment, the methods comprise: (a) identifying a plurality of different polynucleotide probes in a sequence region of interest in a given exon that hybridize to the target polynucleotide with a sensitivity above a threshold sensitivity level; (b) ranking the identified polynucleotide probes according to the specificity and sensitivity with which each identified polynucleotide probe hybridizes to the target polynucleotide; and (c) selecting one or more different polynucleotide probes from the ranked polynucleotide probes to represent the exon on the array. In another embodiment, the methods comprise: (a) identifying polynucleotide probes in the plurality of different polynucleotide probes that hybridize to the target polynucleotide with a predicted specificity above a threshold specificity level; (b) ranking the identified polynucleotide probes according to the sensitivity with which each identified polynucleotide probe hybridizes to the target polynucleotide; and (c) selecting one or more different polynucleotide probes from the ranked polynucleotide probes. In still another embodiment, the methods comprise: (a) ranking the plurality of different polynucleotide probes according to the sensitivity with which each polynucleotide probe hybridizes to the target polynucleotide so that a sensitivity rank is obtained for each different polynucleotide probe; (b) ranking the plurality of different polynucleotide probes according to the specificity with which each polynucleotide probe hybridizes to the target polynucleotide so that a specificity rank is obtained for each different polynucleotide probe; (c) obtaining a combined rank for each different polynucleotide probe, wherein the combined rank is determined by determining the sum of the sensitivity rank and the specificity rank for each different polynucleotide probe; and (d) selecting one or more different polynucleotide probes from the plurality of different polynucleotide probes according to the combined rank of the different polynucleotide probes. In one aspect of this particular embodiment, the sum of the sensitivity rank and the specificity rank for each different polynucleotide probe can be, e.g., a weighted sum of the sensitivity rank and the specificity rank for each different polynucleotide probe.

The invention provides numerous different aspects of these different embodiments. for example, the invention provides aspects of the above embodiments wherein the sensitivity with which a particular polynucleotide probe hybridizes to the target is provided by determining the binding energy with which the target polynucleotide hybridizes to the particular polynucleotide probe, e.g., according to the nearest neighbor model. The invention also provides aspects of the above embodiments wherein the sensitivity with which a particular polynucleotide probe hybridizes to the target polynucleotide is provided by a method comprising determining the level of hybridization of the target polynucleotide sequence to the particular polynucleotide probe; e.g., by calculating the level of hybridization of the target polynucleotide to the polynucleotide probe from the binding energy with which the target polynucleotide hybridizes to the particular polynucleotide probe.

In another aspect of the methods of the invention, the specificity with which a particular polynucleotide probe hybridizes to the target polynucleotide is provided, e.g., by: (a) determining the level of hybridization of the target polynucleotide to the particular polynucleotide probe; and (b) determining the level of cross-hybridization of non-target polynucleotides to the particular probe.

In still other embodiments, the methods of the invention comprise: (a) hybridizing a reference polynucleotide sample comprising molecules of the target polynucleotide to the plurality of different polynucleotide probes under conditions such that the hybridization intensity of each different polynucleotide probe to the reference sample correlates with the sensitivity and specificity with which the each different polynucleotide probe hybridizes to the target polynucleotide; and (b) selecting polynucleotide probes in the plurality of different polynucleotide probes that have the highest hybridization intensity. For example, the invention provides particular aspects of this embodiment wherein the hybridization is within 5° C. or within 2° C. of the mean melting temperature of the plurality of different polynucleotide probes from the target polynucleotide.

The invention also provides a preferred embodiment wherein the specificity of a particular polynucleotide probe is provided by a method which comprises selecting, from a plurality of binding energies, a binding energy that indicates the specificity of the particular polynucleotide probe. Specifically, in such a preferred embodiment, the provided plurality of binding energies are binding energies for hybridization of the particular polynucleotide probe to each of a plurality of different polynucleotides, wherein each polynucleotide in the plurality of different polynucleotides is different from the target polynucleotide. The selected binding energy is the largest binding energy in the plurality of binding energies.

For example, in one aspect of this preferred embodiment, the binding energies provided for hybridization of the particular polynucleotide probe to each of the plurality of polynucleotides is provided according to a nearest neighbor model. In one aspect the plurality of polynucleotides comprise polynucleotides expressed by a cell or organism of interest. In one aspect, the plurality of polynucleotides consists of polynucleotides having sequences with a selected level of identity or homology to a complementary sequence of the particular polynucleotide probe. For example, in one aspect, the sequences having the selected level of identity or homology to the complementary sequence of the probe are identified by means of a BLAST or PowerBLAST algorithm. In various aspects, the plurality of polynucleotides consists of polynucleotides having sequences that are at least 50%, at least 60%, at least 70%, at least 80%, at least 90%, at least 95% or at least 99% identical to the complementary sequence of the particular polynucleotide probe.

In still other embodiments, which are both more general and more preferred embodiments, the polynucleotide or oligonucleotide probes are ranked and/or selected according to a combination of two or more of the properties (a)-(h) listed above and, optionally, the sensitivity and/or specificity with which each probe hybridizes to a target polynucleotide. For example, in one embodiment the invention provides methods for selecting one or more different polynucleotide probes from a plurality of polynucleotide probes be a method comprising: (a) identifying those polynucleotide probes in the plurality of polynucleotide probes that have particular values (or a particular range of values) of one, two, three or more properties or parameters (e.g., selected among the properties and parameters listed hereinabove); and (b) selecting the polynucleotide probes identified in step (a).

In another general embodiment, the methods of the invention comprise: (a) ranking the polynucleotide probes in a plurality of different polynucleotide probes according to each of two or more selected properties or parameters (e.g., selected from the properties and parameters recited hereinabove) so that a rank is obtained for each of the two or more selected parameters; and (b) obtaining a combined rank for each different polynucleotide probe, wherein the combined rank is determined from the sum of the ranks obtained for each of the two or more selected properties or parameters. One or more different polynucleotide probes can then be selected from the plurality of different polynucleotide probes according to the combined rank of the different polynucleotide probes.

In yet another general embodiment, the methods of the invention comprise: (a) identifying those polynucleotide probes in the plurality of polynucleotide probes that have particular values (or a particular range of values) of one, two, three or more properties or parameters (e.g., selected among the properties and parameters listed hereinabove); (b) ranking the identified polynucleotide probes according to each of two or more selected properties or parameters (e.g., selected among the properties and parameters listed hereinabove) so that a rank is obtained for each of the two or more selected parameters; and (c) obtaining a combined rank for each identified polynucleotide probe, wherein the combined rank is determined from the sum of the ranks obtained for each of the two or more selected properties or parameters. One or more different polynucleotide probes can then be selected from the identified polynucleotide probes according to the combined rank of the identified polynucleotide probes.

In such a general embodiment, the properties or parameters used to rank the identified probes in step (b) can be either the same as or, more preferably, different from the properties or parameters used to identify those polynucleotide probes in step (a). Also, in certain aspects of embodiments such as the general embodiments described above, the sum of the ranks obtained for each of the two or more selected properties or parameters can be, e.g., a weighted sum of the ranks obtained for each of the two or more selected properties or parameters.

The invention provides certain preferred aspects of the above methods wherein the steps of the methods are iteratively repeated, e.g., to select no more than 20, 10, 5 or 1 different polynucleotide probe or probes. The invention also provides preferred aspects of these methods wherein the polynucleotide probes comprise polynucleotide sequences that are, e.g., between 15-500, 20-100 or 40-60 bases in length.

In other embodiments, probe sequences can also be selected according to methods described in Lockhart et al., 1996, Nature Biotechnology 14:1675-1680; or Wodicka et al., 1997, Nature Biotechnology 15:1359-1367.

5.4. Methods for Determining Biological State and Biological Response

This invention utilizes the ability to measure the expression level of individual exons or multiexons of each of a plurality genes to determine the exon expression state of a cell sample. The cell sample can be of any organism, particularly one in which alternative splicing of pre-mRNA transcripts occurs (e.g., eukaryote, mammal, primate, human, non-human animal such as a dog, cat, horse, cow, mouse, rat, *Drosophila*, *C. elegans*, etc., plant such as rice, wheat, bean, tobacco, etc., and fungi). The cell sample can be from a diseased or healthy organism, or an organism predisposed to disease. The cell sample can be of a particular tissue type or development stage or subjected to a particular perturbation (stimulus). The exon expression profiles of different cell samples can also be compared, to assess differences between the biological states of such different cell samples. Thus, for example, perturbed vs. nonperturbed, e.g., diseased vs. healthy cell samples can be compared. This section and its subsections provides some exemplary methods for measuring the expression level of exons. One of skill in the art would appreciate that this invention is not limited to the following specific methods for measuring the exon expression level and responses of a biological system.

5.4.1. Transcript Assay Using Exon Arrays

This invention is particularly useful for the determination of the exon expression state or the transcriptional state of a cell or cell type or any other cell sample by monitoring exon expression profiles. One aspect of the invention provides polynucleotide probe arrays for simultaneous determination of the expression levels of a plurality of exons for each gene of a plurality of genes and methods for designing and making such polynucleotide probe arrays.

The exon expression level can be measured by any high throughput techniques. However measured, the result is either the absolute or relative amounts of transcripts or response data, including but not limited to values representing exon abundance ratios.

Preferably, measurement of the exon expression profile is made by hybridization to transcript arrays, which are described in this subsection In a preferred embodiment, the present invention makes use of "exon transcript arrays" or "exon profiling arrays". Exon transcript arrays can be employed for analyzing the exon expression profile in a cell sample and especially for measuring the exon expression profile of a cell sample of a particular tissue type or developmental state or exposed to a drug of interest or to perturbations to a biological pathway of interest. In another embodiment, the cell sample can be from a patient, e.g., a diseased cell sample, and preferably can be compared to a healthy cell sample.

In one embodiment, an exon expression profile is obtained by hybridizing detectably labeled polynucleotides representing the exons in mRNA transcripts present in a cell (e.g., fluorescently labeled cDNA synthesized from total cell mRNA) to a microarray. A microarray is an array of positionally-addressable binding (e.g., hybridization) sites on a support for representing many of the exons in the genome of a cell or organism, preferably most or almost all of the genes. Each of such binding sites consists of polynucleotide probes bound to the predetermined region on the support. Microarrays can be made in a number of ways, of which several are described herein below. However produced, microarrays share certain characteristics. The arrays are reproducible, allowing multiple copies of a given array to be produced and easily compared with each other. Preferably, the microarrays are made from materials that are stable under binding (e.g., nucleic acid hybridization) conditions. The microarrays are preferably small, e.g., between about 1 $cm^2$ and 25 $cm^2$, preferably about 1 to 3 $cm^2$. However, both larger and smaller arrays are also contemplated and may be preferable, e.g., for simultaneously evaluating a very large number of different probes.

Preferably, a given binding site or unique set of binding sites in the microarray will specifically bind (e.g., hybridize) to an exon or multiexon of a single gene from a cell or organism (e.g., to exon of a specific mRNA or a specific cDNA derived therefrom).

The microarrays used in the methods and compositions of the present invention include one or more test probes, each of which has a polynucleotide sequence that is complementary to a subsequence of RNA or DNA to be detected. Each probe preferably has a different nucleic acid sequence, and the position of each probe on the solid surface of the array is preferably known. Indeed, the microarrays are preferably addressable arrays, more preferably positionally addressable arrays. More specifically, each probe of the array is preferably located at a known, predetermined position on the solid support such that the identity (i.e., the sequence) of each probe can be determined from its position on the array (i.e., on the support or surface). In some embodiments of the invention, the arrays are ordered arrays.

Preferably, the density of probes on a microarray or a set of microarrays is about 100 different (i.e., non-identical) probes per 1 $cm^2$ or higher. More preferably, a microarray used in the methods of the invention will have at least 550 probes per 1 $cm^2$, at least 1,000 probes per 1 $cm^2$, at least 1,500 probes per 1 $cm^2$ or at least 2,000 probes per 1 $cm^2$. In a particularly preferred embodiment, the microarray is a high density array, preferably having a density of at least about 2,500 different probes per 1 $cm^2$. The microarrays used in the invention therefore preferably contain at least 2,500, at least 5,000, at least 10,000, at least 15,000, at least 20,000, at least 25,000, at least 50,000 or at least 55,000 different (i.e., non-identical) probes.

In one embodiment, the microarray is an array (i.e., a matrix) in which each position represents a discrete binding site for an exon of a transcript encoded by a gene (e.g., for an exon of an mRNA or a cDNA derived therefrom). The collection of binding sites on a microarray contains sets of binding sites for sets of exons for each of a plurality of genes. For example, in various embodiments, the microarrays of the invention can comprise binding sites for products encoded by fewer than 50% of the genes in the genome of an organism. Alternatively, the microarrays of the invention can have binding sites for the products encoded by at least 50%, at least 75%, at least 85%, at least 90%, at least 95%, at least 99% or 100% of the genes in the genome of an organism. In other embodiments, the microarrays of the invention can having binding sites for products encoded by fewer than 50%, by at least 50%, by at least 75%, by at least 85%, by at least 90%, by at least 95%, by at least 99% or by 100% of the genes expressed by a cell of an organism. The binding site can be a DNA or DNA analog to which a particular RNA can specifically hybridize. The DNA or DNA analog can be, e.g., a synthetic oligomer or a gene fragment, e.g. corresponding to an exon.

In some embodiments of the present invention, an exon is represented in the exon profiling arrays by a set of binding sites comprising probes with different polynucleotides that are complementary to different sequence segments of the exon. Such polynucleotides are preferably of the length of 15 to 200 bases, more preferably of the length of 20 to 100 bases, most preferably 40-60 bases. It will be understood that each probe sequence may also comprise linker sequences in addition to the sequence that is complementary to its target sequence. As used herein, a linker sequence refers to a sequence between the sequence that is complementary to its target sequence and the surface of support. For example, in preferred embodiments the exon profiling arrays of the invention comprise one probe specific to each target exon. However, if desired, the exon profiling arrays may contain at least 2, 5, 10, 100, 1000 probes specific to some target exons. For example, the array may contain probes tiled across the sequence of the longest mRNA isoform of a gene at single base steps.

In specific embodiments of the invention, when an exon has alternative spliced variants, a set of polynucleotide probes of successive overlapping sequences, i.e., tiled sequences, across the genomic region containing the longest variant of an exon can be included in the exon profiling arrays. The set of polynucleotide probes can comprise successive overlapping sequences at steps of a predetermined base intervals, e.g. at steps of 1, 5, or 10 base intervals, span, or are tiled across, the mRNA containing the longest variant. Such set of probes therefore can be used to scan the genomic region containing all variants of an exon to determine the expressed variant or variants of the exon to determine the expressed variant or variants of the exon. Alternatively or additionally, a set of polynucleotide probes comprising exon specific probes and/or variant junction probes can be included in the exon profiling array. As used herein, a variant junction probe refers to a probe specific to the junction region of the particular exon variant and the neighboring exon. In a preferred embodiment, the probe set contains variant junction probes specifically hybridizable to each of all different splice junction sequences of the exon. In another preferred embodiment, the probe set contains exon specific probes specifically hybridizable to the common sequences in all different variants of the exon, and/or variant junction probes specifically hybridizable to the different splice junction sequences of the exon.

In some other embodiments of the invention, an exon is represented in the exon profiling arrays by a probe comprising a polynucleotide that is complementary to the full length exon. In such embodiments, an exon is represented by a single binding site on the exon profiling arrays. In some preferred embodiments of the invention, an exon is represented by one or more binding sites on the exon profiling arrays, each of the binding sites comprising a probe with a polynucleotide sequence that is complementary to an RNA fragment that is a substantial portion of the target exon. The lengths of such probes are normally between about 15-600 bases, preferably between about 20-200 bases, more preferably between about 30-100 bases, and most preferably between about 40-80 bases. The average length of an exon is about 200 bases (see, e.g., Lewin, *Genes V*, Oxford University Press, Oxford, 1994). A probe of length of about 40-80 allows more specific binding of the exon than a probe of shorter length, thereby increasing the specificity of the probe to the target exon. For certain genes, one or more targeted exons may have sequence lengths less than about 40-80 bases. In such cases, if probes with sequences longer than the target exons are to be used, it may be desirable to design probes comprising sequences that include the entire target exon flanked by sequences from the adjacent constitutively splice exon or exons such that the probe sequences are complementary to the corresponding sequence segments in the mRNAs. Using flanking sequence from adjacent constitutively spliced exon or exons rather than the genomic flanking sequences, i.e., intron sequences, permits comparable hybridization stringency with other probes of the same length. Preferably the flanking sequence used are from the adjacent constitutively spliced exon or exons that are not involved in any alternative pathways. More preferably the flanking sequences used do not comprise a significant portion of the sequence of the adjacent exon or exons so that cross-hybridization can be minimized. In some embodiments, when a target exon that is shorter than the desired probe length is involved in alternative splicing, probes comprising flanking sequences in different alternatively spliced mRNAs are designed so that expression level of the exon expressed in different alternatively spliced mRNAs can be measured.

In some other embodiments of the invention, when alternative splicing pathways and/or exon duplication in separate genes are to be distinguished, the DNA array or set of arrays can also comprise probes that are complementary to sequences spanning the junction regions of a multiexon. Preferably, such probes comprise sequences from the two exons which are not substantially overlapped with probes for each individual exons so that cross hybridization can be minimized. The DNA array or set of arrays can also comprise probes for full length multiexons. Probes that comprise sequences from more than one exons are useful in distinguishing alternative splicing pathways and/or expression of duplicated exons in separate genes if the multiexons occurs in one or more alternative spliced mRNAs and/or one or more separated genes that contain the duplicated exons but not in other alternatively spliced mRNAs and/or other genes that contain the duplicated exons. Alternatively, for duplicate exons in separate genes, if the exons from different genes show substantial difference in sequence homology, it is preferable to include probes that are different so that the exons from different genes can be distinguished.

It will be apparent to one skilled in the art that any of the probe schemes, supra, can be combined on the same exon profiling array and/or on different arrays within the same set of exon profiling arrays so that a more accurate determination of the exon expression profile for a plurality of genes can be accomplished. It will also be apparent to one skilled in the art that the different probe schemes can also be used for different levels of accuracies in exon profiling. For example, an exon profiling array or array set comprising a small set of probes for each exon may be used to determine the relevant genes and/or RNA splicing pathways under certain specific conditions. An array or array set comprising larger sets of probes for the exons that are of interest is then used to more accurately determine the exon expression profile under such specific conditions. Other DNA array strategies that allow more advantageous use of different probe schemes are also encompassed.

Preferably, the microarrays used in the invention have binding sites (i.e., probes) for sets of exons for one or more genes relevant to the action of a drug of interest or in a biological pathway of interest. As discussed above, a "gene" is identified as a portion of DNA that is transcribed by RNA polymerase, which may include a 5' untranslated region ("UTR"), introns, exons and a 3' UTR. The number of genes in a genome can be estimated from the number of mRNAs expressed by the cell or organism, or by extrapolation of a well characterized portion of the genome. When the genome of the organism of interest has been sequenced, the number of ORFs can be determined and mRNA coding regions identified by analysis of the DNA sequence. For example, the genome of Saccharomyces cerevisiae has been completely sequenced and is reported to have approximately 6275 ORFs encoding sequences longer the 99 amino acid residues in length. Analysis of these ORFs indicates that there are 5,885 ORFs that are likely to encode protein products (Goffeau et al., 1996, Science 274:546-567). In contrast, the human genome is estimated to contain approximately 30,000 to 130,000 genes (see Crollius et al., 2000, Nature Genetics 25:235-238; Ewing et al., 2000, Nature Genetics 25:232-234). Genome sequences for other organisms, including but not limited to Drosophila, C. elegans, plants, e.g., rice and Arabidopsis, and mammals, e.g., mouse and human, are also completed or nearly completed. Thus, in preferred embodiments of the invention, an array set comprising in total probes for all known or predicted exons in the genome of an organism is provided. As a non-limiting example, the present invention provides an array set comprising one or two probes for each known or predicted exon in the human genome.

It will be appreciated that when cDNA complementary to the RNA of a cell is made and hybridized to a microarray under suitable hybridization conditions, the level of hybridization to the site in the array corresponding to an exon of any particular gene will reflect the prevalence in the cell of mRNA or mRNAs containing the exon transcribed from that gene. For example, when detectably labeled (e.g., with a fluorophore) cDNA complementary to the total cellular mRNA is hybridized to a microarray, the site on the array corresponding to an exon of a gene (i.e., capable of specifically binding the product or products of the gene expressing) that is not transcribed or is removed during RNA splicing in the cell will have little or no signal (e.g., fluorescent signal), and an exon of a gene for which the encoded mRNA expressing the exon is prevalent will have a relatively strong signal. The relative abundance of different mRNAs produced from the same gene by alternative splicing is then determined by the signal strength pattern across the whole set of exons monitored for the gene.

In preferred embodiments, cDNAs from cell samples from two different conditions are hybridized to the binding sites of the microarray using a two-color protocol. In the case of drug responses one cell sample is exposed to a drug and another cell sample of the same type is not exposed to the drug. In the case of pathway responses one cell is exposed to a pathway perturbation and another cell of the same type is not exposed to the pathway perturbation. The cDNA derived from each of the two cell types are differently labeled (e.g., with Cy3 and Cy5) so that they can be distinguished. In one embodiment, for example, cDNA from a cell treated with a drug (or exposed to a pathway perturbation) is synthesized using a fluorescein-labeled dNTP, and cDNA from a second cell, not drug-exposed, is synthesized using a rhodamine-labeled dNTP. When the two cDNAs are mixed and hybridized to the microarray, the relative intensity of signal from each cDNA set is determined for each site on the array, and any relative difference in abundance of a particular exon detected.

In the example described above, the cDNA from the drug-treated (or pathway perturbed) cell will fluoresce green when the fluorophore is stimulated and the cDNA from the untreated cell will fluoresce red. As a result, when the drug treatment has no effect, either directly or indirectly, on the transcription and/or post-transcriptional splicing of a particular gene in a cell, the exon expression patterns will be indistinguishable in both cells and, upon reverse transcription, red-labeled and green-labeled cDNA will be equally prevalent. When hybridized to the microarray, the binding site(s) for that species of RNA will emit wavelengths characteristic of both fluorophores. In contrast, when the drug-exposed cell is treated with a drug that, directly or indirectly, change the transcription and/or post-transcriptional splicing of a particular gene in the cell, the exon expression pattern as represented by ratio of green to red fluorescence for each exon binding site will change. When the drug increases the prevalence of an mRNA, the ratios for each exon expressed in the mRNA will increase, whereas when the drug decreases the prevalence of an mRNA, the ratio for each exons expressed in the mRNA will decrease.

The use of a two-color fluorescence labeling and detection scheme to define alterations in gene expression has been described in connection with detection of mRNAs, e.g., in Shena et al., 1995, Quantitative monitoring of gene expression patterns with a complementary DNA microarray, Science 270:467-470, which is incorporated by reference in its entirety for all purposes. The scheme is equally applicable to labeling and detection of exons. An advantage of using cDNA labeled with two different fluorophores is that a direct and internally controlled comparison of the mRNA or exon expression levels corresponding to each arrayed gene in two cell states can be made, and variations due to minor differences in experimental conditions (e.g., hybridization conditions) will not affect subsequent analyses. However, it will be recognized that it is also possible to use cDNA from a single cell, and compare, for example, the absolute amount of a particular exon in, e.g., a drug-treated or pathway-perturbed cell and an untreated cell. Furthermore, labeling with more than two colors is also contemplated in the present invention. In some embodiments of the invention, at least 5, 10, 20, or 100 dyes of different colors can be used for labeling. Such labeling permits simultaneous hybridizing of the distinguishably labeled cDNA populations to the same array, and thus measuring, and optionally comparing the expression levels of, mRNA molecules derived from more than two samples. Dyes that can be used include, but are not limited to, fluorescein and its derivatives, rhodamine and its derivatives, texas red, 5'carboxy-fluorescein ("FMA"), 2',7'-dimethoxy-4',5'-dichloro-6-carboxy-fluorescein ("JOE"), N,N,N',N'-tetramethyl-6-carboxy-rhodamine ("TAMRA"), 6'carboxy-X-rhodamine ("ROX"), HEX, TET, IRD40, and IRD41, cyamine dyes, including but are not limited to Cy3, Cy3.5 and Cy5; BODIPY dyes including but are not limited to BODIPY-FL, BODIPY-TR, BODIPY-TMR, BODIPY-630/650, and BODIPY-650/670; and ALEXA dyes, including but are not limited to ALEXA-488, ALEXA-532, ALEXA-546, ALEXA-568, and ALEXA-594; as well as other fluorescent dyes which will be known to those who are skilled in the art.

5.4.2. Preparing Probes for Microarrays

As noted above, the "probe" to which a particular polynucleotide molecule, such an exon, specifically hybridizes according to the invention is a complementary polynucleotide sequence. The probes for exon profiling arrays are selected based on known and predicted exons determined in Section 5.2. Preferably one or more probes are selected for each target exon. Depending on the probe scheme as described in Section 5.4.1., the lengths and number of probes for each exon are chosen accordingly. For example, when a minimum number of probes are to be used for the detection of an exon, the probes normally comprise nucleotide sequences greater than about 40 bases in length. Alternatively, when a large set of redundant probes is to be used for an exon, the probes normally comprise nucleotide sequences of about 40-60 bases. The probes can also comprise sequences complementary to full length exons. The lengths of exons can range from less than 50 bases to more than 200 bases. Therefore, when a probe length longer than exon is to be used, it is preferable to augment the exon sequence with adjacent constitutively spliced exon sequences such that the probe sequence is complementary to the continuous mRNA fragment that contains the target exon. This will allow comparable hybridization stringency among the probes of an exon profiling array. It will be understood that each probe sequence may also comprise linker sequences in addition to the sequence that is complementary to its target sequence.

The probes may comprise DNA or DNA "mimics" (e.g., derivatives and analogues) corresponding to a portion of each exon of each gene in an organism's genome. In one embodiment, the probes of the microarray are complementary RNA or RNA mimics. DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone. Exemplary DNA mimics include, e.g., phosphorothioates. DNA can be obtained, e.g., by polymerase chain reaction (PCR) amplification of exon segments from genomic DNA, cDNA (e.g., by RT-PCR), or cloned sequences. PCR primers are preferably chosen based on known sequence of the exons or cDNA that result in amplification of unique fragments (i.e., fragments that do not share more than 10 bases of contiguous identical sequence with any other fragment on the microarray). Computer programs that are well known in the art are useful in the design of primers with the required specificity and optimal amplification properties, such as Oligo version 5.0 (National Biosciences). Typically each probe on the microarray will be between 20 bases and 600 bases, and usually between 30 and 200 bases in length. PCR methods are well known in the art, and are described, for example, in Innis et al., eds., 1990, *PCR Protocols: A Guide to Methods and Applications*, Academic Press Inc., San Diego, Calif. It will be apparent to one skilled in the art that controlled robotic systems are useful for isolating and amplifying nucleic acids.

An alternative, preferred means for generating the polynucleotide probes of the microarray is by synthesis of synthetic polynucleotides or oligonucleotides, e.g., using N-phosphonate or phosphoramidite chemistries (Froehler et al., 1986, *Nucleic Acid Res.* 14:5399-5407; McBride et al., 1983, *Tetrahedron Lett.* 24:246-248). Synthetic sequences are typically between about 15 and about 600 bases in length, more typically between about 20 and about 100 bases, most preferably between about 40 and about 70 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., 1993, *Nature* 363:566-568; U.S. Pat. No. 5,539,083).

In alternative embodiments, the hybridization sites (i.e., the probes) are made from plasmid or phage clones of genes, cDNAs (e.g., expressed sequence tags), or inserts therefrom (Nguyen et al., 1995, *Genomics* 29:207-209).

5.4.3. Attaching Probes to the Solid Surface

Preformed polynucleotide probes can be deposited on a support to form the array. Alternatively, polynucleotide probes can be synthesized directly on the support to form the array. The probes are attached to a solid support or surface, which may be made, e.g., from glass, plastic (e.g., polypropylene, nylon), polyacrylamide, nitrocellulose, gel, or other porous or nonporous material.

A preferred method for attaching the nucleic acids to a surface is by printing on glass plates, as is described generally by Schena et al, 1995, *Science* 270:467-470. This method is especially useful for preparing microarrays of cDNA (See also, DeRisi et al, 1996, *Nature Genetics* 14:457-460; Shalon et al., 1996, *Genome Res.* 6:639-645; and Schena et al., 1995, *Proc. Natl. Acad. Sci. U.S.A.* 93:10539-11286).

A second preferred method for making microarrays is by making high-density polynucleotide arrays. Techniques are known for producing arrays containing thousands of oligonucleotides complementary to defined sequences, at defined locations on a surface using photolithographic techniques for synthesis in situ (see, Fodor et al., 1991, *Science* 251:767-773; Pease et al., 1994, *Proc. Natl. Acad. Sci. U.S.A.* 91:5022-5026; Lockhart et al., 1996, *Nature Biotechnology* 14:1675; U.S. Pat. Nos. 5,578,832; 5,556,752; and 5,510,270) or other methods for rapid synthesis and deposition of defined oligonucleotides (Blanchard et al., *Biosensors & Bioelectronics* 11:687-690). When these methods are used, oligonucleotides (e.g., 60-mers) of known sequence are synthesized directly on a surface such as a derivatized glass slide. The array produced can be redundant, with several polynucleotide molecules per exon.

Other methods for making microarrays, e.g., by masking (Maskos and Southern, 1992, *Nucl. Acids. Res.* 20:1679-1684), may also be used. In principle, and as noted supra, any type of array, for example, dot blots on a nylon hybridization membrane (see Sambrook et al., supra) could be used. However, as will be recognized by those skilled in the art, very small arrays will frequently be preferred because hybridization volumes will be smaller.

In a particularly preferred embodiment, microarrays of the invention are manufactured by means of an ink jet printing device for oligonucleotide synthesis, e.g., using the methods and systems described by Blanchard in International Patent Publication No. WO 98/41531, published Sep. 24, 1998; Blanchard et al., 1996, *Biosensors and Bioelectronics* 11:687-690; Blanchard, 1998, in *Synthetic DNA Arrays in Genetic Engineering*, Vol. 20, J. K. Setlow, Ed., Plenum Press, New York at pages 111-123; and U.S. Pat. No. 6,028,189 to Blanchard. Specifically, the polynucleotide probes in such microarrays are preferably synthesized in arrays, e.g., on a glass slide, by serially depositing individual nucleotide bases in "microdroplets" of a high surface tension solvent such as propylene carbonate. The microdroplets have small volumes (e.g., 100 pL or less, more preferably 50 pL or less)

and are separated from each other on the microarray (e.g., by hydrophobic domains) to form circular surface tension wells which define the locations of the array elements (i.e., the different probes). Polynucleotide probes are normally attached to the surface covalently at the 3' end of the polynucleotide. Alternatively, polynucleotide probes can be attached to the surface covalently at the 5' end of the polynucleotide (see for example, Blanchard, 1998, in *Synthetic DNA Arrays in Genetic Engineering*, Vol. 20, J. K. Setlow, Ed., Plenum Press, New York at pages 111-123).

5.4.4. Target Polynucleotide Molecules

Target polynucleotides which may be analyzed by the methods and compositions of the invention include RNA molecules such as, but by no means limited to messenger RNA (mRNA) molecules, ribosomal RNA (rRNA) molecules, cRNA molecules (i.e., RNA molecules prepared from cDNA molecules that are transcribed in vivo) and fragments thereof. Target polynucleotides which may also be analyzed by the methods and compositions of the present invention include, but are not limited to DNA molecules such as genomic DNA molecules, cDNA molecules, and fragments thereof including oligonucleotides, ESTs, STSs, etc.

The target polynucleotides may be from any source. For example, the target polynucleotide molecules may be naturally occurring nucleic acid molecules such as genomic or extragenomic DNA molecules isolated from an organism, or RNA molecules, such as mRNA molecules, isolated from an organism. Alternatively, the polynucleotide molecules may be synthesized, including, e.g., nucleic acid molecules synthesized enzymatically in vivo or in vitro, such as cDNA molecules, or polynucleotide molecules synthesized by PCR, RNA molecules synthesized by in vitro transcription, etc. The sample of target polynucleotides can comprise, e.g., molecules of DNA, RNA, or copolymers of DNA and RNA. In preferred embodiments, the target polynucleotides of the invention will correspond to particular genes or to particular gene transcripts (e.g., to particular mRNA sequences expressed in cells or to particular cDNA sequences derived from such mRNA sequences). However, in many embodiments, particularly those embodiments wherein the polynucleotide molecules are derived from mammalian cells, the target polynucleotides may correspond to particular fragments of a gene transcript. For example, the target polynucleotides may correspond to different exons of the same gene, e.g., so that different splice variants of that gene may be detected and/or analyzed.

In preferred embodiments, the target polynucleotides to be analyzed are prepared in vitro from nucleic acids extracted from cells. For example, in one embodiment, RNA is extracted from cells (e.g., total cellular RNA, poly(A)$^+$ messenger RNA, fraction thereof) and messenger RNA is purified from the total extracted RNA. Methods for preparing total and poly(A)$^+$ RNA are well known in the art, and are described generally, e.g., in Sambrook et al., supra. In one embodiment, RNA is extracted from cells of the various types of interest in this invention using guanidinium thiocyanate lysis followed by CsCl centrifugation (Chirgwin et al., 1979, *Biochemistry* 18:5294-5299). cDNA is then synthesized from the purified mRNA using, e.g., oligo-dT or random primers. In preferred embodiments, the target polynucleotides are cRNA prepared from purified messenger RNA extracted from cells. As used herein, cRNA is defined here as RNA complementary to the source RNA. The extracted RNAs are amplified using a process in which doubled-stranded cDNAs are synthesized from the RNAs using a primer linked to an RNA polymerase promoter in a direction capable of directing transcription of anti-sense RNA. Anti-sense RNAs or cRNAs are then transcribed from the second strand of the double-stranded cDNAs using an RNA polymerase (see, e.g., U.S. Pat. Nos. 5,891, 636, 5,716,785; 5,545,522 and 6,132,997; see also, U.S. patent application Ser. No. 09/411,074, filed on Oct. 4, 1999 by Linsley and Schelter, now U.S. Pat. No. 6,271,002 B1 and U.S. Provisional Patent Application No. 60/253,641, filed on Nov. 28, 2000, by Ziman et al.). Both oligo-dT primers (U.S. Pat. Nos. 5,545,522 and 6,132,997) or random primers (U.S. Provisional Patent Application Ser. No. 60/253,641, filed on Nov. 28, 2000, by Ziman et al.) that contain an RNA polymerase promoter or complement thereof can be used. Preferably, the target polynucleotides are short and/or fragmented polynucleotide molecules which are representative of the original nucleic acid population of the cell.

The target polynucleotides to be analyzed by the methods and compositions of the invention are preferably detectably labeled. For example, cDNA can be labeled directly, e.g., with nucleotide analogs, or indirectly, e.g., by making a second, labeled cDNA strand using the first strand as a template. Alternatively, the double-stranded cDNA can be transcribed into cRNA and labeled.

Preferably, the detectable label is a fluorescent label, e.g., by incorporation of nucleotide analogs. Other labels suitable for use in the present invention include, but are not limited to, biotin, imminobiotin, antigens, cofactors, dinitrophenol, lipoic acid, olefinic compounds, detectable polypeptides, electron rich molecules, enzymes capable of generating a detectable signal by action upon a substrate, and radioactive isotopes. Preferred radioactive isotopes include $^{32}$P, $^{35}$S, $^{14}$C, $^{15}$N and $^{125}$I. Fluorescent molecules suitable for the present invention include, but are not limited to, fluorescein and its derivatives, rhodamine and its derivatives, texas red, 5'carboxy-fluorescein ("FMA"), 2',7'-dimethoxy-4',5'-dichloro-6-carboxy-fluorescein ("JOE"), N,N,N',N'-tetramethyl-6-carboxy-rhodamine ("TAMRA"), 6'carboxy-X-rhodamine ("ROX"), HEX, TET, IRD40, and IRD41. Fluorescent molecules that are suitable for the invention further include: cyamine dyes, including by not limited to Cy3, Cy3.5 and Cy5; BODIPY dyes including but not limited to BODIPY-FL, BODIPY-TR, BODIPY-TMR, BODIPY-630/650, and BODIPY-650/670; and ALEXA dyes, including but not limited to ALEXA-488, ALEXA-532, ALEXA-546, ALEXA-568, and ALEXA-594; as well as other fluorescent dyes which will be known to those who are skilled in the art. Electron rich indicator molecules suitable for the present invention include, but are not limited to, ferritin, hemocyanin, and colloidal gold. Alternatively, in less preferred embodiments the target polynucleotides may be labeled by specifically complexing a first group to the polynucleotide. A second group, covalently linked to an indicator molecules and which has an affinity for the first group, can be used to indirectly detect the target polynucleotide. In such an embodiment, compounds suitable for use as a first group include, but are not limited to, biotin and iminobiotin. Compounds suitable for use as a second group include, but are not limited to, avidin and streptavidin.

5.4.5. Hybridization to Microarrays

As described supra, nucleic acid hybridization and wash conditions are chosen so that the polynucleotide molecules to be analyzed by the invention (referred to herein as the "target polynucleotide molecules) specifically bind or specifically hybridize to the complementary polynucleotide sequences of the array, preferably to a specific array site, wherein its complementary DNA is located.

Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self complementary sequences.

Optimal hybridization conditions will depend on the length (e.g., oligomer versus polynucleotide greater than 200 bases) and type (e.g., RNA, or DNA) of probe and target nucleic acids. General parameters for specific (i.e., stringent) hybridization conditions for nucleic acids are described in Sambrook et al., (supra), and in Ausubel et al., 1987, *Current Protocols in Molecular Biology*, Greene Publishing and Wiley-Interscience, New York. When the cDNA microarrays of Schena et al. are used, typical hybridization conditions are hybridization in 5×SSC plus 0.2% SDS at 65° C. for four hours, followed by washes at 25° C. in low stringency wash buffer (1×SSC plus 0.2% SDS), followed by 10 minutes at 25° C. in higher stringency wash buffer (0.1×SSC plus 0.2% SDS) (Shena et al., 1996, *Proc. Natl. Acad. Sci. U.S.A.* 93:10614). Useful hybridization conditions are also provided in, e.g., Tijessen, 1993, *Hybridization With Nucleic Acid Probes*, Elsevier Science Publishers B.V. and Kricka, 1992, Nonisotopic DNA Probe Techniques, Academic Press, San Diego, Calif.

Particularly preferred hybridization conditions for use with the screening and/or signaling chips of the present invention include hybridization at a temperature at or near the mean melting temperature of the probes (e.g., within 5° C., more preferably within 2° C.) in 1 M NaCl, 50 mM MES buffer (pH 6.5), 0.5% sodium Sarcosine and 30% formamide.

5.4.6. Signal Detection and Data Analysis

It will be appreciated that when target sequences, e.g., cDNA or cRNA, complementary to the RNA of a cell is made and hybridized to a microarray under suitable hybridization conditions, the level of hybridization to the site in the array corresponding to an exon of any particular gene will reflect the prevalence in the cell of mRNA or mRNAs containing the exon transcribed from that gene. For example, when detectably labeled (e.g., with a fluorophore) cDNA complementary to the total cellular mRNA is hybridized to a microarray, the site on the array corresponding to an exon of a gene (i.e., capable of specifically binding the product or products of the gene expressing) that is not transcribed or is removed during RNA splicing in the cell will have little or no signal (e.g., fluorescent signal), and an exon of a gene for which the encoded mRNA expressing the exon is prevalent will have a relatively strong signal. The relative abundance of different mRNAs produced by from the same gene by alternative splicing is then determined by the signal strength pattern across the whole set of exons monitored for the gene.

In preferred embodiments, target sequences, e.g., cDNAs or cRNAs, from two different cells are hybridized to the binding sites of the microarray. In the case of drug responses one cell sample is exposed to a drug and another cell sample of the same type is not exposed to the drug. In the case of pathway responses one cell is exposed to a pathway perturbation and another cell of the same type is not exposed to the pathway perturbation. The cDNA or cRNA derived from each of the two cell types are differently labeled so that they can be distinguished. In one embodiment, for example, cDNA from a cell treated with a drug (or exposed to a pathway perturbation) is synthesized using a fluorescein-labeled dNTP, and cDNA from a second cell, not drug-exposed, is synthesized using a rhodamine-labeled dNTP. When the two cDNAs are mixed and hybridized to the microarray, the relative intensity of signal from each cDNA set is determined for each site on the array, and any relative difference in abundance of a particular exon detected.

In the example described above, the cDNA from the drug-treated (or pathway perturbed) cell will fluoresce green when the fluorophore is stimulated and the cDNA from the untreated cell will fluoresce red. As a result, when the drug treatment has no effect, either directly or indirectly, on the transcription and/or post-transcriptional splicing of a particular gene in a cell, the exon expression patterns will be indistinguishable in both cells and, upon reverse transcription, red-labeled and green-labeled cDNA will be equally prevalent. When hybridized to the microarray, the binding site(s) for that species of RNA will emit wavelengths characteristic of both fluorophores. In contrast, when the drug-exposed cell is treated with a drug that, directly or indirectly, changes the transcription and/or post-transcriptional splicing of a particular gene in the cell, the exon expression pattern as represented by ratio of green to red fluorescence for each exon binding site will change. When the drug increases the prevalence of an mRNA, the ratios for each exon expressed in the mRNA will increase, whereas when the drug decreases the prevalence of an mRNA, the ratio for each exons expressed in the mRNA will decrease.

The use of a two-color fluorescence labeling and detection scheme to define alterations in gene expression has been described in connection with detection of mRNAs, e.g., in Shena et al., 1995, Quantitative monitoring of gene expression patterns with a complementary DNA microarray, Science 270:467-470, which is incorporated by reference in its entirety for all purposes. The scheme is equally applicable to labeling and detection of exons. An advantage of using target sequences, e.g., cDNAs or cRNAs, labeled with two different fluorophores is that a direct and internally controlled comparison of the mRNA or exon expression levels corresponding to each arrayed gene in two cell states can be made, and variations due to minor differences in experimental conditions (e.g., hybridization conditions) will not affect subsequent analyses. However, it will be recognized that it is also possible to use cDNA from a single cell, and compare, for example, the absolute amount of a particular exon in, e.g., a drug-treated or pathway-perturbed cell and an untreated cell.

In other preferred embodiments, single channel detection methods, e.g., using one-color fluorescence labeling, are used (see U.S. provisional patent application Ser. No. 60/227,966, filed on Aug. 25, 2000). In this embodiment, arrays comprising reverse-complement (RC) probes are designed and produced. Because a reverse complement of a DNA sequence has sequence complexity that is equivalent to the corresponding forward-strand (FS) probe that is complementary to a target sequence with respect to a variety of measures (e.g., measures such as GC content and GC trend are invariant under the reverse complement), a RC probe is used to as a control probe for determination of level of non-specific cross hybridization to the corresponding FS probe. The significance of the FS probe intensity of a target sequence is determined by comparing the raw intensity measurement for the FS probe and the corresponding raw intensity measurement for the RC probe in conjunction with the respective measurement errors. In a preferred embodiment, an exon is called present if the intensity difference between the FS probe and the corresponding RC probe is significant. More preferably, an exon is called present if the FS probe intensity is also significantly above background level. Single channel detection methods can be used in conjunction with multi-color labeling. In one embodiment, a plurality of different samples, each labeled with a different color, is hybridized to an array. Differences between FS and RC probes for each color are used to determine the level of hybridization of the corresponding sample.

When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., 1996, Genome Res. 6:639-645). In a preferred embodiment, the arrays are scanned with a laser fluorescence scanner with a computer controlled X-Y stage and a microscope objective. Sequential excitation of the two fluorophores is achieved with a multi-line, mixed gas laser, and the emitted light is split by wavelength and detected with two photomultiplier tubes. Such fluorescence laser scanning devices are described, e.g., in Schena et al., 1996, Genome Res. 6:639-645. Alternatively, the fiber-optic bundle described by Ferguson et al., 1996, Nature Biotech. 14:1681-1684, may be used to monitor mRNA abundance levels at a large number of sites simultaneously.

Signals are recorded and, in a preferred embodiment, analyzed by computer, e.g., using a 12 bit analog to digital board. In one embodiment, the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the transcript array, a ratio of the emission of the two fluorophores can be calculated. The ratio is independent of the absolute expression level of the cognate gene, but is useful for genes whose expression is significantly modulated by drug administration, gene deletion, or any other tested event.

According to the method of the invention, the relative abundance of an mRNA and/or an exon expressed in an mRNA in two cells or cell lines is scored as perturbed (i.e., the abundance is different in the two sources of mRNA tested) or as not perturbed (i.e., the relative abundance is the same). As used herein, a difference between the two sources of RNA of at least a factor of about 25% (i.e., RNA is 25% more abundant in one source than in the other source), more usually about 50%, even more often by a factor of about 2 (i.e., twice as abundant), 3 (three times as abundant), or 5 (five times as abundant) is scored as a perturbation. Present detection methods allow reliable detection of difference of an order of about 3-fold to about 5-fold, but more sensitive methods are expected to be developed.

It is, however, also advantageous to determine the magnitude of the relative difference in abundances for an mRNA and/or an exon expressed in an mRNA in two cells or in two cell lines. This can be carried out, as noted above, by calculating the ratio of the emission of the two fluorophores used for differential labeling, or by analogous methods that will be readily apparent to those of skill in the art.

5.5. Methods for Detecting Alternative Splicing

The methods of the invention can be used for detecting alternative splicing in different samples, e.g., different tissues or same tissue at different development stages or under different environmental conditions. For example, if all exons in a gene behave the same, i.e., expressed at the same level, measured expression levels of exons in the gene can be averaged. When alternative splicing occurs in a gene, different exons in the gene may have different expression levels. The pattern of expression levels of exons in a gene, such as the relative expression levels of exons, can thus be compared to detect alternative splicing in different samples, e.g., different tissues or same tissue at different development stages or under different environmental conditions. In one embodiment, the expression levels of a plurality of individual exons or multiexons in each of a plurality of different genes of a first cell sample from a tissue of an organism are measured. The expression levels of a plurality of individual exons or multiexons in each of a plurality of different genes of a second cell sample from the same species of the organism but from a different tissue or developmental stage are also measured. The measured expression levels of each exon in said first cell sample to measured expression level of the same exon in said second cell sample are then compared to identify differences in the expression levels of one or more exons or multiexons between the two cell samples. The identified differences indicates alternative splicings in the first and second cell samples. Alternative splicing in more than two samples can also be compared. In some embodiments of the invention, the expression levels of exons in a plurality of genes from 5, 10, 25, 50, 100, or 1,000 different samples are compared to identify differences in alternative splicing in these samples, e.g., different tissues or same tissue at different development stages or under different environmental conditions.

Alternatively, the measured exon expression profile of a cell sample, i.e., measured expression levels of one or more exons or multiexons in the cell sample, can be compared with a database containing exon expression profiles for different types of cells in the same or different species. In a preferred embodiment, statistically significant differences in the measured exon expression profile are determined. This is useful in identifying similarity in RNA splicing between the cell sample and one or more cell types in the database. It is also useful in identifying new RNA splicing pathways.

5.6. Pathway Response to Perturbations

The methods of the invention can also be used for determining effects of perturbations on RNA splicing pathways. In one aspect of the invention, exon expression change in a cell sample in response to one or more perturbations is measured to determine the biological response of the cell sample to the perturbation. In one embodiment, the expression levels of a plurality of exons or multiexons in a cell sample, which has been subjected to the perturbation, are measured for a plurality of genes in the cell sample. The measured expression levels are then compared with the expression levels of the same set of exons or multiexons in a cell sample from the same species of the organism, which has not been subjected to the perturbation. A change in the expression levels of the measured exons or multiexons, or a portion of the measured exons or multiexons, indicates the biological response of the cell sample to the perturbation. The exons or multiexons that show expression level changes under the perturbation permit the determination of the metabolic pathways and/or RNA splicing pathways affected by the perturbation. The perturbation can be exposure to a drug or environmental change, or the presence of a diseased state, or any of the perturbations described in Section 5.8 and its subsections infra.

Cell samples can also be subjected to graded perturbations to pathways of interest. In one aspect of the invention, exon expression change in response to graded perturbations is determined. Preferably, the perturbations should target different pathways, including splicing pathways. More preferably, the perturbations perturb both metabolic and splicing pathways. The samples exposed to the perturbation and samples not exposed to the perturbation can be used to construct exon expression arrays, which are measured to find the sets of exons with modified expression and the degree of modification due to exposure to the perturbation.

Further, it is preferable in order to reduce experimental error to reverse the fluorescent labels in two-color differential hybridization experiments to reduce biases peculiar to individual exons or array spot locations. In other words, it is preferable to first measure transcript expression with one labeling (e.g., labeling perturbed cells with a first fluorochrome and unperturbed cells with a second fluorochrome) of the exons from the two cells being measured, and then to measure transcript expression from the two cells with reversed labeling (e.g., labeling perturbed cells with the second fluorochrome and unperturbed cells with the first fluorochrome). Multiple measurements over exposure levels and perturbation control parameter levels provide additional experimental error control. With adequate sampling a tradeoff may be made when choosing the width of the spline function S used to interpolate response data between averaging of errors and loss of structure in the response functions.

The measured exon expression profile of a cell sample under a perturbation can be compared with a database or "compendium" of exon expression profiles for various types of cells in the same or different species under various perturbations. This is useful in identifying similarity in response of RNA splicing pathways between the cell sample and one or more cell types in the database. It is also useful in identifying similarity in the effects of perturbations on RNA splicing pathways.

In some embodiments, the compendium can be a compendium of exon expression profiles from other modifications or perturbations to cells or an organism, including any of the modifications and perturbations described in Section 5.8 below. For example, the compendium can be a compendium of exon expression profiles from cell samples under modifications or perturbations to RNA abundances, RNA activities and alternative RNA splicings ("perturbation exon expression profiles"). The compendium can also be a compendium of perturbation exon expression profiles from treating cells or an organism with particular drugs; most preferably well characterized drugs that have a specific, known mechanism of action (i.e., drugs having a known, specific target). The compendium can also be a compendium comprising mixtures of any two or more of the above-described modifications and perturbations. In particular, the compendium can comprise any mixture of perturbation exon expression profiles from any of the modifications or perturbations described herein and, in particular, in Section 5.8 below.

The compendium preferably comprises a plurality of perturbation exon expression profiles. In particular, the compendium preferably comprises perturbation exon expression profiles corresponding to perturbations to a substantial fraction of the exons of a cell or organism. For example, in embodiments, wherein the compendium is a compendium of profiles from genetically modified cells or organisms, the compendium preferably includes perturbation exon expression profiles from genetic modifications to at least 2% of the genes of the cell or organism. More preferably, the compendium includes perturbation exon expression profiles from genetic modifications to at least 5%, still more preferably at least 15%, still more preferably at least 30%, still more preferably at least 40%, most preferably 75% of the genes of the cell or organism. In one embodiment, wherein the cell or organism is a cell or organism for which the sequence of the entire genome has been determined or substantially determined, the compendium most preferably comprises perturbation exon expression profiles from genetic modifications to all or substantially all of the genes of the cell or organism.

A "gene" is defined as the portion of DNA that is transcribed by RNA polymerase. Thus, a gene may include a 5' untranslated region ("UTR"), introns, exons and a 3' UTR. It is noted that the sequence of the entire genome of a cell or organism of interest need not have been determined to practice the methods of the present invention. Thus, although only a fraction of the genes in a genome have been completely sequenced, the methods of the present invention can be practiced using a compendium of perturbation exon expression profiles corresponding to perturbations of only exons in these genes. Further, the number of genes for which partial sequences, such as ESTs are available, is much higher. As the skilled artisan readily appreciates, the modification and perturbation methods described below in Section 5.8 can be readily practiced using target genes or RNAs for which only the partial sequence, such as an EST sequence, is known.

As noted, in Section 5.1.3 above, the response of gene i to a perturbation m can be represented as the vector $v_i^{m,q_i}$ whose individual elements $b_{ij}^{m,q_i}$ is the level of the response of the j'th exon of gene i to perturbation m in the $q_i$'th RNA splicing pathway (e.g., the logarithm of the ratio of the expression level of exon j when the cell is subject to perturbation m to when the cell is not subject to perturbation m). Accordingly, the perturbation exon expression profiles in a compendium of the present invention are most preferably obtained or measured under identical or at least substantially identical conditions that differ only by the particular perturbation of the perturbation exon expression profile. In other words, the unperturbed or reference state of each perturbation exon expression profile in the compendium is preferably identical for all of the perturbation exon expression profiles. Likewise, the perturbed state of each perturbation exon expression profile should differ from the unperturbed state by the specific perturbation of the perturbation exon expression profile (e.g., the specific genetic mutation, the specific drug exposure, or the specific change in nutrient or other growth conditions).

For example, the perturbation exon expression profiles are most preferably obtained for identical cell types. More specifically, the cells are preferably isogenic cells, or at least substantially isogenic cells, that are obtained from the same species of organism, and more preferably from the same tissue or same tissue type of that species of organism. The perturbation exon expression profile are also preferably obtained or measured from cells that are at the same stage of growth (i.e., cells that are in the same phase of the cell cycle). In embodiments, wherein the cells are cells from a multicellular organism such as a plant or an animal, the cells are preferably obtained from one or more individual organisms during the same developmental stage (e.g., cells from an embryonic organism or, alternatively, from an adult organism). The exon expression profile are also preferably obtained from cells grown under identical conditions; such as identical conditions of temperature and nutrient content. It is further noted that, although each perturbation will most preferably consist of a single change to a cell (e.g., mutation of only a single gene, exposure of the cell to only a single drug), perturbations that comprise more than one change to the cell are also contemplated (e.g., mutation of one or more genes and exposure of the cells to a particular drug).

In a preferred embodiment, expression profiles in a compendium of the present invention are obtained under conditions that inhibit growth of the perturbed cells. This is because perturbation exon expression profiles are typically strongest (i.e., the absolute amplitudes of the exons' responses to the perturbations are largest) when the conditions are conditions under which the perturbed cell grows poorly or has a reduced growth rate. That is to say, amplitudes of expression levels for measured exons (specifically, for different genetic transcripts) in these mutants are most different from the unperturbed or wild-type cells. Likewise, the expression profiles of mutants that did not show substantially lower growth rates under conditions used in these experiments have expression profiles that are relatively similar to the expression profiles of unperturbed or wild-type cells. However, it is merely preferable, but not essential, that perturbation experiments be performed under conditions wherein the perturbation(s) inhibit cell growth.

Further, the methods and systems of the present invention can also employ a plurality of compendia, rather than only a single compendium, of perturbation exon expression profile. For example, it is possible, using the methods and compositions of the present invention, to generate a plurality of "parallel" compendia encompassing a plurality of different growth conditions. Each of the compendia would then comprise perturbations exon expression profile for the same perturbations but under different baseline or unperturbed conditions (most preferably different conditions of cell growth). For example, the "parallel" compendia might encompass different nutrient conditions, different conditions of temperature, different stages of cell growth, different cell types (e.g., cells from different tissues of the same species of organism) or corresponding to different stages of development.

5.7. Measurement of Drug Response Data

Drug responses are obtained for use in the instant invention by measuring the exon expression state changed by drug exposure. The biological response described on the exon level can be measured by exon profiling methods described in the previous sections. The measured response data include values representing exon expression level values or exon expression level ratios for various exons or multiexons in a plurality of genes, which can reflect both DNA expression ratios (in the absence of differences in RNA degradation rates) and alternative RNA splicing ratio.

To measure drug response data, cell are exposed to graded levels of the drug or drug candidate of interest. When the cells are grown in vitro, the compound is usually added to their nutrient medium. The drug is added in a graded amount that depends on the particular characteristics of the drug, but usually will be between about 1 ng/ml and 100 mg/ml. In some cases a drug will be solubilized in a solvent such as DMSO.

The exon expression profiles of cells exposed to the drug and of cells not exposed to the drug are measured according to the methods described in the previous section. Preferably, exon transcript arrays are used to find the genes with altered exon expression profiles due to exposure to the drug.

It is preferable for measurements of drug responses, in the case of two-colored differential hybridization described above, to measure with reversed labeling. Also, it is preferable that the levels of drug exposure used provide sufficient resolution of rapidly changing regions of the drug response, e.g., by using approximately ten levels of drug exposure.

5.8. Methods for Probing Exon Expression States

One aspect of the invention provides methods for the analysis of exon expression state. The methods of this invention are also useful for the analysis of responses of a cell sample to perturbations designed to probe cellular state. Preferred perturbations are those that cause a change in the amount of alternative splicing that occurs in one or more RNA transcripts. This section and its subsections herein below provide some illustrative methods for probing exon expression states.

Methods for targeted perturbation of cells are increasingly widely known and applied in the art. The following methods are exemplary of those that can be used to produce modifications in the exon expression profile of a cell sample.

The exemplary methods described in the following include use of titratable expression systems, use of transfection or viral transduction systems, direct modifications to RNA abundances or activities, direct modifications of protein abundances, and direct modification of protein activities including use of drugs (or chemical moieties in general).

5.8.1. Titratable Expression Systems

In mammalian cells, several means of titrating expression of genes are available (Spencer, 1996, Trends Genet. 12:181-187). As mentioned above, the Tet system is widely used, both in its original form, the "forward" system, in which addition of doxycycline represses transcription, and in the newer "reverse" system, in which doxycycline addition stimulates transcription (Gossen et al., 1995, Proc. Natl. Acad. Sci, USA 89:5547-5551; Hoffmann et al., 1997, Nucl. Acids. Res. 25:1078-1079; Hofmann et al., 1996, Proc. Natl. Acad. Sci. USA 83:5185-5190; Paulus et al., 1996, Journal of Virology 70:62-67). Another commonly used controllable promoter system in mammalian cells is the ecdysone-inducible system developed by Evans and colleagues (No et al., 1996, Proc. Nat. Acad. Sci. USA 93:3346-3351), where expression is controlled by the level of muristerone added to the cultured cells. Finally, expression can be modulated using the "chemical-induced dimerization" (CID) system developed by Schreiber, Crabtree, and colleagues (Belshaw et al., 1996, Proc. Nat. Acad. Sci. USA 93:4604-4607; Spencer, 1996, Trends Genet. 12:181-187) and similar systems in yeast. In this system, the gene of interest is put under the control of the CID-responsive promoter, and transfected into cells expressing two different hybrid proteins, one comprised of a DNA-binding domain fused to FKBP12, which binds FK506. The other hybrid protein contains a transcriptional activation domain also fused to FKBP12. The CID inducing molecule is FK1012, a homodimeric version of FK506 that is able to bind simultaneously both the DNA binding and transcriptional activating hybrid proteins. In the graded presence of FK1012, graded transcription of the controlled gene is activated.

For each of the mammalian expression systems described above, as is widely known to those of skill in the art, the gene of interest is put under the control of the controllable promoter, and a plasmid harboring this construct along with an antibiotic resistance gene is transfected into cultured mammalian cells. In general, the plasmid DNA integrates into the genome, and drug resistant colonies are selected and screened for appropriate expression of the regulated gene. Alternatively, the regulated gene can be inserted into an episomal plasmid such as pCEP4 (Invitrogen, Inc.), which contains components of the Epstein-Barr virus necessary for plasmid replication.

In a preferred embodiment, titratable expression systems, such as the ones described above, are introduced for use into cells or organisms lacking the corresponding endogenous gene and/or gene activity, e.g., organisms in which the endogenous gene has been disrupted or deleted. Methods for producing such "knock outs" are well known to those of skill in the art, see e.g., Pettitt et al., 1996, Development 122:4149-4157; Spradling et al., 1995, Proc. Natl. Acad. Sci. USA, 92:10824-10830; Ramirez-Solis et al., 1993, Methods Enzymol. 225:855-878; and Thomas et al., 1987, Cell 51:503-512.

5.8.2. Transfection Systems for Mammalian Cells

Transfection or viral transduction of target genes can introduce controllable perturbations in biological exon expression states in mammalian cells. Preferably, transfection or transduction of a target gene can be used with cells that do not naturally express the target gene of interest. Such non-expressing cells can be derived from a tissue not normally expressing the target gene or the target gene can be specifically mutated in the cell. The target gene of interest can be cloned into one of many mammalian expression plasmids, for example, the pcDNA3.1+/− system (Invitrogen, Inc.) or retroviral vectors, and introduced into the non-expressing host cells. Transfected or transduced cells expressing the target gene may be isolated by selection for a drug resistance marker encoded by the expression vector. The level of gene transcription is monotonically related to the transfection dosage. In this way, the effects of varying levels of the target gene may be investigated.

A particular example of the use of this method is the search for drugs that target the src-family protein tyrosine kinase, lck, a key component of the T cell receptor activation exon expression state (Anderson et al., 1994, Adv. Immunol. 56:171-178). Inhibitors of this enzyme are of interest as potential immunosuppressive drugs (Hanke, 1996, J. Biol Chem 271:695-701). A specific mutant of the Jurkat T cell line (JCaM1) is available that does not express lck kinase (Straus et al., 1992, Cell 70:585-593). Therefore, introduction of the lck gene into JCaM1 by transfection or transduction permits specific perturbation of exon expression states of T cell activation regulated by the lck kinase. The efficiency of transfection or transduction, and thus the level of perturbation, is dose related. The method is generally useful for providing perturbations of gene expression or protein abundances in cells not normally expressing the genes to be perturbed.

5.8.3. Methods of Modifying RNA Abundances or Activities

Methods of modifying RNA abundances and activities and thus exon abundances currently fall within three classes, ribozymes, antisense species, and RNA aptamers (Good et al., 1997, Gene Therapy 4: 45-54). Controllable application or exposure of a cell to these entities permits controllable perturbation of RNA abundances.

Ribozymes are RNAs which are capable of catalyzing RNA cleavage reactions. (Cech, 1987, Science 236:1532-1539; PCT International Publication WO 90/11364, published Oct. 4, 1990; Sarver et al., 1990, Science 247: 1222-1225). "Hairpin" and "hammerhead" RNA ribozymes can be designed to specifically cleave a particular target mRNA. Rules have been established for the design of short RNA molecules with ribozyme activity, which are capable of cleaving other RNA molecules in a highly sequence specific way and can be targeted to virtually all kinds of RNA. (Haseloff et al., 1988, Nature 334:585-591; Koizumi et al., 1988, FEBS Lett., 228:228-230; Koizumi et al., 1988, FEBS Lett., 239: 285-288). Ribozyme methods involve exposing a cell to, inducing expression in a cell, etc. of such small RNA ribozyme molecules. (Grassi and Marini, 1996, Annals of Medicine 28: 499-510; Gibson, 1996, Cancer and Metastasis Reviews 15: 287-299).

Ribozymes can be routinely expressed in vivo in sufficient number to be catalytically effective in cleaving mRNA, and thereby modifying mRNA abundances in a cell. (Cotten et al., 1989, Ribozyme mediated destruction of RNA in vivo, The EMBO J. 8:3861-3866). In particular, a ribozyme coding DNA sequence, designed according to the previous rules and synthesized, for example, by standard phosphoramidite chemistry, can be ligated into a restriction enzyme site in the anticodon stem and loop of a gene encoding a tRNA, which can then be transformed into and expressed in a cell of interest by methods routine in the art. Preferably, an inducible promoter (e.g., a glucocorticoid or a tetracycline response element) is also introduced into this construct so that ribozyme expression can be selectively controlled. tDNA genes (i.e., genes encoding tRNAs) are useful in this application because of their small size, high rate of transcription, and ubiquitous expression in different kinds of tissues. Therefore, ribozymes can be routinely designed to cleave virtually any mRNA sequence, and a cell can be routinely transformed with DNA coding for such ribozyme sequences such that a controllable and catalytically effective amount of the ribozyme is expressed. Accordingly the abundance of virtually any RNA species in a cell can be perturbed.

In another embodiment, activity of a target RNA (preferable mRNA) species, specifically its rate of translation, can be controllably inhibited by the controllable application of antisense nucleic acids. An "antisense" nucleic acid as used herein refers to a nucleic acid capable of hybridizing to a sequence-specific (e.g., non-poly A) portion of the target RNA, for example its translation initiation region, by virtue of some sequence complementarity to a coding and/or non-coding region. The antisense nucleic acids of the invention can be oligonucleotides that are double-stranded or single-stranded, RNA or DNA or a modification or derivative thereof, which can be directly administered in a controllable manner to a cell or which can be produced intracellularly by transcription of exogenous, introduced sequences in controllable quantities sufficient to perturb translation of the target RNA.

Preferably, antisense nucleic acids are of at least six nucleotides and are preferably oligonucleotides (ranging from 6 to about 200 oligonucleotides). In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide may include other appending groups such as peptides, or agents facilitating transport across the cell membrane (see, e.g., Letsinger et al., 1989, Proc. Natl. Acad. Sci. U.S.A. 86: 6553-6556; Lemaitre et al., 1987, Proc. Natl. Acad. Sci. 84: 648-652; PCT Publication No. WO 88/09810, published Dec. 15, 1988), hybridization-triggered cleavage agents (see, e.g., Krol et al., 1988, BioTechniques 6: 958-976) or intercalating agents (see, e.g., Zon, 1988, Pharm. Res. 5: 539-549).

In a preferred aspect of the invention, an antisense oligonucleotide is provided, preferably as single-stranded DNA. The oligonucleotide may be modified at any position on its structure with constituents generally known in the art.

The antisense oligonucleotides may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

In another embodiment, the oligonucleotide comprises at least one modified sugar moiety selected from the group including, but not limited to, arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is a 2-α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15: 6625-6641).

The oligonucleotide may be conjugated to another molecule, e.g., a peptide, hybridization triggered cross-linking agent, transport agent, hybridization-triggered cleavage agent, etc.

The antisense nucleic acids of the invention comprise a sequence complementary to at least a portion of a target RNA species. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a target RNA it may contain and still form a stable duplex (or triplex, as the case may be). One skilled in the art can ascertain a tolerable degree of mismatch by use of standard procedures to determine the melting point of the hybridized complex. The amount of antisense nucleic acid that will be effective in the inhibiting translation of the target RNA can be determined by standard assay techniques.

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16: 3209), methylphosphonate oligonucleotides can be prepared by use of controlled pore glass polymer supports (Sarin et al., 1988, Proc. Natl. Acad. Sci. U.S.A. 85: 7448-7451), etc. In another embodiment, the oligonucleotide is a 2'-0-methylribonucleotide (Inoue et al., 1987, Nucl. Acids Res. 15: 6131-6148), or a chimeric RNA-DNA analog (Inoue et al., 1987, FEBS Lett. 215: 327-330).

The synthesized antisense oligonucleotides can then be administered to a cell in a controlled manner. For example, the antisense oligonucleotides can be placed in the growth environment of the cell at controlled levels where they may be taken up by the cell. The uptake of the antisense oligonucleotides can be assisted by use of methods well known in the art.

In an alternative embodiment, the antisense nucleic acids of the invention are controllably expressed intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequences encoding the antisense RNAs can be by any promoter known in the art to act in a cell of interest. Such promoters can be inducible or constitutive. Most preferably, promoters are controllable or inducible by the administration of an exogenous moiety in order to achieve controlled expression of the antisense oligonucleotide. Such controllable promoters include the Tet promoter. Less preferably usable promoters for mammalian cells include, but are not limited to: the SV40 early promoter region (Bernoist and Chambon, 1981, Nature 290: 304-310), the promoter contained in the 3' long terminal repeat of Rous sarcoma virus (Yamamoto et al., 1980, Cell 22: 787-797), the herpes thymidine kinase promoter (Wagner et al., 1981, Proc. Natl. Acad. Sci. U.S.A. 78: 1441-1445), the regulatory sequences of the metallothionein gene (Brinster et al., 1982, Nature 296: 39-42), etc.

Therefore, antisense nucleic acids can be routinely designed to target virtually any mRNA sequence, and a cell can be routinely transformed with or exposed to nucleic acids coding for such antisense sequences such that an effective and controllable amount of the antisense nucleic acid is expressed. Accordingly the translation of virtually any RNA species in a cell can be controllably perturbed.

In still another embodiment, RNA aptamers can be introduced into or expressed in a cell. RNA aptamers are specific RNA ligands for proteins, such as for Tat and Rev RNA (Good et al., 1997, Gene Therapy 4: 45-54) that can specifically inhibit their translation.

Post-transcriptional gene silencing (PTGS) or RNA interference (RNAi) can also be used to modify RNA abundances (Guo et al., 1995, Cell 81:611-620; Fire et al., 1998, Nature 391:806-811). In RNAi, dsRNAs are injected into cells to specifically block expression of its homologous gene. In particular, in RNAi, both the sense strand and the anti-sense strand can inactivate the corresponding gene. It is suggested that the dsRNAs are cut by nuclease into 21-23 nucleotide fragments. These fragments hybridize to the homologous region of their corresponding mRNAs to form double-stranded segments which are degraded by nuclease (Grant, 1999, Cell 96:303-306; Tabara et al., 1999, Cell 99:123-132; Zamore et al., 2000, Cell 101:25-33; Bass, 2000, Cell 101: 235-238; Petcherski et al., 2000, Nature 405:364-368). Therefore, in one embodiment, one or more dsRNAs having sequences homologous to the sequences of one or more mRNAs whose abundances are to be modified are transfected into a cell or tissue sample. Any standard method for introducing nucleic acids into cells can be used.

6. EXAMPLES

The following examples are presented by way of illustration of the present invention, and are not intended to limit the present invention in any way. In particular, the examples presented herein below describe the analysis of the human Annexin VII gene and analysis of the exon expression states of human chromosome 22 in various different cell types.

6.1. Example 1

Alternative Splicing of the Annexin VII Gene

Annexin VII gene is a member of the annexin family of calcium-dependent phospholipid binding proteins that contains 14 exons which are distributed over 34 kb of genomic DNA on human chromosome 10 (Burns et al., 1989, *Proc. Natl. Acad. Sci. U.S.A.* 85:3798-3802). An alternatively spliced exon results in two mRNA transcripts of 2.0 kb and 2.4 kb, respectively, which have been shown to generate two protein isoforms differing in their N-terminal domain (Shirvan et al., 1994, *Biochemistry*, 33: 6888-6901). The alternative splicing event is tissue specific; the long form of the mRNA is prevalent in brain, heart and skeletal muscle while the short form is present in lung and smooth muscle (Magendzo et al., 1991, *The Journal of Biological Chemistry*, 266:3228-3232). In the long transcript all 14 exons are present while in the short transcript the $6^{th}$ exon that encodes a unique 22 amino acids insert in the N-terminus of the protein is missing.

A DNA array containing 25,000 different exon-specific 60-mers probes was designed to quantitatively monitor alternative splicing for 10 human genes (Table 1). For the Annexin VII gene, 706 different 60 mer probes were tiled in 3 by steps across the entire 2176 by of the long version of the mRNA which contains all 14 exons (Accession Number NM_004034). The array also contained ~2,000 control sequences which were synthesized around the perimeter and short diagonal stripes across the array. The sequence of the control probes synthesized around the perimeter of the array is (3'-5'): CCTATGTGACTGGTCGATGCTACTA [SEQ ID NO:1]. The "DRIZZLE" control probes that are synthesized in diagonal stripes are made up of two sequences, alternating diagonally: (3'-5'):AACAGTATGAAGAGTACCAAC-CTATGTGACTGGTCGATGCTACTA [SEQ ID NO:2] and (3'-5'):TTTTTTTTTTAACAGTATGAAGAGTAC-CAAGTGTGCCTATGTGACTGGTCG ATGCTACTA [SEQ ID NO:3]. Complementary oligonucleotides (5' end-labelled with Cy5 or Cy3) are spiked into the hybridization mix at 5 pM. The remaining 21,500 60-mers correspond to exon specific probes for 9 other human genes listed in Table 1. The array was synthesized on a 1×3 inch glass slide using ink jet technology developed by Rosetta Inpharmatics (see, e.g., Blanchard & Friend, 1999, *Nat. Biotechnol.* 17:953).

TABLE 1

List of genes represented on the 10-gene exon array

| Gene Name | Description | Accession Number |
| --- | --- | --- |
| HUMMYOHCB | Human nonmuscle myosin heavy chain-B (MYH10) mRNA | gi\|641957\|gb\|M69181 |
| DYSTROPHIN | muscular dystrophy, Duchenne and Becker types | gi\|5032282\|ref\|NM_004006.1 |
| PLEC1 | Human plectin | gi\|1477645\|gb\|U53204.1\|HSU53204 |
| Mysosin Light | Mysosin Light Chain Alkali | M22919 |
| ANXA7 | *Homo sapiens* annexin A7 | gi\|4809278\|ref\|NM_004034.1\| |
| HUMABLA | Human c-abl gene | gi\|177942\|gb\|M14752.1\| |
| HUMINTB1A | Human integrin beta-1 subunit | gi\|186500\|gb\|M34189.1 |
| HUMEBVR | Human CR2/CD21/C3d/Epstein-Barr virus receptor | gi\|181939\|gb\|M26004.1\| |
| ACHE | Acetylcholinesterase | gi\|7710111\|ref\|NM_015831.1\| |
| ALAD | erythroid transcript | X64467 |

Target polynucleotides were obtained by preparing total RNA from three different tissues: skeletal muscle (Stratagene, #780074), pulmonary artery smooth muscle (Stratagene, #780066) and brain (Clontech, #64020-1). Poly-A+ RNA (mRNA) was isolated from each of the total RNA preparations and labeled using reverse transcription primed with a mixture of random 9-mers and d(T)-20 primers. Specifically, 1.5 µg of mRNA was mixed with 1.5 µg of random 9-mers and 1.5 µg of d(T)-20, and the mixture was incubated for 10 minutes at 70° C., 10 minutes at 4° C., and 10 minutes at 22° C. To this mixture was added 0.5 mM amino-allyl dUTP (Sigma A-0410), 0.5 mM dNTP, 1×RT buffer, 5 mM MgCl$_2$, 10 mM DTT, and 200 units Superscript (GibcoBRL), bringing the final reverse transcription reaction volume to 100 µl. This reverse transcription reaction was incubated for 10 minutes at 42° C., then the RNA was hydrolyzed by adding 20 µl EDTA+NaOH and incubating at 65° C. for 20 minutes. The reaction was neutralized by adding 20 µl of 1M Tris-HCl pH 7.6. The resulting amino-allyl labeled single-stranded cDNA was purified using a Microcon-30 (Millipore, Bedford, Mass.). The purified cDNA from the different tissues was coupled to either Cy3 or Cy5 dye using a Cy Dye™ kit (Amersham Pharmacia, Piscataway, N.J., #Q15108). Prior to analysis on the array, the appropriate Cy3 and Cy5 labeled samples were combined and added to 3 ml of hybridization solution, consisting of 1M NaCl, 50 mM MES (pH 6.4), 0.50% Sarcosine™, and 30% formamide. The hybridization solution containing the combined samples was then placed in a plastic bag with the array and incubated for 12 hours at 42° C. on a rotisserie to allow the labeled target polynucleotides to hybridize to the array. Following the hybridization step, the array was washed for 20 seconds at room temperature in a beaker containing 50 ml of the hybridization solution, followed by an additional 20 second wash in a low salt buffer (10 mM NaCl, 50 mM MES (pH 6.4), and 0.005% Sarcosine™), then scanned using a GMS 418 scanner (Genetic Microsystems). FIG. 2 shows the scanned image (Cy-3 channel) of the 10 gene exon array hybridized with labeled RNA from smooth muscle. The region corresponding to the Annexin VII gene is shown and outlined in the inset. The 60-mer probes representing the $6^{th}$ exon (position 495-561) have very low hybridization levels relative to the probes from the rest of the gene indicating that the exon is spliced out. FIG. 3 shows a quantitative analysis of the hybridization data for the Annexin VII mRNA under three different conditions (skeletal muscle, smooth muscle, and brain). The data show that the long form of the Annexin VII mRNA (all 14 exons) is highly expressed in skeletal muscle while the short form (missing exon 6) is highly expressed in smooth muscle. The third panel shows that a mixture of the two isoforms appears to be present in the brain sample.

6.2. Example 2

Exon Expression State of Human Chromosome 22

The complete sequence of human chromosome 22 has recently been determined (*Nature* 1999 Dec. 2; 402(6761): 489-95). The chromosome spans 33.4 megabases and contains at least 545 genes and 134 pseudogenes. In addition, a total of 8,183 exons have been identified or predicted using a variety of gene prediction algorithms and experimental strategies and are available from http://sanger.ac.uk.

To monitor the exon expression state of chromosome 22, a DNA array comprising 60-mer probes for the 8,183 exons was designed and produced. For most exons, two 60-mer probes were designed using an algorithm that takes into account binding energies, base composition, sequence complexity, cross-hybridization binding energies, and secondary structure (see, Friend et al., U.S. patent application Ser. No. 09/561,487, filed Apr. 28, 2000; International Application No. PCT/US00/10202, filed Jul. 14, 2000). In some cases, e.g. exons shorter than 60 bp, only a single 60-mer probe was designed, e.g., by adding flanking sequences from adjacent exon or exons. A total of 15,511 60-mer probes were included in the DNA array to represent the 8,183 exons on human chromosome 22. These probes were synthesized on a 1×3 inch glass slide using ink jet technology developed by Rosetta Inpharmatics (Blanchard & Friend, 1999, *Nat. Biotechnol.* 17:953). The array further contained ~2,000 control sequences as described in Example 1 along with the 15,511 exon specific 60-mers. Some of the exon specific probes were printed in duplicate resulting in a total number of 25,000 probes on the 1×3 inch glass slide.

The exon expression state of chromosome 22 has been determined for a variety of different human tissues (see Table 2 below). For example, target polynucleotides were obtained by preparing total RNA from two cell lines, a human T lymphocyte cell line (Jurkat, ATCC # TIB-152) and a chronic myelogenous leukemia cell line (K562, ATCC #CCL-243), as described previously (Marton et al., 1998, Nat. Med. 4:1293-1301). Poly-A+ RNA (mRNA) was isolated from each cell line and labeled using reverse transcription primed with a mixture of random 9-mers and d(T)-20 primers as described in the previous section. The purified cDNA from the Jurkat cell line was coupled to Cy3 dye while the K562 sample was coupled to Cy5 dye using a Cy Dye™ kit (Amersham Pharmacia, Piscataway, N.J., #Q15108). The coupled samples were combined and hybridized to the chromosome 22 exon array as described above. In such manner, mRNA samples from diverse human cell lines and normal and diseased tissues were fluorescently labeled and hybridized in pairs to 69 individual, chromosome 22 exon arrays. FIG. 4a shows the scanned image (Cy-3 channel) of the chromosome 22 exon array hybridized with labeled RNA from a Jurkat cell line. The intensity data were analyzed using a correlation-based algorithm to assemble exons from local regions of genomic sequence into gene groups. The panel (402) of FIG. 4b shows a graphical display of the resulting ratio matrix across all 8,183 exons and 69 condition pairs. A gene identification algorithm was developed 1) to identify exons in a local neighborhood that are strongly correlated across condition pairs and then 2) to extend such regions by incorporating other local exons with similar expression behavior. The resultant groups of co-regulated exons constitute both candidate genes and candidate transcripts. The four panels of FIG. 4c are expanded regions of the chromosome 22 exon array that demonstrate the ability of our method to confirm the exons and structure of a known gene (403), to identify true positive and false positive exon predictions (404), to merge UniGene clusters into a single gene (405), and to authenticate ab initio gene predictions that are not supported by sequence similarity data (406). FIG. 5 shows a graphical representation of the exon expression states of chromosome 22 for the two cell samples.

TABLE 2

List of the cell samples that have been tested on the chromosome 22 exon array.

| # | Cat # | CLONTECH POLY A RNA LIST Sample | Cell Line | ATCC # |
|---|---|---|---|---|
| 1 | 6571-1 | Human Poly A RNA-Adrenal Gland | | |
| 2 | 6573-1 | Human Poly A RNA-Bone Marrow | | |
| 3 | 6516-1 | Human Poly A RNA-Brain | | |
| 4 | 6574-1 | Human Poly A RNA-Brain, amygdala | | |
| 5 | 6575-1 | Human Poly A RNA-Brain, caudate nucleus | | |
| 6 | 6543-1 | Human Poly A RNA-Brain, cerebellum | | |
| 7 | 6577-1 | Human Poly A RNA-Brain, corpus callosum | | |
| 8 | 6580-1 | Human Poly A RNA-Brain, substantia nigra | | |
| 9 | 6582-1 | Human Poly A RNA-Brain, thalamus | | |
| 10 | 6586-1 | Human Poly A RNA-Colorectal Adenocarcinoma | SW480 | ATCC #CCL228 |
| 11 | 6525-1 | Human Poly A RNA-Fetal Brain | | |
| 12 | 6526-1 | Human Poly A RNA-Fetal Kidney | | |
| 13 | 6527-1 | Human Poly A RNA-Fetal Liver | | |
| 14 | 6528-1 | Human Poly A RNA-Fetal Lung | | |
| 15 | 6533-1 | Human Poly A RNA-Heart | | |
| 16 | 6522-1 | Human Poly A RNA-Hela Cell | | |
| 17 | 6538-1 | Human Poly A RNA-Kidney | | |
| 18 | 6532-1 | Human Poly A RNA-Leukemia, Chronic Myelogenous | K-562 | ATCC #CCL243 |

TABLE 2-continued

List of the cell samples that have been tested on the chromosome 22 exon array.

| # | Cat # | CLONTECH POLY A RNA LIST Sample | Cell Line | ATCC # |
|---|---|---|---|---|
| | 6587-1 | Human Poly A RNA-Leukemia, Lymphoblastic | MOLT-4 | ATCC #CRL1582 |
| 20 | 6530-1 | Human Poly A RNA-Leukemia, Promyelocytic | HL-60 | ATCC #CCL240 |
| 21 | 6510-1 | Human Poly A RNA-Liver | | |
| 22 | 6524-1 | Human Poly A RNA-Lung | | |
| 23 | 6592-1 | Human Poly A RNA-Lung Carcinoma | A549 | ATCC #CCL185 |
| 24 | 6594-1 | Human Poly A RNA-Lymph Node | | |
| 25 | 6531-1 | Human Poly A RNA-Lymphoma, Burkitt's | Daudi | ATCC #CCL213 |
| 26 | 6588-1 | Human Poly A RNA-Lymphoma, Burkitt's | Raji | ATCC #CCL86 |
| 27 | 6591-1 | Human Poly A RNA-Melanoma | | |
| 28 | 6539-1 | Human Poly A RNA-Pancreas | | |
| 29 | 6584-1 | Human Poly A RNA-Pituitary Gland | | |
| 30 | 6518-1 | Human Poly A RNA-Placenta | | |
| 31 | 6546-1 | Human Poly A RNA-Prostate | | |
| 32 | 6534-1 | Human Poly A RNA-Salivary Gland | | |
| 33 | 6541-1 | Human Poly A RNA-Skeletal Muscle | | |
| 34 | 6547-1 | Human Poly A RNA-Small Intestine | | |
| 35 | 6593-1 | Human Poly A RNA-Spinal Chord | | |
| 36 | 6548-1 | Human Poly A RNA-Stomach | | |
| 37 | 6535-1 | Human Poly A RNA-Testes | | |
| 38 | 6536-1 | Human Poly A RNA-Thymus | | |
| 39 | 6570-1 | Human Poly A RNA-Thyroid | | |
| 40 | 6549-1 | Human Poly A RNA-Trachea | | |
| 41 | 6537-1 | Human Poly A RNA-Uterus | | |

6.3. Example 3

Whole Human Genome Exon Arrays and Whole Human Genome Exon Scan

Whole human genome exon arrays were designed based on a non-redundant subset of the 628,635 sequence elements that had been identified as potential exons by the Genscan program (Hubbard et al., 2000, Nature 403, 825) in the Jun. 15, 2000 version of the Ensembl human genome annotation data set (http://ensembl.org/). This subset consisted of 554,202 sequences. The subset is further reduced by repeat masking to a set of 442,785 sequences. For each of the predicted exons, the top two 60-mers were selected using the algorithm as described supra. In some cases (e.g. exons shorter than 60 bases), it was only possible to select a single 60 mer probe per exon. A set of 50 arrays containing a total of 1,090,408 60 mer polynucleotide probes representing such 442,785 exons was designed and fabricated. Among the subset of exons, 88,374 exons are confirmed exons. For 78,486 of the confirmed exons representing 17,997 validated genes, the reverse-complement probes were also selected and placed next to the regular probes on the array as negative control probes.

Fluorescently labeled cDNA from two cell lines (lymphoblast and colorectal carcinoma) was hybridized to the arrays. Sample preparation is as described supra. Single channel exon detection methods were applied to those exons in which reverse-complement probes were designed. In these cases, the raw intensity measurement for the FS probe and the corresponding raw intensity measurement for the RC probe were used in conjunction with the respective measurement errors to determine the significance of the FS probe intensity. RC probes were used to control for non-specific cross hybridization, given the reverse complement of a DNA sequence has sequence complexity that is equivalent to the forward strand sequence with respect to a variety of measures (e.g., measures such as GC content and GC trend are invariant under the reverse complement). An exon was called present if the intensity difference between the FS probe and RC probe was significant in either the red or green channel, and if the FS probe intensity was significantly above background in the channel the difference was considered most significant. Ratio-based exon detection methods and an alternative single channel detection method were applied whenever RC probes did not exist. Error models used in this analysis to assess ratio significance were as described in Hughes et al. The alternative single channel exon detection method consisted of computing the above-background significance for each probe intensity corresponding to an exon, slightly corrected for errors estimated from the FS/RC probe set. Of the 88,374 confirmed exons represented on the genome-wide exon arrays, 78,486 had corresponding RC probes. To assess the rate of false positives expected in the single-channel assessments, we used a similar detection procedure to determine the number of RC probe intensity measurements that were significantly greater than the corresponding FS probe intensity. Our results indicate that the false positive rate of detection using the single channel method was approximately 5%.

Analysis of fluorescence intensities permitted detection of 58% of the 78,486 exons comprising the set of Ensembl confirmed transcripts represented on the exon arrays. For 55% of these genes, more than half of the component exons were detected despite the fact that only two experimental conditions were tested. For predicted exons that did not meet the Ensembl "confirmed" criteria, the fraction detected fell to 34%. The false positive rate for this analysis was estimated to be approximately 5% from an analysis of a set of negative control probes included on the arrays. In addition to this intensity-based analysis, the amount of differential regulation was also assessed for exons in confirmed and predicted groups, and was found to be 15% and 7%, respectively. However, none of the predicted exons can be ruled out since only two experimental conditions were tested. A summary of the result of the whole human genome scan is shown in FIG. 7.

7. REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of the present invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

splicing site located in each of said plurality of different genes; and wherein said measuring step is performed by a method comprising:

(a) contacting a positionally-addressable array of polynucleotide probes with a nucleic acid sample comprising RNAs from said cell sample or cDNAs transcripted from said RNAs under conditions conducive to hybridizations between said probes and said RNAs or said cDNAs, wherein said array comprises a plurality of polynucleotide probes comprising different nucleotide sequences, wherein said plurality of polynucleotide probes are bound to different regions of said array and comprises variant junction probes that specifically hybridize to said different exon variants and each of said variant junction probes is complementary and hybridizes to a junction region of two adjacent exons of one of said variants from said cDNAs; and

What is claimed is:

1. A method for analyzing expression levels of different exon variants of a plurality of different genes in the genome of an organism in a cell sample derived from said organism, said method comprising measuring, in vitro, the expression levels of said different exon variants, each of said different exon variants being a different splicing variant of each of said plurality of different genes generated using a different 3' or 5'

(b) measuring levels of hybridizations between said variant junction probes and said RNAs or said cDNAs and analyzing the expression levels of said exon variants based on said levels of hybridizations.

2. The method of claim 1, wherein said plurality of different genes consists of at least 100 different genes.

3. The method of claim 1, wherein said plurality of different genes consists of at least 1,000 different genes.

4. The method of claim 1, wherein said plurality of different genes consists of at least 10,000 different genes.

5. The method of claim 1, wherein said plurality of polynucleotide probes consists of at least 100 different polynucleotide probes.

6. The method of claim 1, wherein said plurality of polynucleotide probes consists of at least 1,000 different polynucleotide probes.

7. The method of claim 1, wherein said plurality of polynucleotide probes consists of at least 10,000 different polynucleotide probes.

8. The method of claim 1, wherein said plurality of polynucleotide probes is 1,000 to 50,000 different polynucleotide probes.

9. The method of claim 1, wherein said positionally-addressable array has 100 to 1,000 different polynucleotide probes per 1 cm$^2$.

10. The method of claim 1, wherein said positionally-addressable array has 1,000 to 10,000 different polynucleotide probes per 1 cm$^2$.

11. The method of claim 1, wherein said positionally-addressable array has 10,000 to 50,000 different polynucleotide probes per 1 cm$^2$.

12. The method of claim 1, wherein said positionally-addressable array has more than 50,000 different polynucleotide probes per 1 cm$^2$.

13. The method of claim 1, wherein each of said different nucleotide sequences consists of 10 to 1,000 nucleotides.

14. The method of claim 1, wherein each of said different nucleotide sequences consists of 15 to 600 nucleotides.

15. The method of claim 1, wherein each of said different nucleotide sequences consists of 15 to 200 nucleotides.

16. The method of claim 1, wherein each of said different nucleotide sequences consists of 20 to 100 nucleotides.

17. The method of claim 1, wherein each of said different nucleotide sequences consists of 40 to 80 nucleotides.

18. The method of claim 1, wherein each of said different nucleotide sequences consists of 60 nucleotides.

19. The method of claim 1, wherein at least one probe in said plurality of polynucleotide probes comprises a linker sequence.

20. The method of claim 1, wherein at least one of said plurality of polynucleotide probes comprises a nucleotide sequence complementary and hybridizable to a multiexon in a gene in the genome of said organism.

21. The method of claim 20, wherein the nucleotide sequence of said at least one polynucleotide probe is complementary to a sequence spanning the splice junction between different exons in said multiexon.

22. The method of claim 20, wherein said sequence is complementary to a sequence comprising a full length exon flanked by sequences from an adjacent exon or exons in said multiexon.

23. The method of claim 1, wherein said array of polynucleotide probes further comprises control polynucleotide probes comprising sequences complementary and hybridizable to different introns of said plurality of genes in the genome of said organism.

24. The method of claim 1, wherein said expression levels are measured by detecting abundance of mRNA transcripts.

25. The method of claim 1, wherein said cell sample has been subjected to a perturbation.

26. The method of claim 25, wherein said organism is a human.

27. The method of claim 25, wherein said organism is a plant.

28. The method of claim 25, further comprising performing the method of claim 1 using another nucleic acid sample derived from a cell sample of the same type not subjected to said perturbation and comparing the expression levels of at least a portion of said plurality of different exon variants in said nucleic acid sample derived from said cell sample subjected to said perturbation with the nucleic acid expression levels of said at least portion of said plurality of different exon variants in said another nucleic acid sample.

29. The method of claim 28, wherein said comparing comprises determining the differences between the expression levels of each exon variant in said at least portion of said plurality of different exon variants in said nucleic acid sample derived from said cell sample subjected to said perturbation and the expression levels of the corresponding exon variants in said another nucleic acid sample derived from a cell sample of the same type not subjected to said perturbation.

30. The method of claim 25, wherein said perturbation is exposure of said cell sample to a drug.

31. The method of claim 25, wherein said perturbation is subjecting a genetic mutation in one or more genes of said plurality of different genes.

32. The method of claim 25, wherein said perturbation comprises mutating one or more genes of said plurality of different genes and exposure of said cell sample to a drug.

33. The method of claim 1, wherein said array of polynucleotide probes comprises one or more sets of successive overlapping probes covering the longest length exon among said cDNAs after the hybridizations.

34. The method of any one of claims 21 and 33, wherein each of said different nucleotide sequences consists of 15 to 200 nucleotides.

35. The method of claim 34, wherein each of said different nucleotide sequences consists of 20 to 100 nucleotides.

36. The method of claim 35, wherein each of said different nucleotide sequences consists of 40 to 80 nucleotides.

37. The method of claim 36, wherein each of said different nucleotide sequences consists of 60 nucleotides.

38. The method of claim 1, wherein said measurement comprises measuring, in vitro, the expression levels of at least 5 of said different exon variants.

39. The method of claim 38, wherein said measurement comprises measuring, in vitro, the expression levels of at least 10 of said different exon variants.

40. The method of claim 39, wherein said measurement comprise measuring, in vitro, the expression levels of at least 100 of said different exon variants.

41. The method of claim 40, wherein said measurement comprises measuring, in vitro, the expression levels of at least 1000 of said different exon variants.

42. The method of claim 1, wherein said organism is a human.

43. The method of claim 1, wherein said organism is a plant.

44. The method of claim 1, wherein said organism is a fungus.

45. The method of claim 25, wherein said organism is a fungus.

46. A method for analyzing expression levels of different splicing variants of a plurality of different genes in the genome of an organism in a cell sample derived from said organism, said method comprising:

(a) contacting a positionally-addressable array comprising polynucleotide probes with a sample comprising RNAs from said cell sample or cDNA transcribed from said RNAs under conditions conducive to hybridizations between said probes and said RNAs or said cDNAs, wherein said probes on the array comprise (i) two or more exon specific probes comprising different nucleotide sequences from each of said plurality of different genes in the genome of said organism, wherein each of said different nucleotide sequences is complementary and hybridizes to a sequence within a different individual exon of one of said plurality of different genes; and (ii) a plurality of variant junction probes for each of a plurality of different splicing variants of said plurality of different genes, each of said different splicing variants is generated using a different 3' or 5' splicing site located in each of said plurality of different genes, and each of said variant junction probes is complementary and hybridizes to a junction region of two adjacent exons of one of said variants from said cDNAs, each of said exon specific probes and variant junction probes are bound to a different region of said array and said array comprises a support; and (b) measuring levels of hybridizations (i) between each of said exon specific probes and said RNAs or said cDNAs, and (ii) between each of said variant junction probes and said RNAs or said cDNAs and analyzing the expression levels of said variants based on said levels of hybridizations.

47. A method for analyzing expression levels of different splicing variants of a plurality of different genes in the genome of an organism in a cell sample derived from said organism, said method comprising:

(a) contacting a positionally-addressable array comprising polynucleotide probes with a sample comprising RNAs from said cell sample or cDNAs transcribed from said RNAs under conditions conducive to hybridizations between said probes and said RNAs or said cDNAs, wherein said probes on the array comprise a plurality of junction specific probes comprising different nucleotide sequences from each of said plurality of different genes in the genome of said organism, wherein said junction specific probes are bound to different regions of said array and each of said different nucleotide sequences is complementary and hybridizes to a sequence spanning a junction region of two adjacent exons in one of said cDNAs, and wherein said plurality of junction specific probes comprise a plurality of variant junction probes for each of a plurality of different splicing variants of each gene in said plurality of different genes, each of said plurality of different splicing variants is generated using a different 3' or 5' splicing site located in each of said plurality of different genes, each of said variant junction probes is complementary and hybridizes to a junction region of two adjacent exons of one of said variants from said cDNAs and said array comprises a support; and (b) measuring levels of hybridizations between said plurality of variant junction probes and said RNAs or said cDNAs and analyzing the expression levels of said variants based on said levels of hybridizations.

48. The method of claim 46 or 47, wherein said plurality of different genes consists of at least 100 different genes.

49. The method of claim 48, wherein said plurality of different genes consists of at least 1,000 different genes.

50. The method of claim 49, wherein said plurality of different genes consists of at least 10,000 different genes.

51. The method of claim 46 or 47, wherein each of said different nucleotide sequences consists of 15 to 200 nucleotides.

52. The method of claim 51, wherein each of said different nucleotide sequences consists of 20 to 100 nucleotides.

53. The method of claim 52, wherein each of said different nucleotide sequences consists of 40 to 80 nucleotides.

54. The method of claim 53, wherein each of said different nucleotide sequences consists of 60 nucleotides.

* * * * *